United States Patent [19]

Hoshowski et al.

[11] Patent Number: 4,960,588

[45] Date of Patent: Oct. 2, 1990

[54] HAIR TREATMENT COMPOSITIONS TO IMPART DURABLE HAIR SET RETENTION PROPERTIES

[75] Inventors: Myra A. Hoshowski, Addison; Eugene Zeffren, Lincolnshire, both of Ill.

[73] Assignee: Helene Curtis, Inc., Chicago, Ill.

[21] Appl. No.: 272,060

[22] Filed: Nov. 16, 1988

[51] Int. Cl.$^5$ .................. A61K 7/075; A61K 7/11
[52] U.S. Cl. ............................. 424/71; 424/70; 424/47; 424/DIG. 1; 514/788
[58] Field of Search ............... 424/47, 70, 71, DIG. 1; 252/DIG. 13; 514/788

[56] References Cited

U.S. PATENT DOCUMENTS

| | | | |
|---|---|---|---|
| 3,958,581 | 5/1976 | Abegg et al. | 424/70 X |
| 4,206,195 | 6/1980 | Bolich, Jr. et al. | 424/71 X |
| 4,206,196 | 6/1980 | Davis | 424/71 X |
| 4,551,330 | 11/1985 | Wagman et al. | 424/70 X |
| 4,614,200 | 9/1986 | Hsiung et al. | 424/70 X |
| 4,834,971 | 5/1989 | Klenk et al. | 424/71 X |
| 4,840,791 | 6/1989 | Mathews et al. | 424/71 |
| 4,841,997 | 6/1989 | Petrow | 424/71 X |

Primary Examiner—Merrell C. Cashion, Jr.
Assistant Examiner—Susan S. Rucker
Attorney, Agent, or Firm—Marshall, O'Toole, Gerstein, Murray & Bicknell

[57] ABSTRACT

A hair setting composition that includes a water-insoluble amino- or substututed amino-containing compound, such as octylamine or an amino-functionalized silicone, and an ionizable metal salt, wherein the metal has a valence of at least II, such as aluminum chloride or zinc chloride, in a molar or molar-equivalent ratio of ionizable metal salt to water-insoluble amino-containing compound of at least 1:1, and having a pH in the range of about 2.7 to about 4.5, to provide unexpectedly durable hair set retention properties after application to human hair.

75 Claims, 23 Drawing Sheets

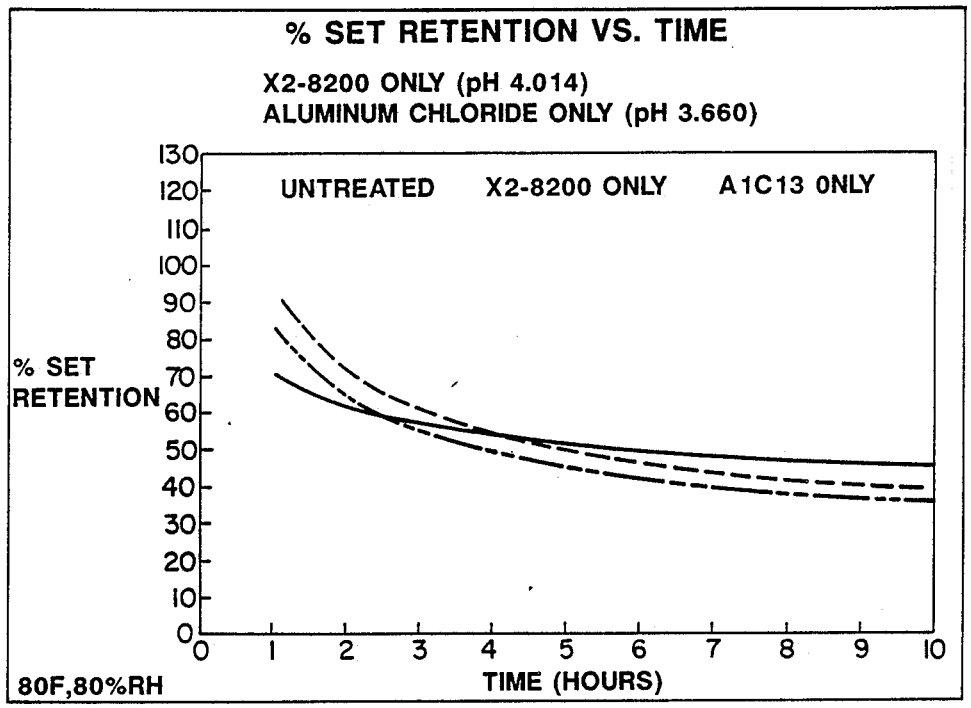
Fig. 1
Fig. 2
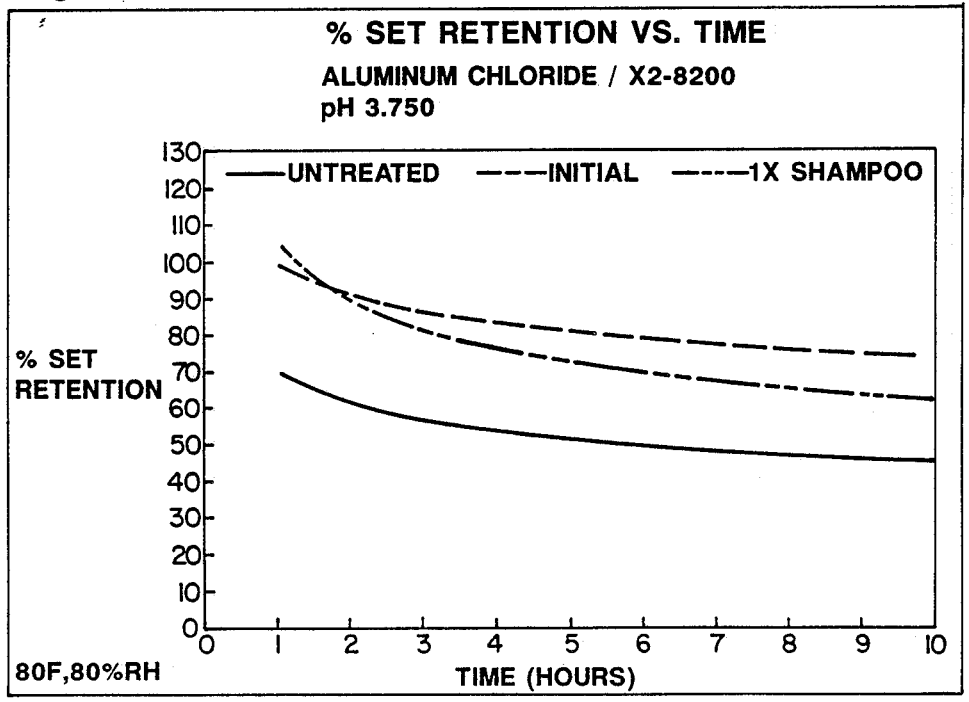

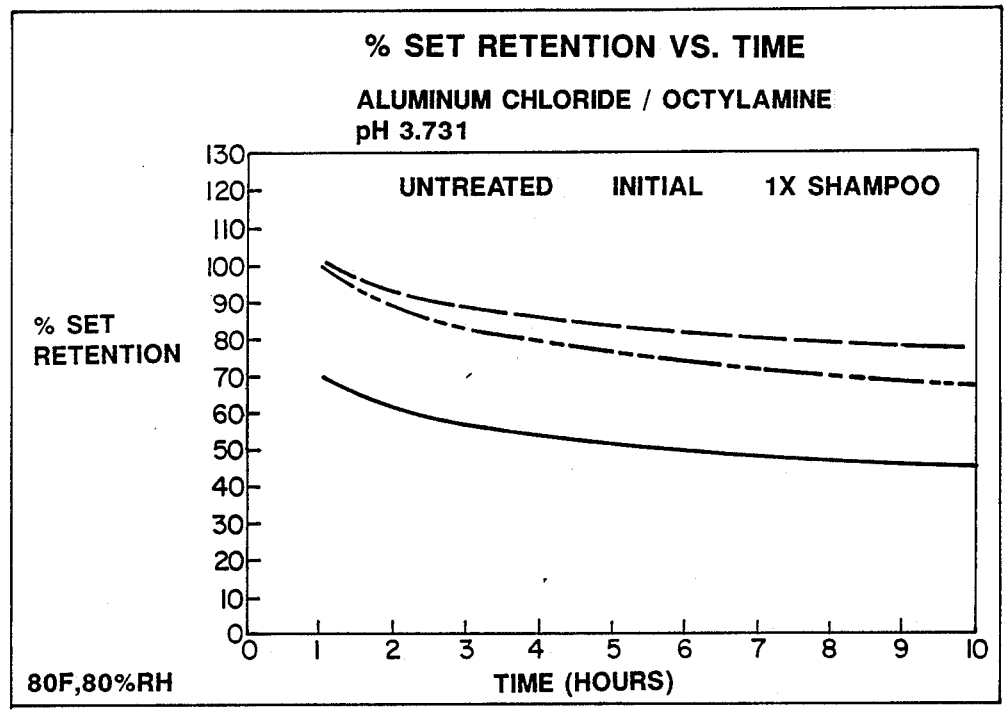
Fig. 3
Fig. 4
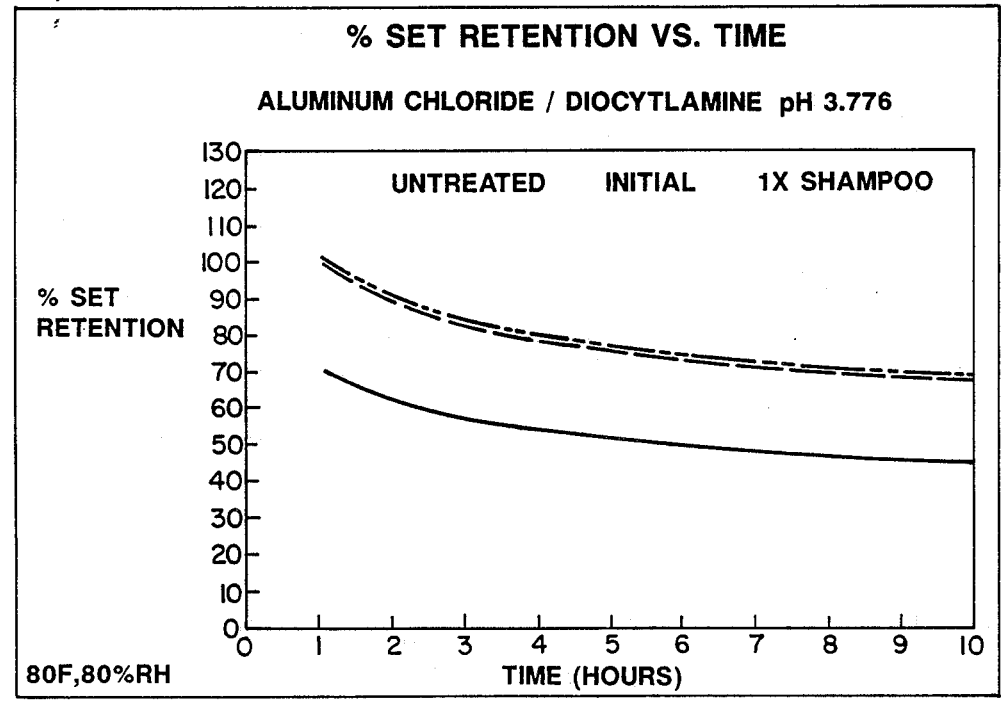

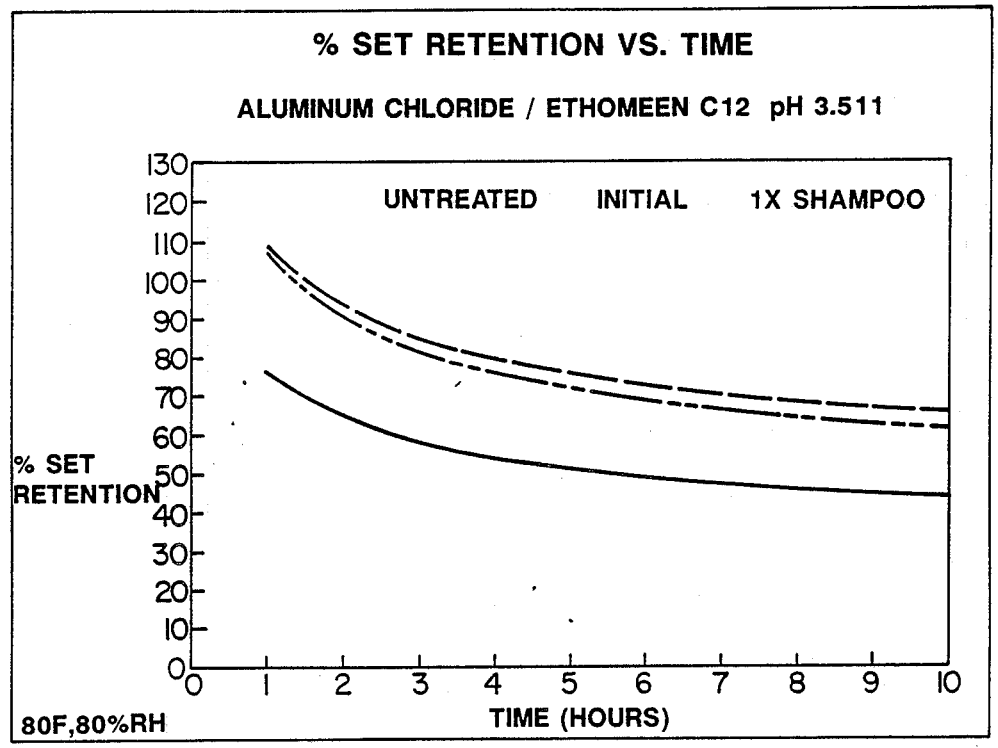
Fig. 7
Fig. 8
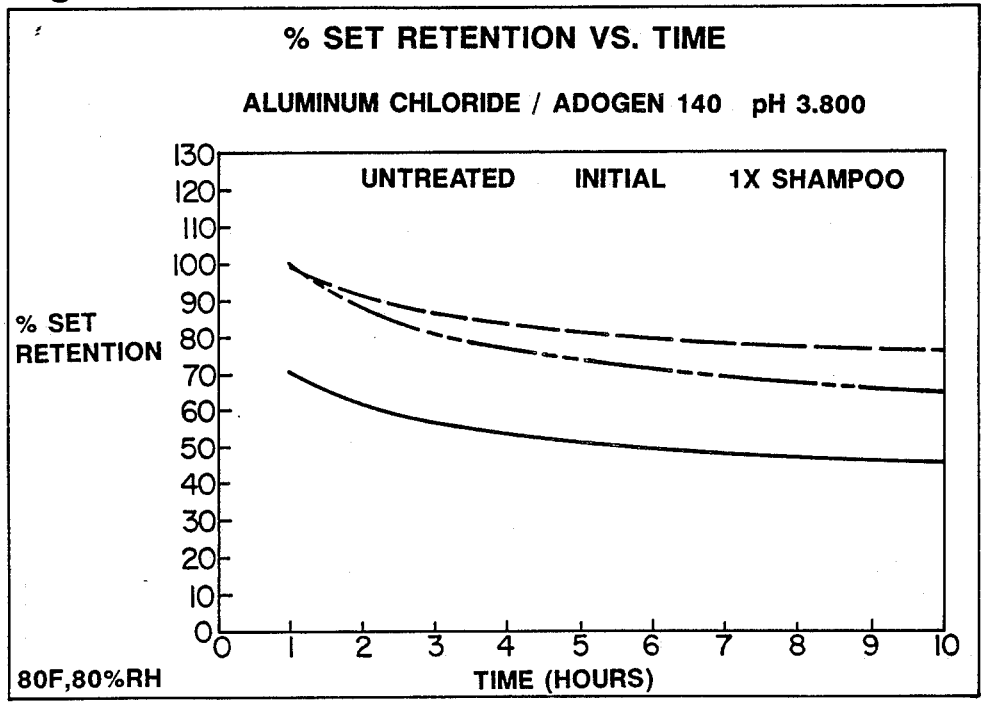

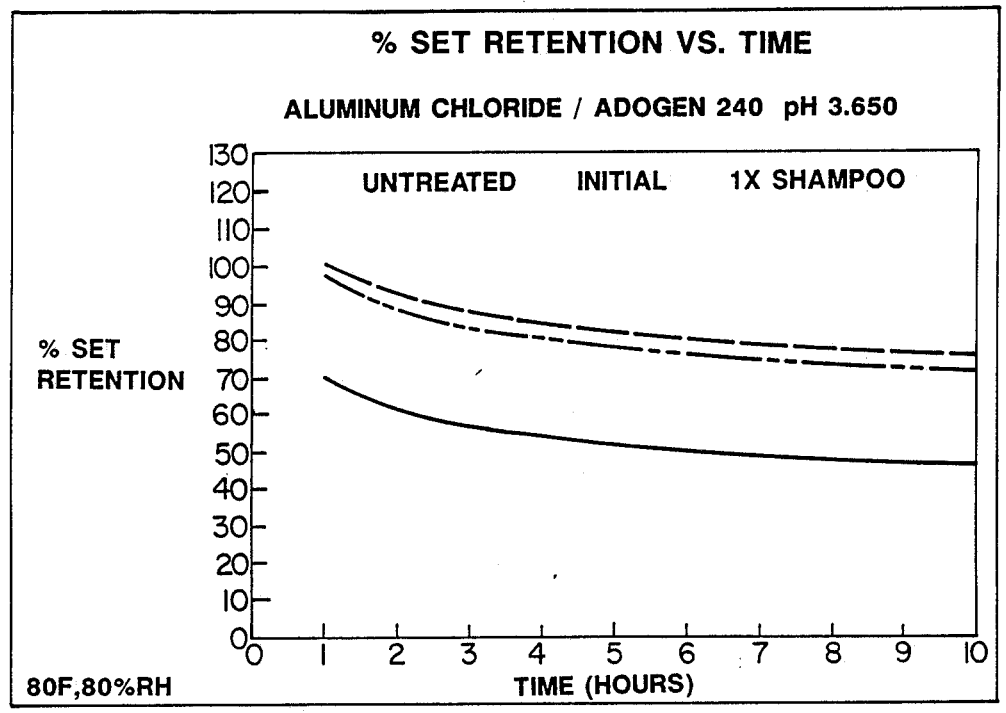
Fig. 9
Fig. 10
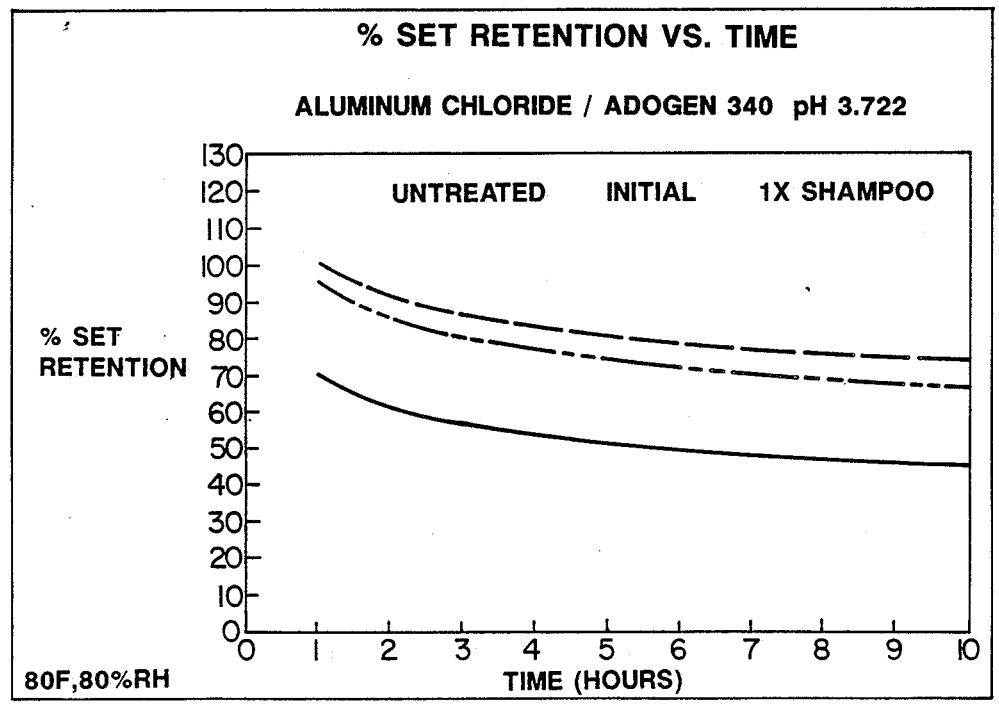

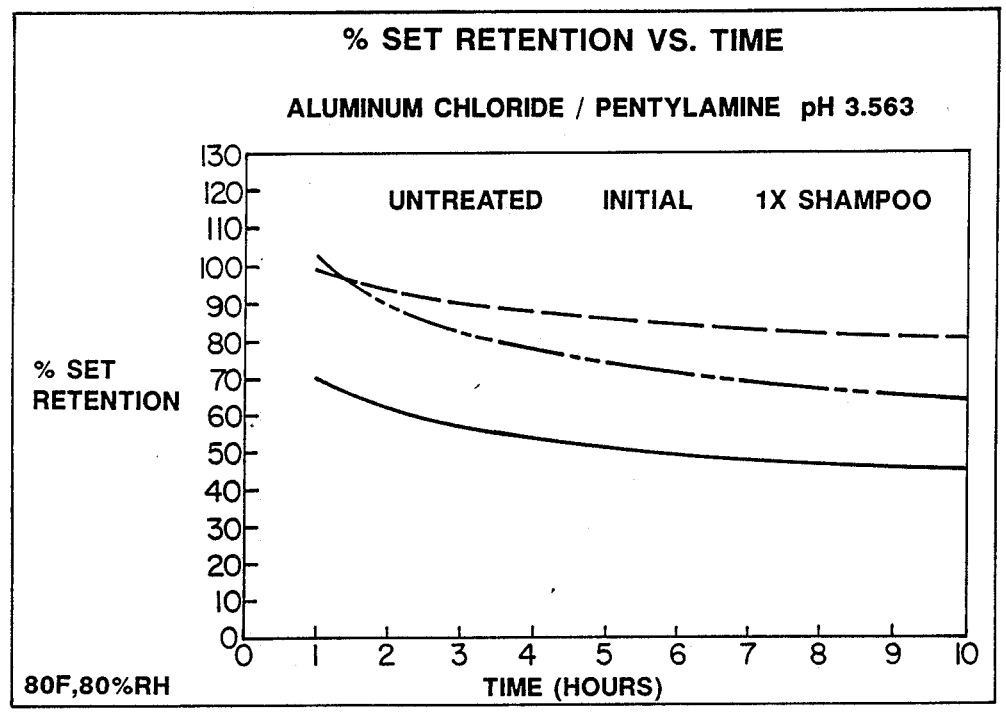
Fig. 11
Fig. 12
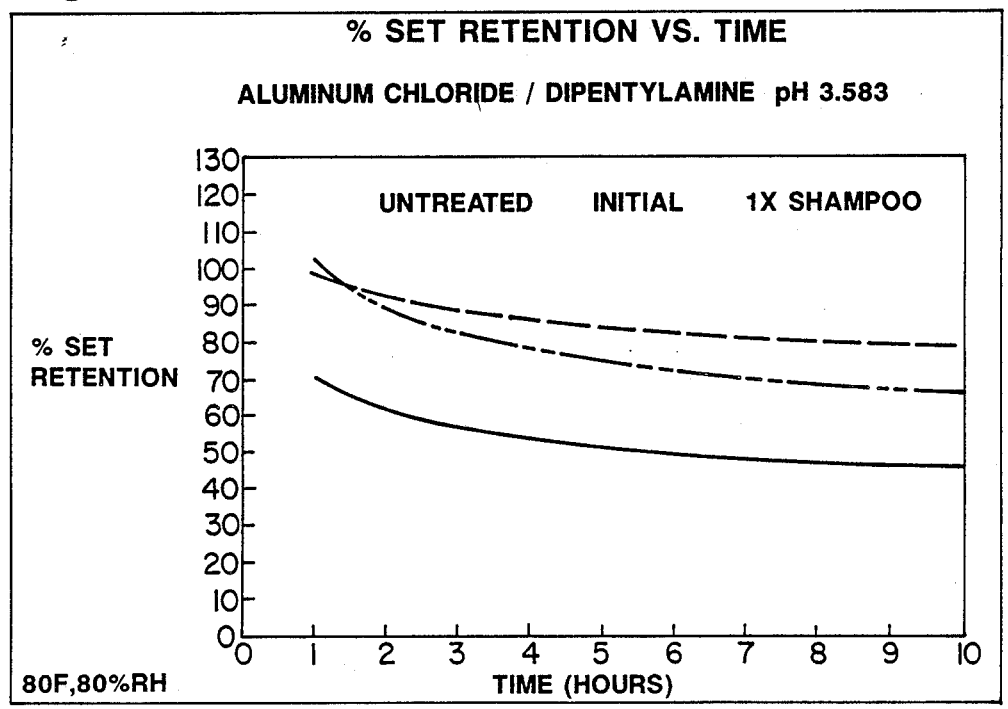

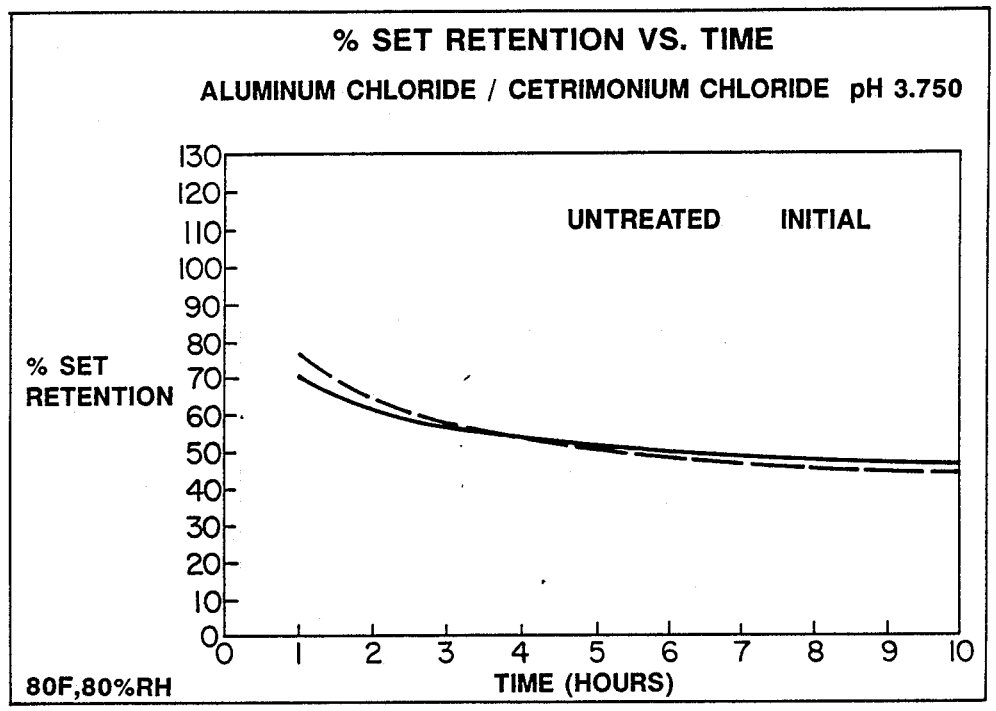
Fig. 13
Fig. 14
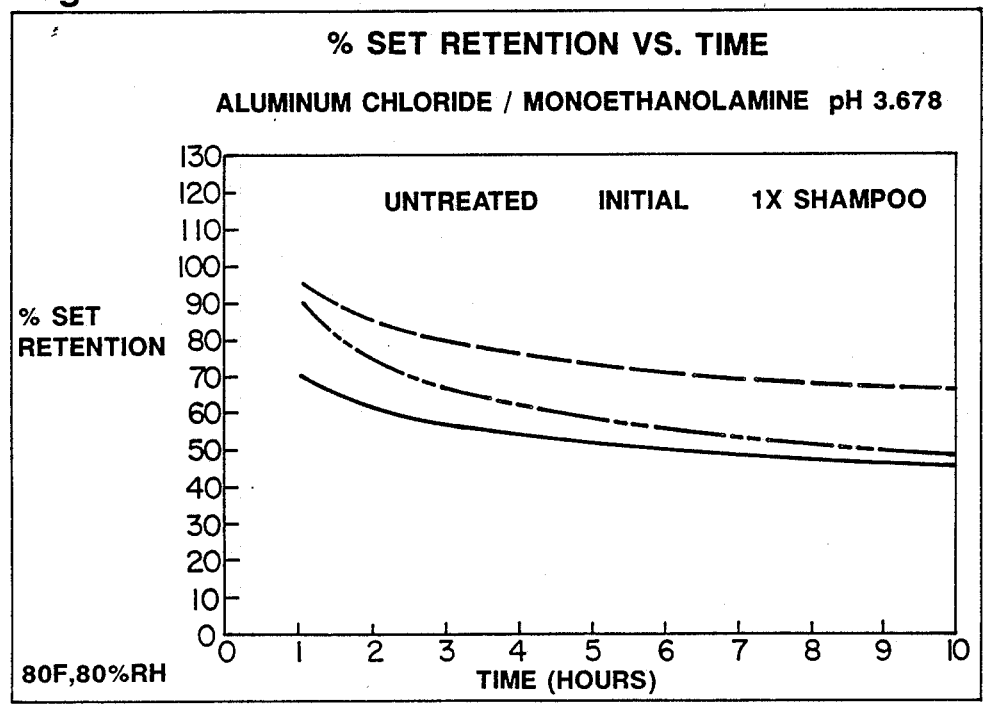

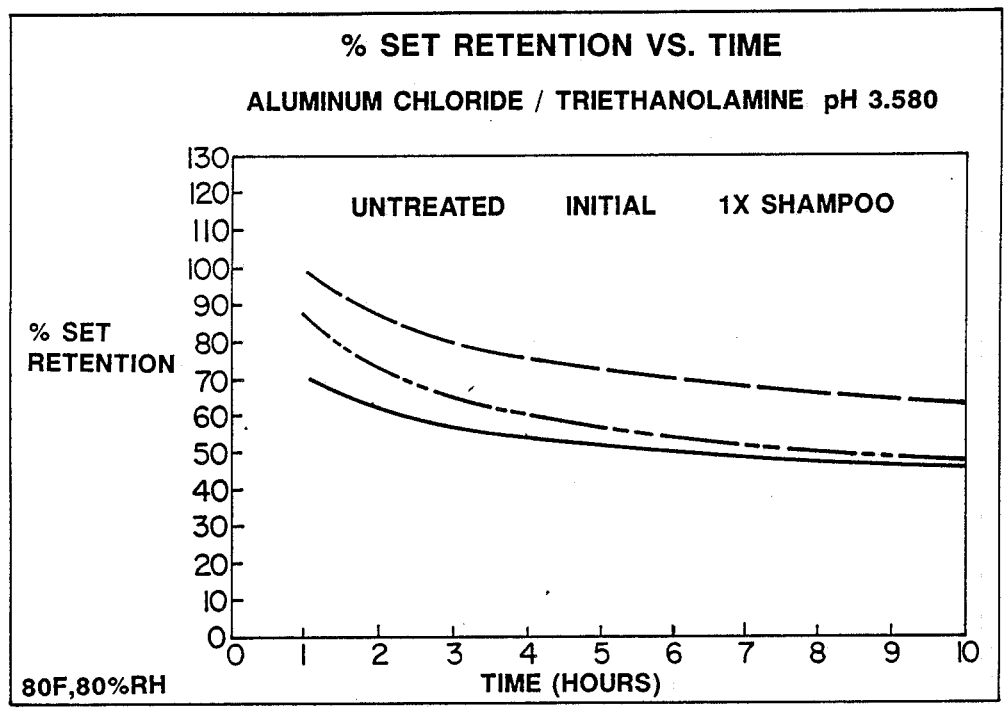
Fig. 15
Fig. 16
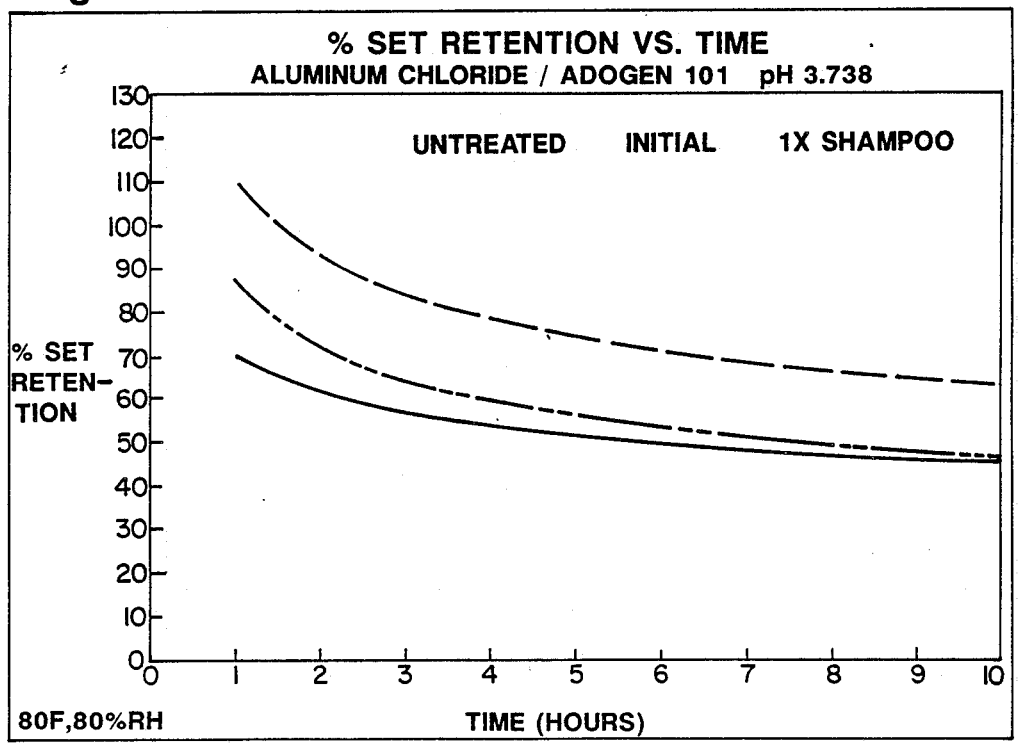

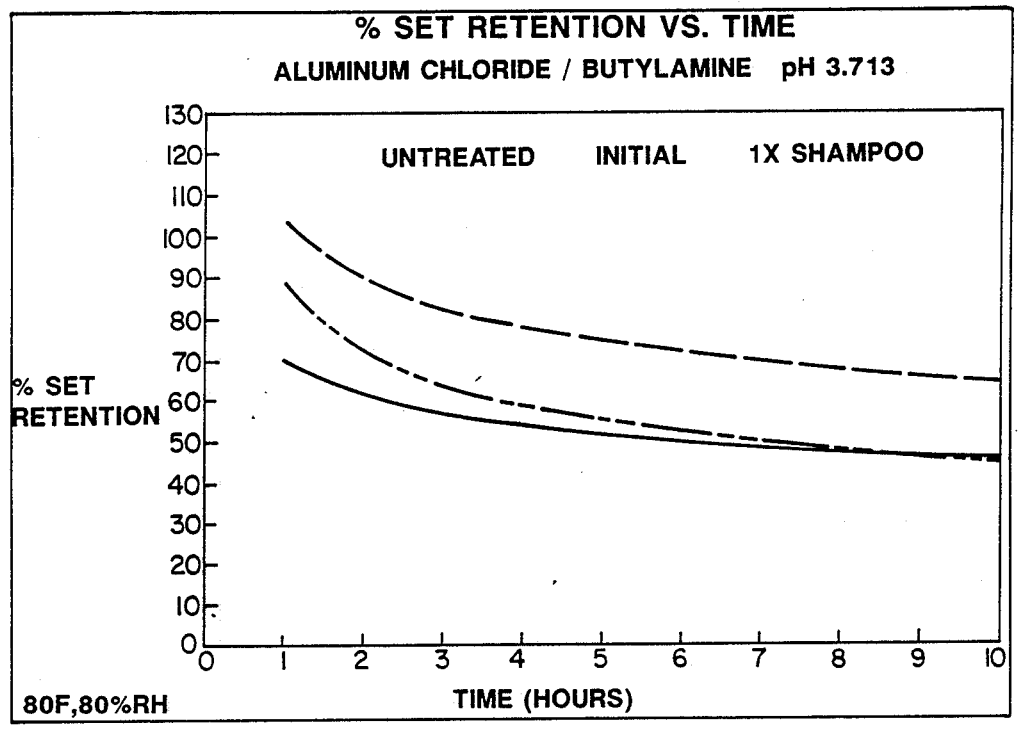
Fig. 17
Fig. 18
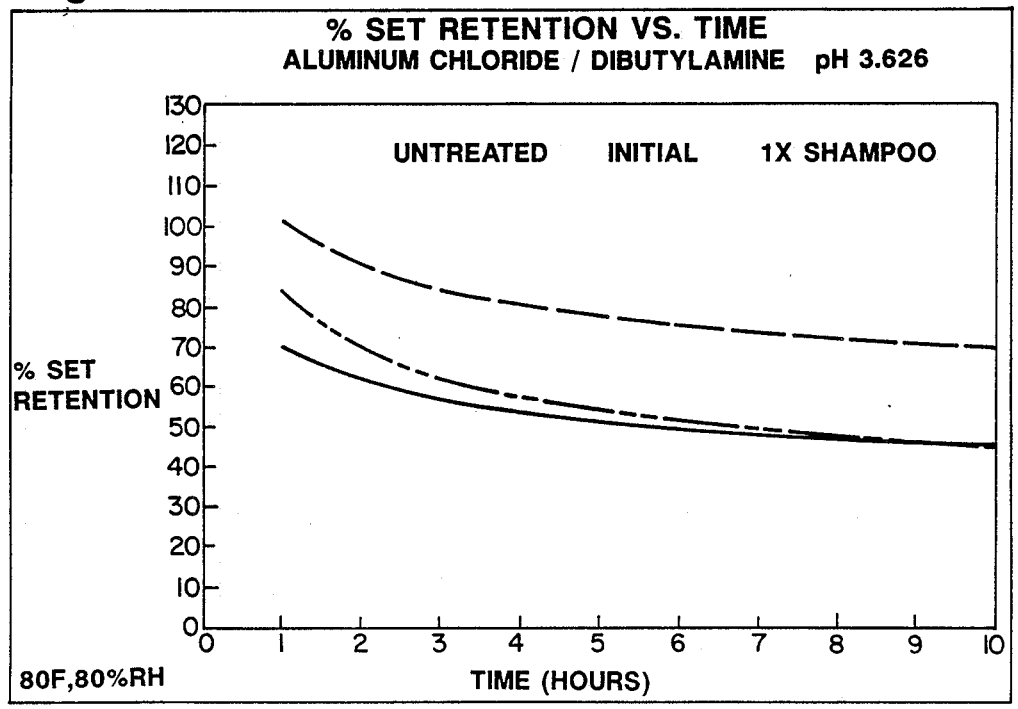

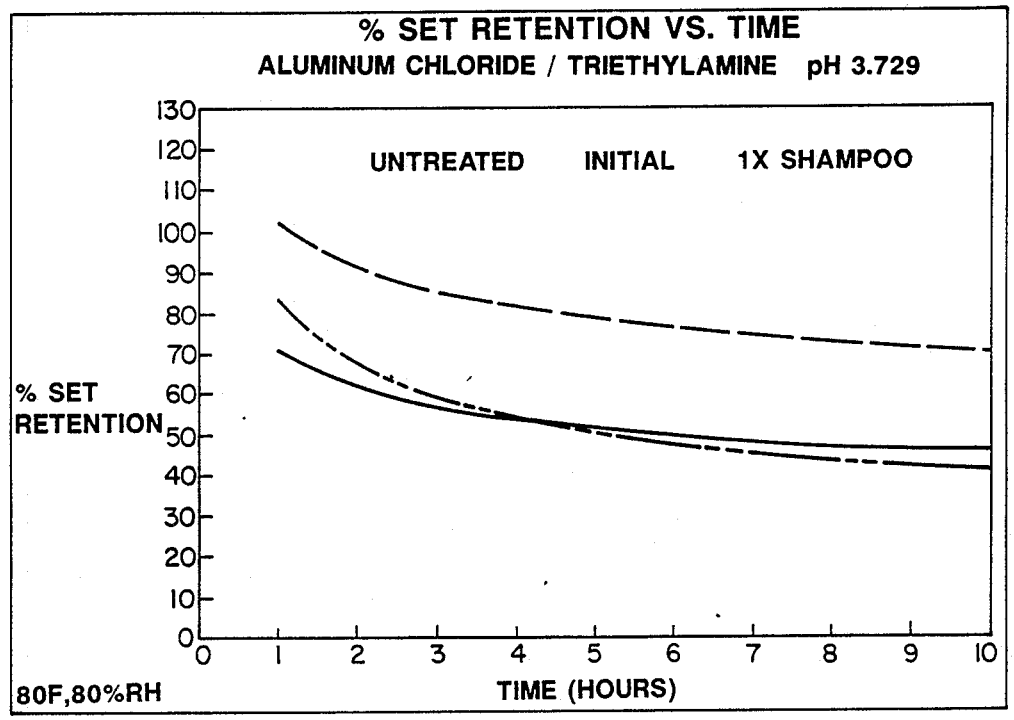
Fig. 19
Fig. 20
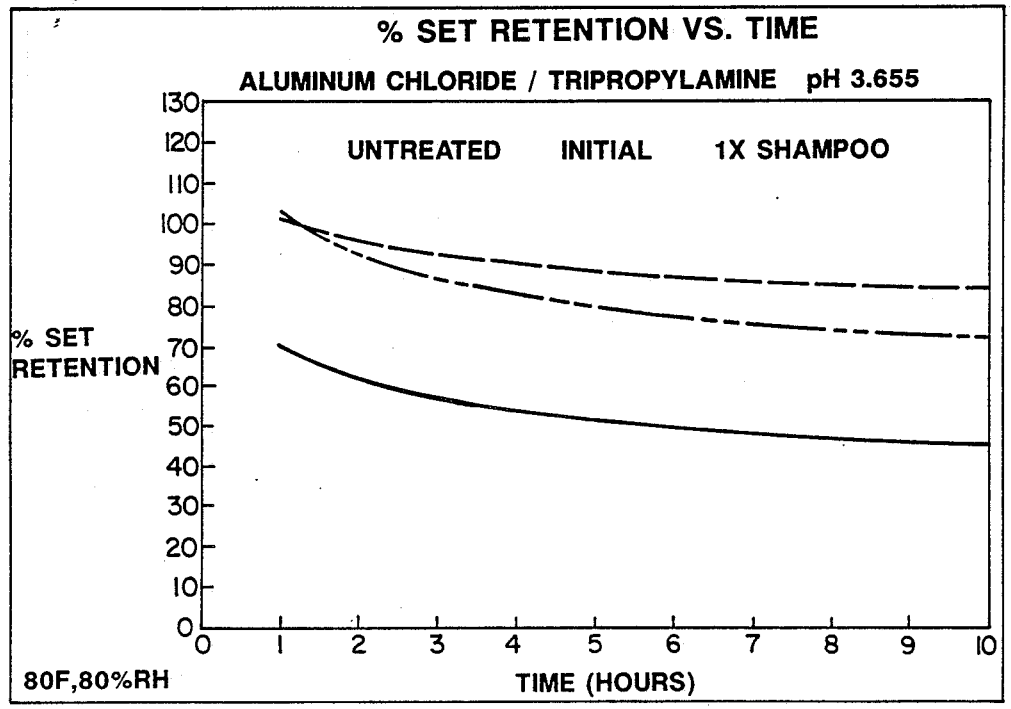

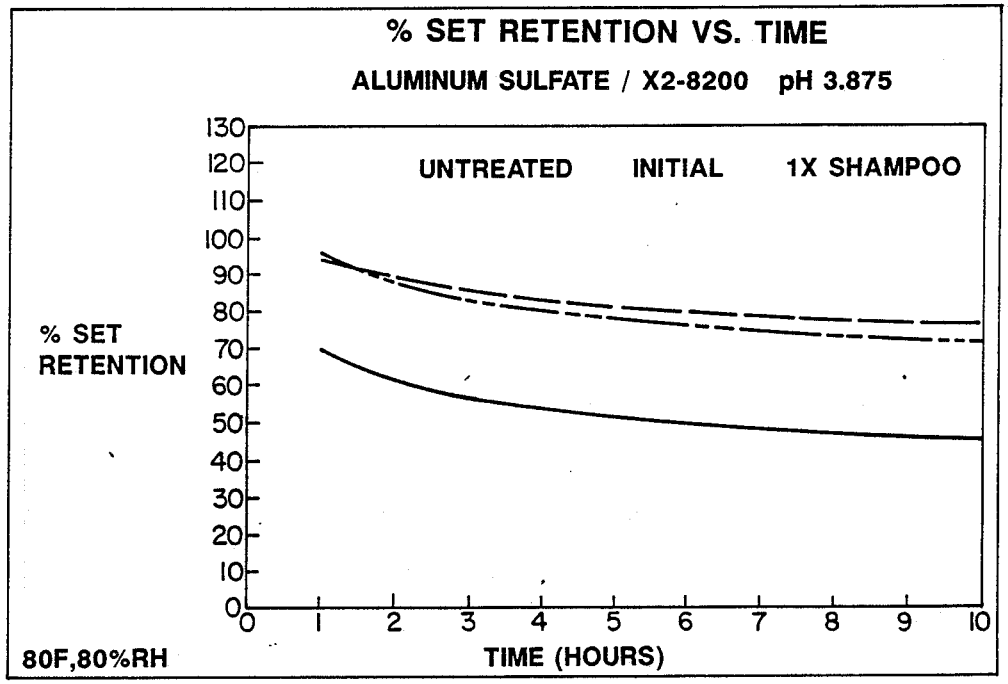
Fig. 21
Fig. 22
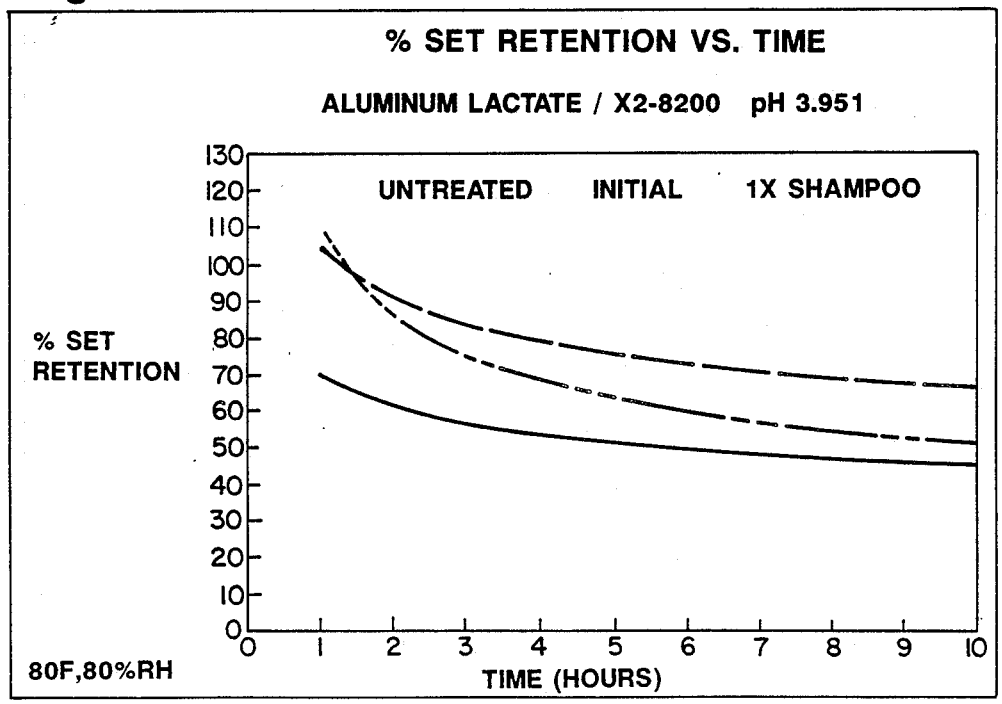

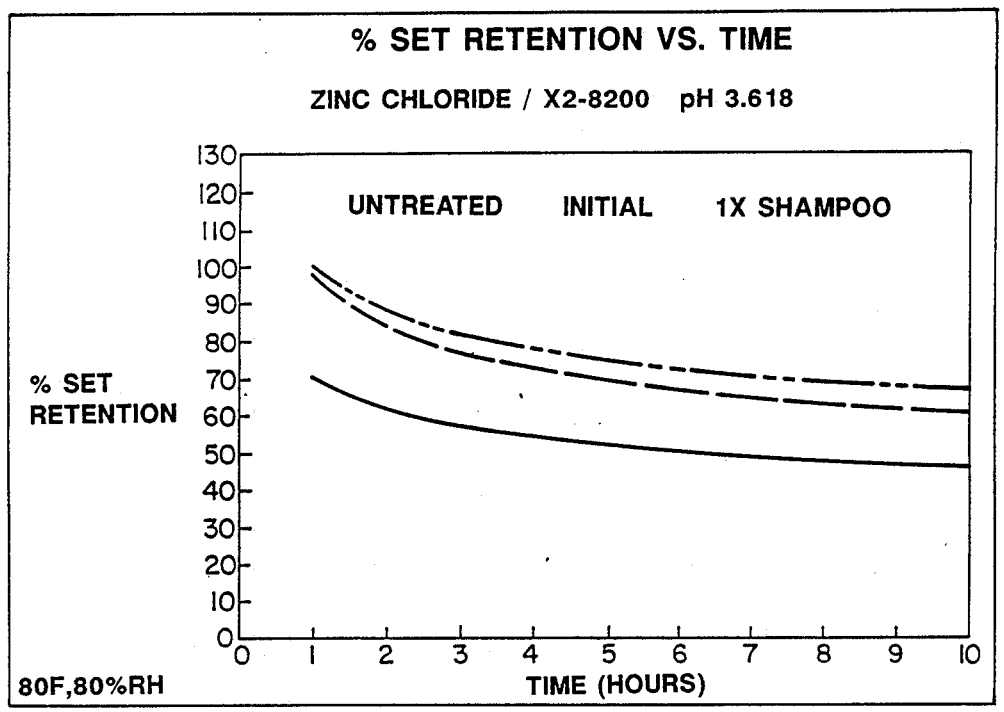
Fig. 25
Fig. 26
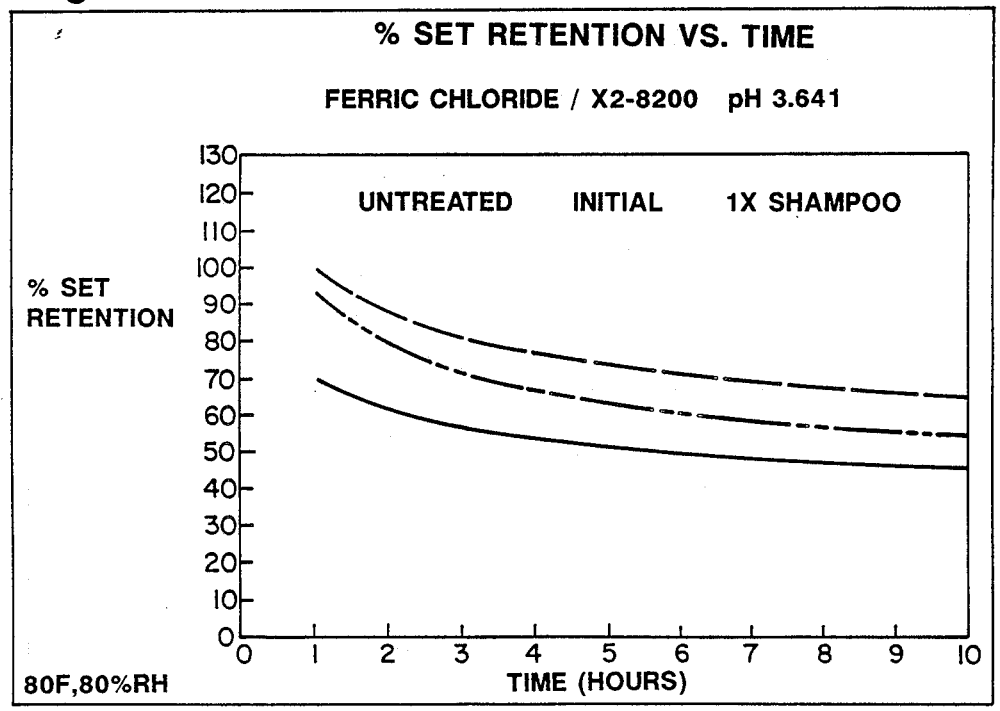

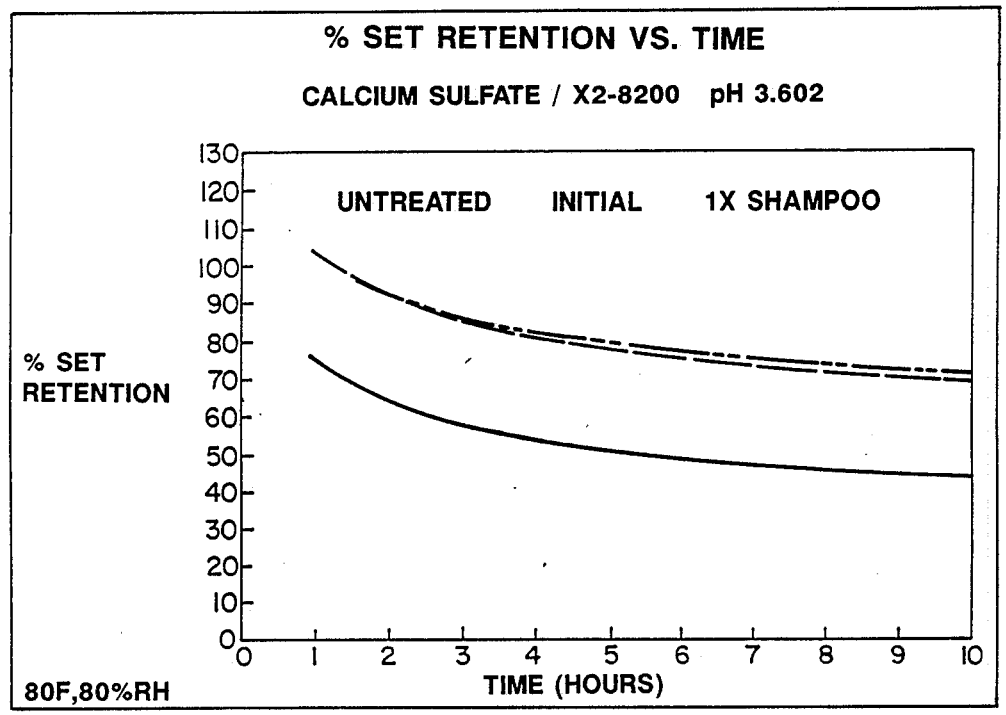
Fig. 27
Fig. 28
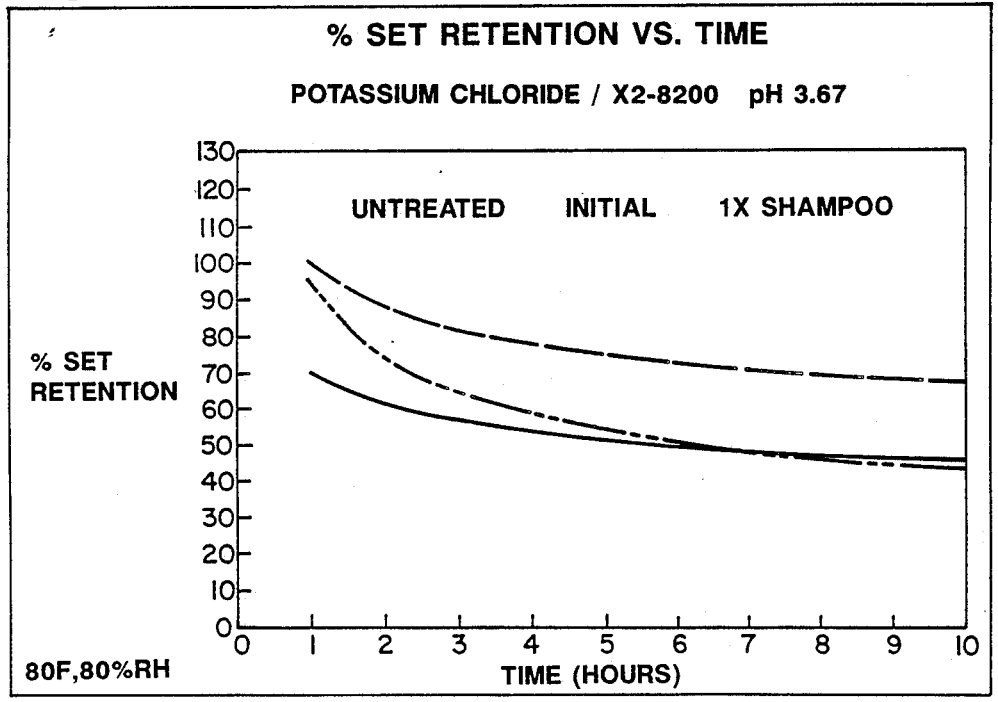

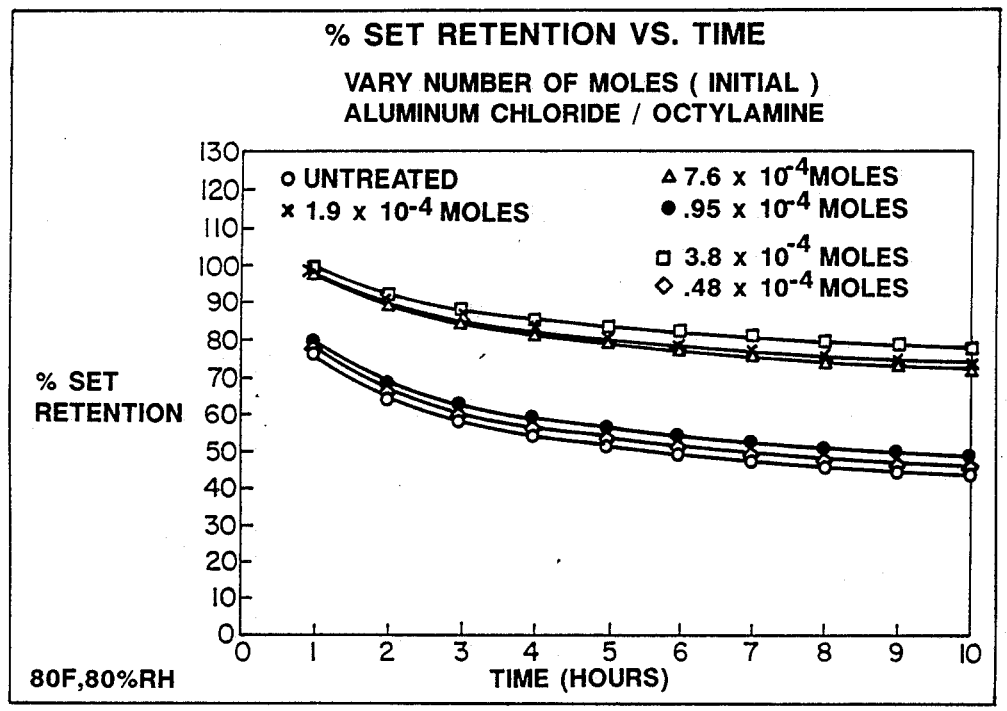
Fig. 29
Fig. 30
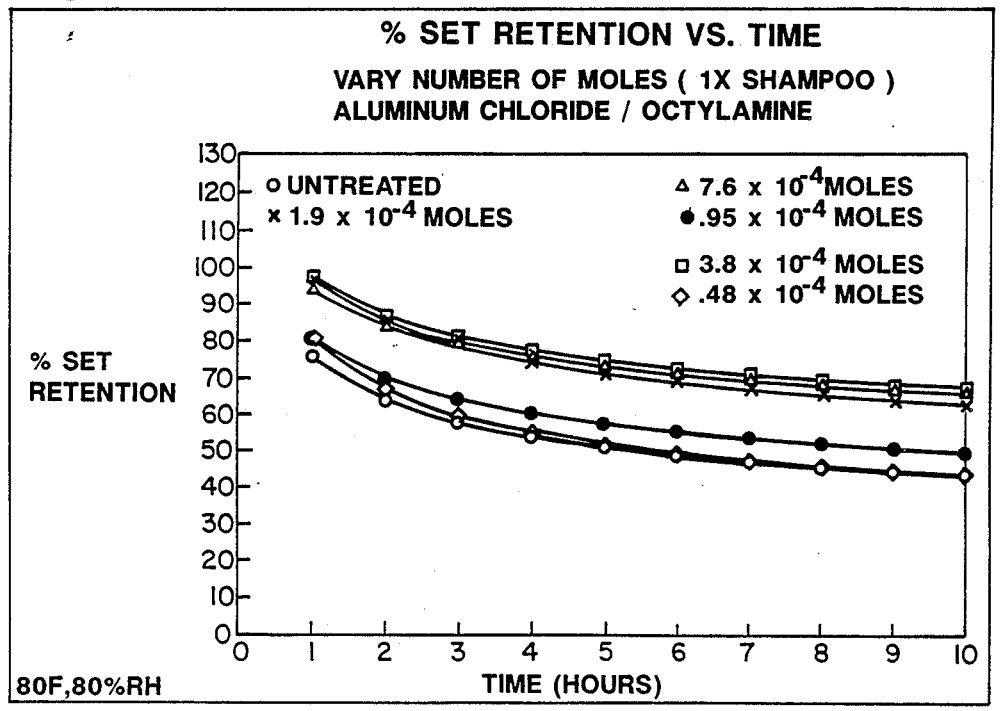

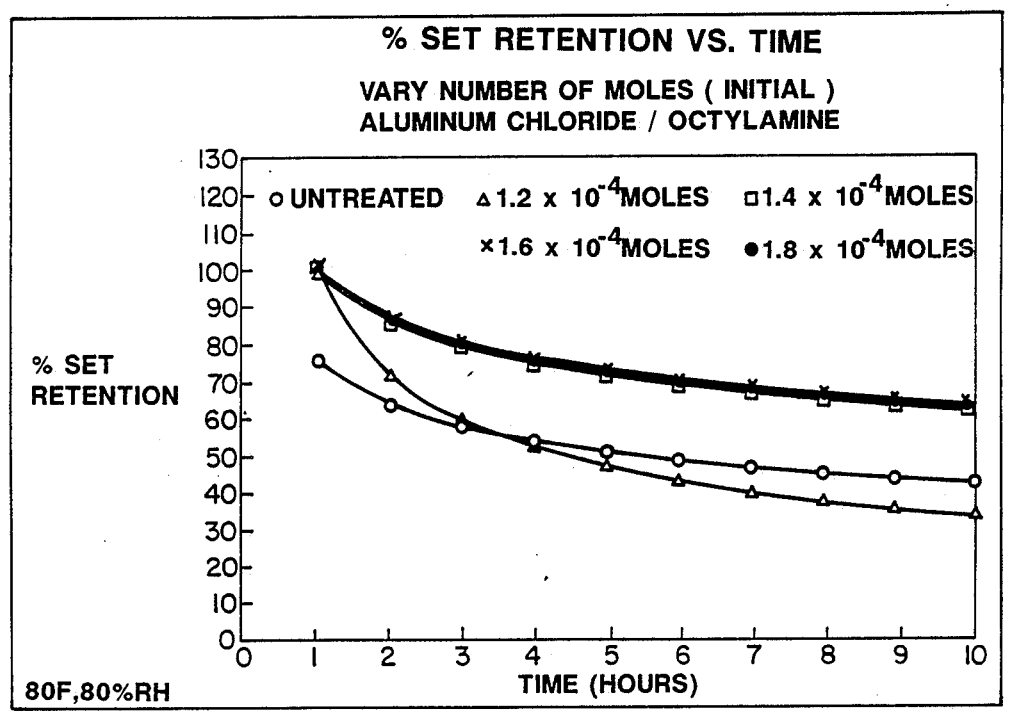
Fig. 31
Fig. 32
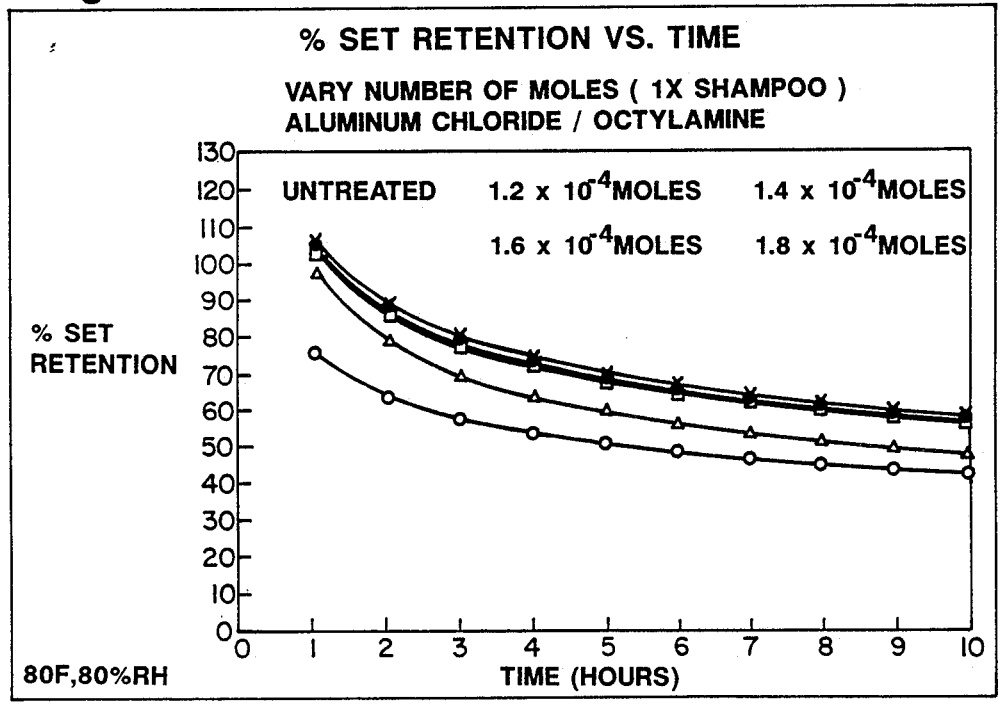

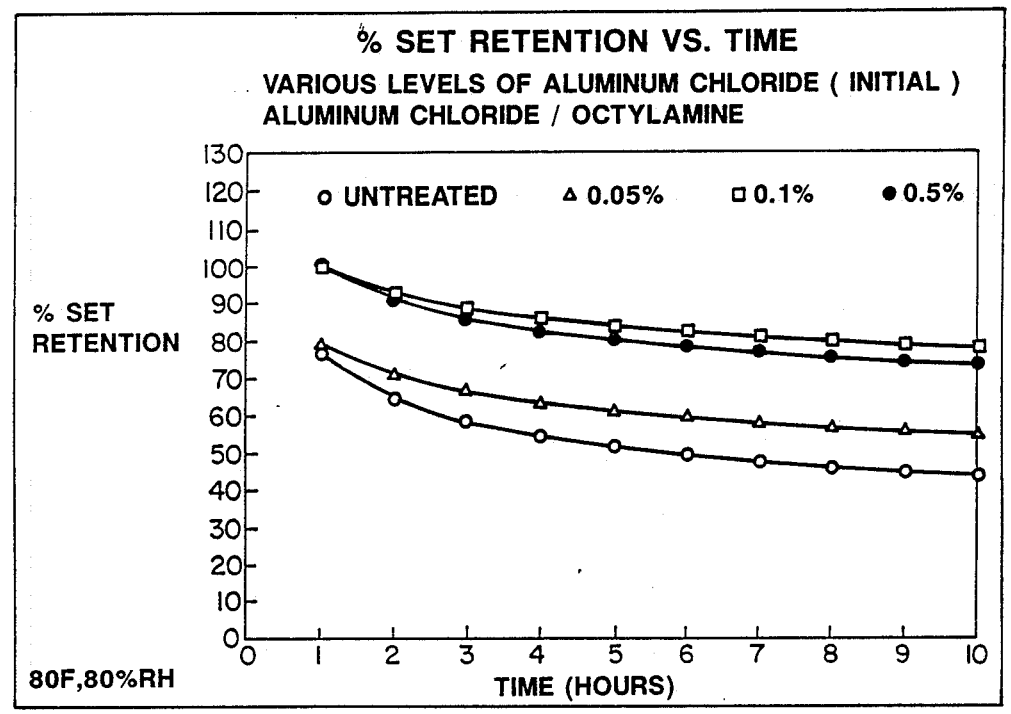
Fig. 33
Fig. 34
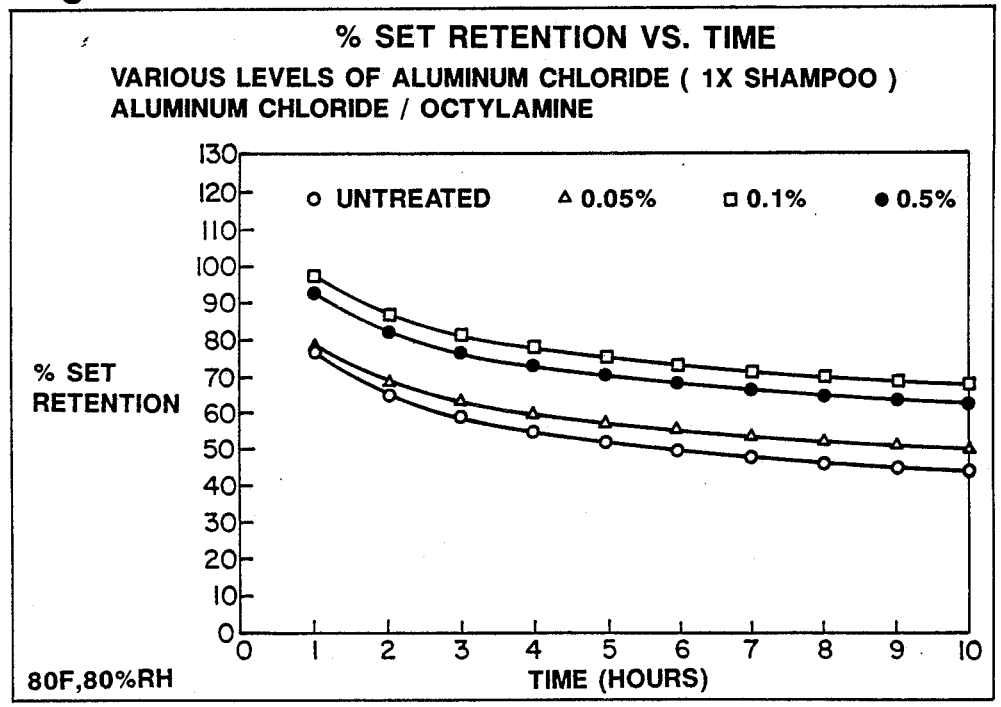

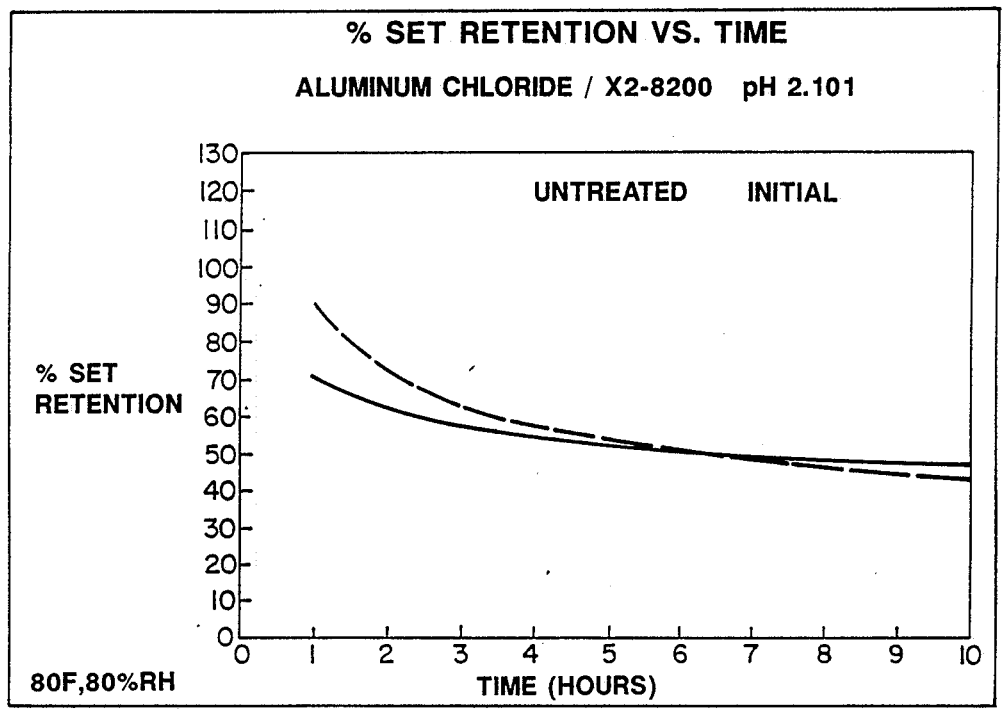
Fig. 35
Fig. 36
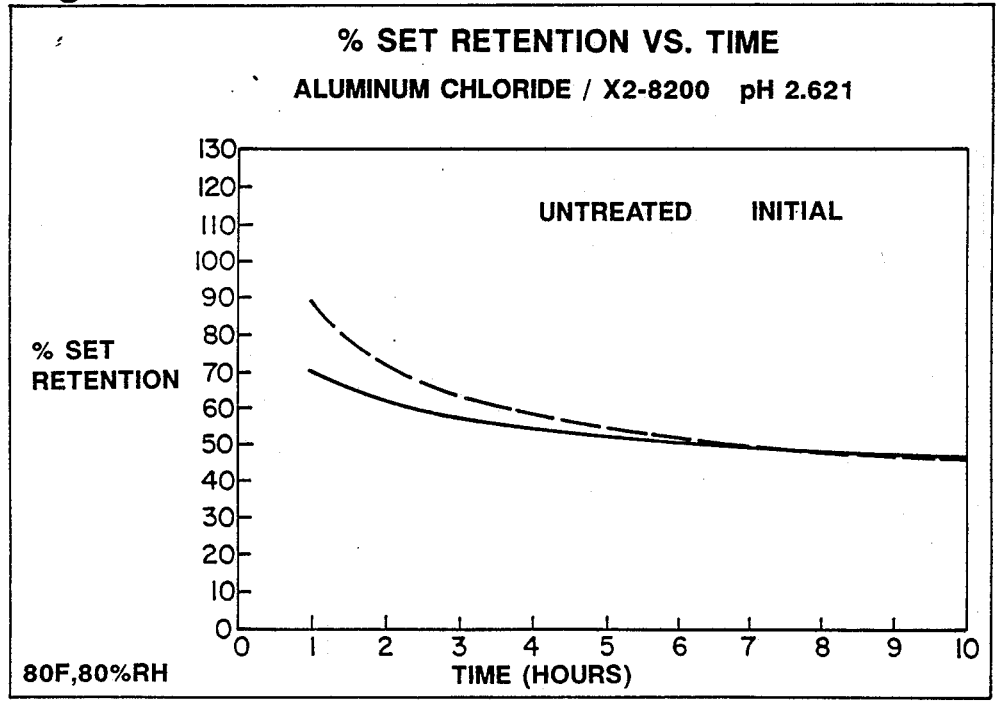

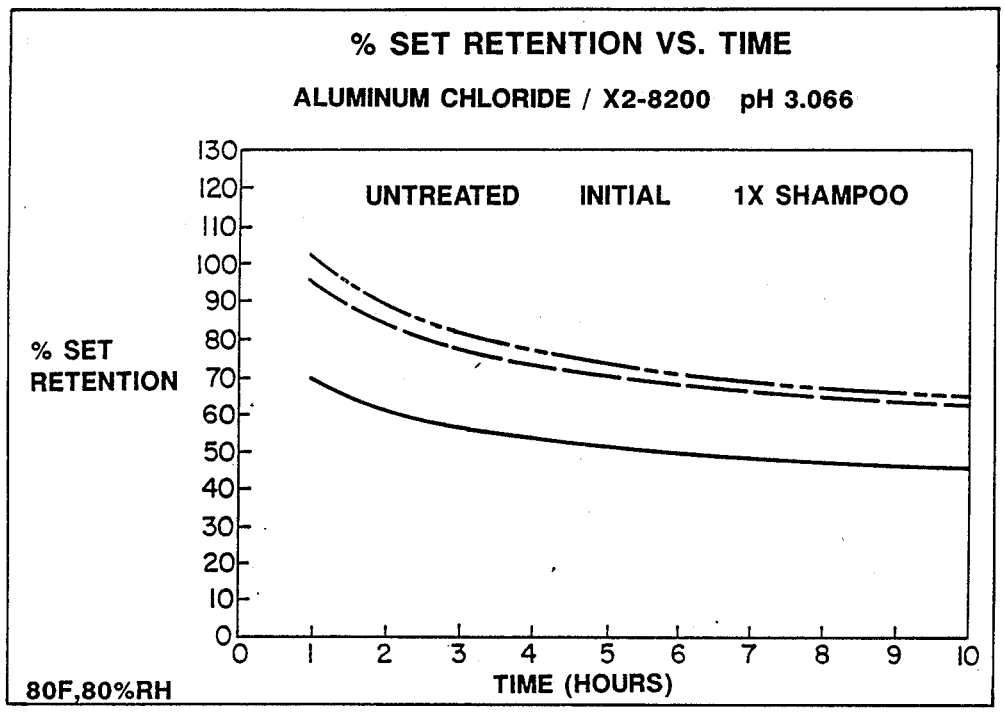
Fig. 37
Fig. 38
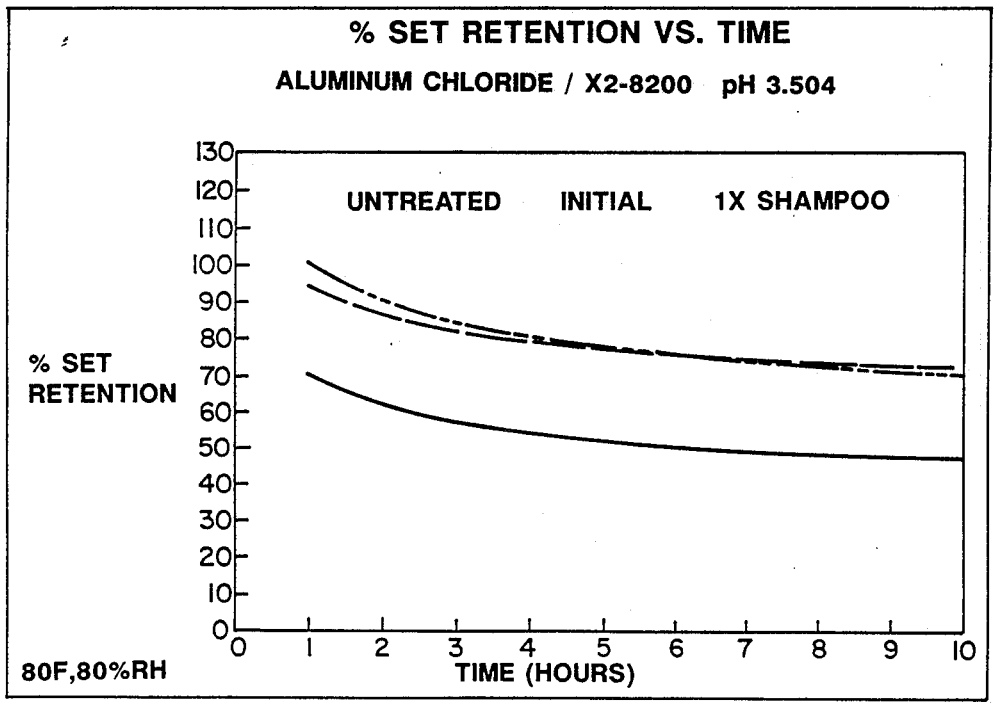

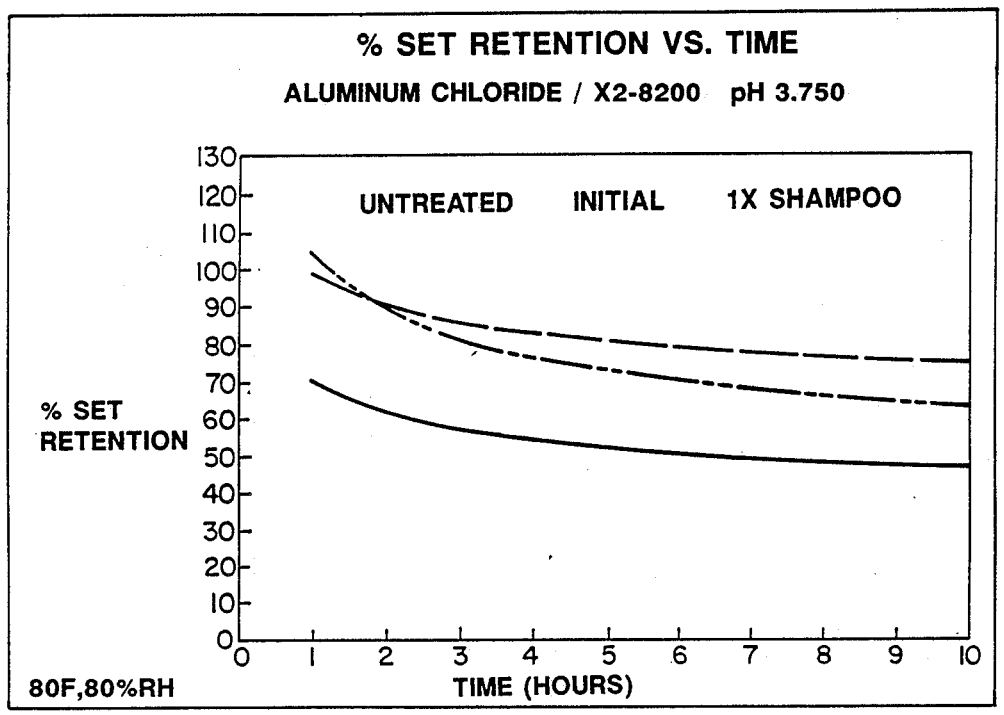
Fig. 39
Fig. 40
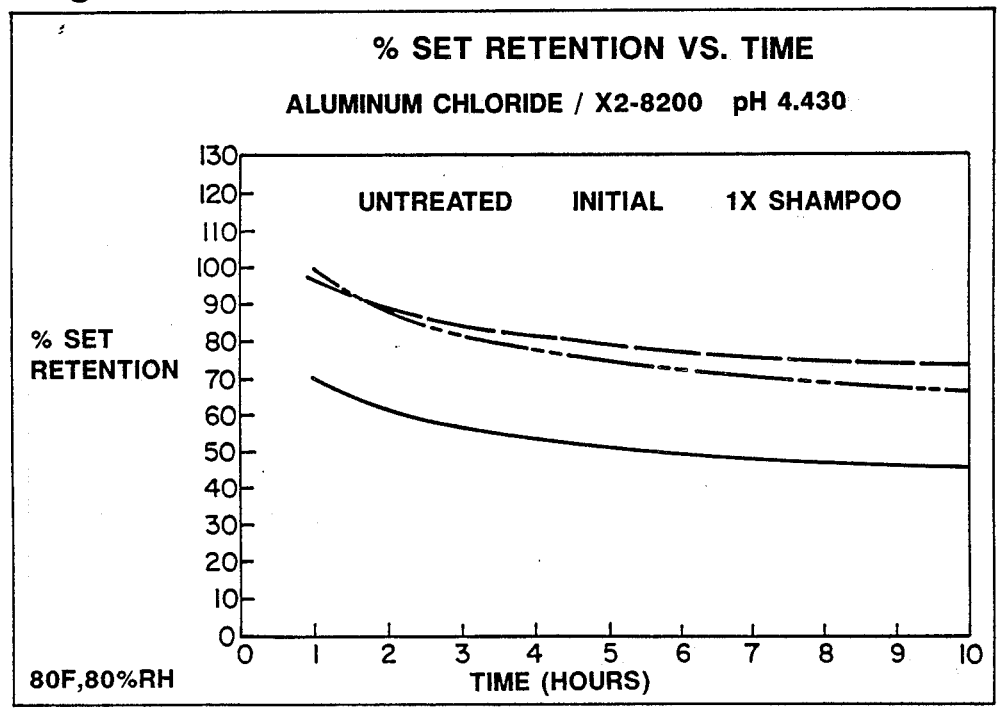

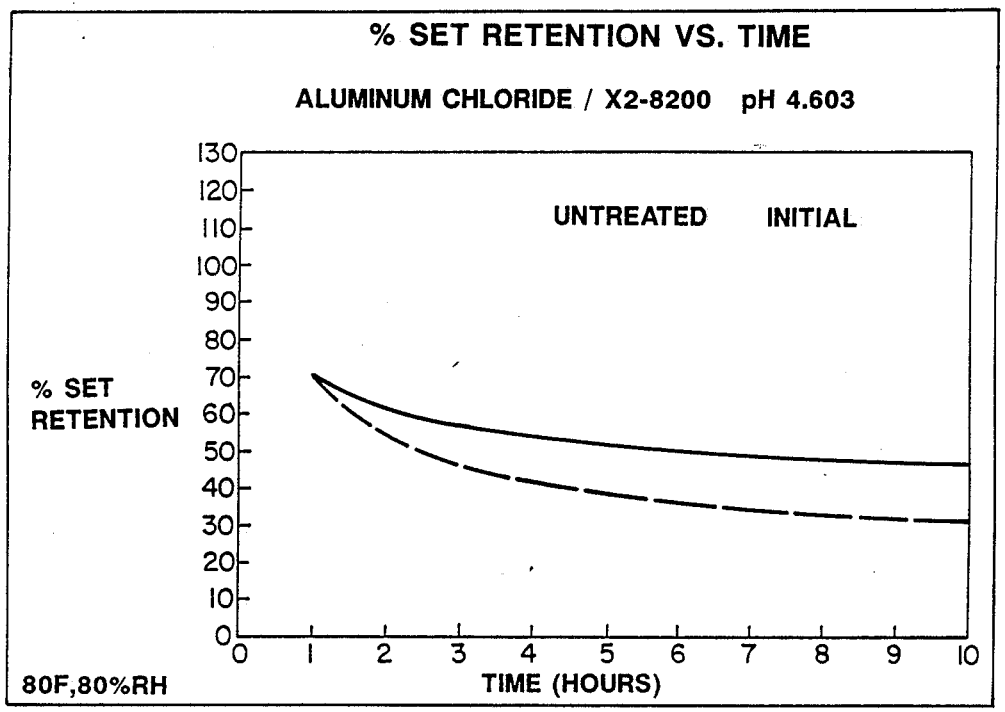
Fig. 41
Fig. 42
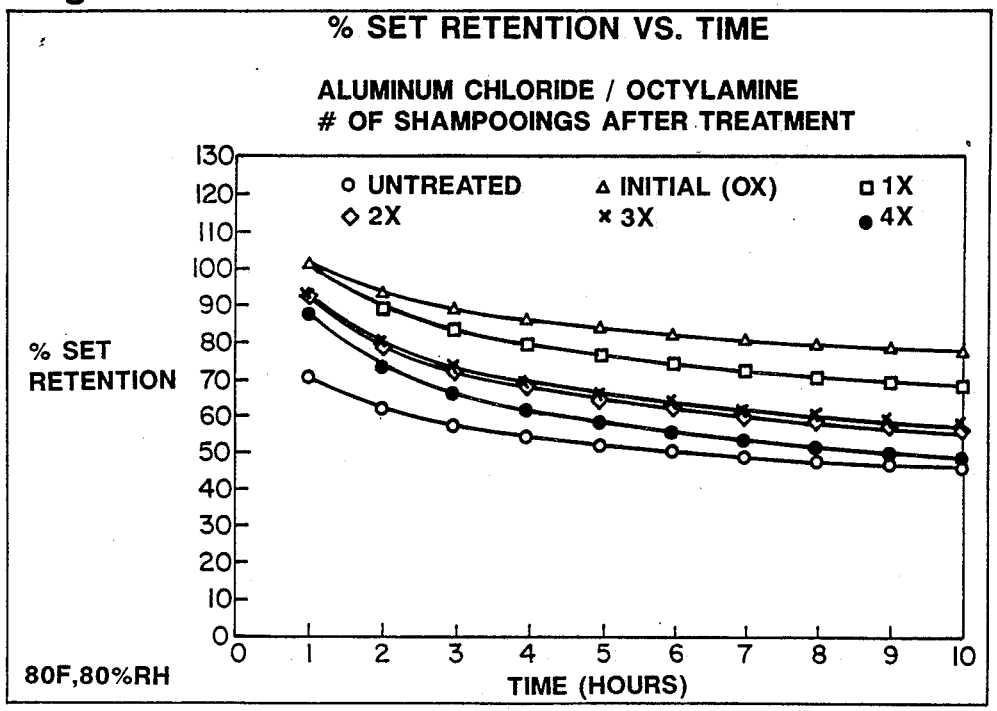

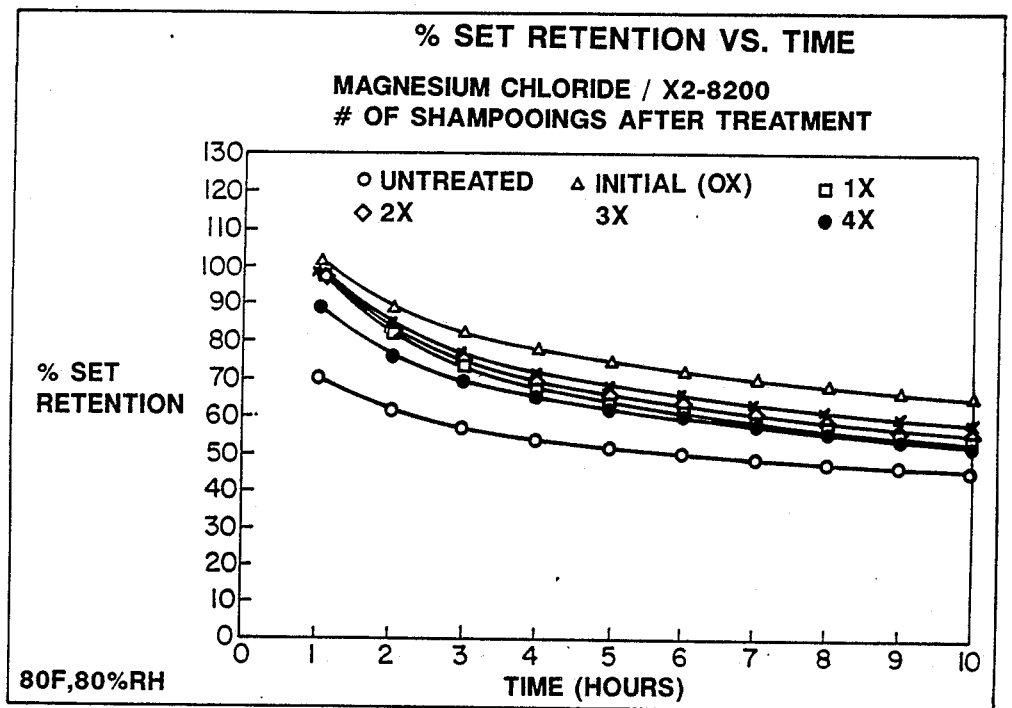
Fig. 43
Fig. 44
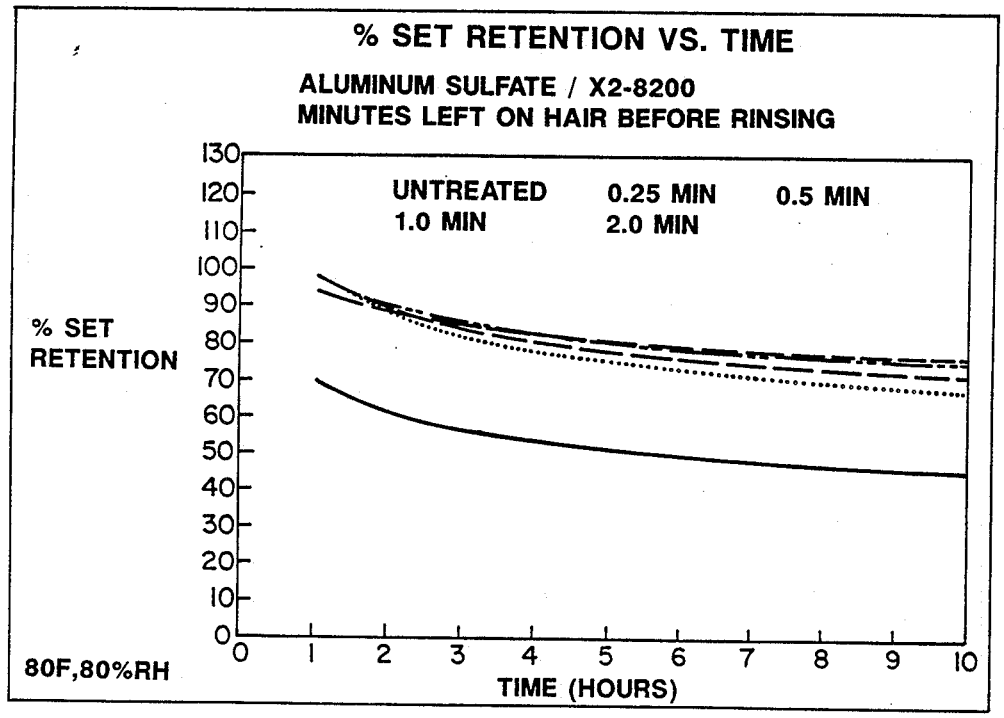

HAIR TREATMENT COMPOSITIONS TO IMPART DURABLE HAIR SET RETENTION PROPERTIES

FIELD OF THE INVENTION

The present invention relates to a hair treating composition and to a method of setting human hair that imparts unexpectedly durable hair set retention properties to human hair. More particularly, the present invention is directed to a hair treating composition including a water-insoluble amino- or substituted amino-containing compound, such as octylamine, an amino-functionalized silicone or polyethyleneimine; and an ionizable metal salt, wherein the metal has a valence of at least II, such as aluminum chloride or zinc chloride; in a molar or molar-equivalent ratio of ionizable metal salt to water-insoluble amino-containing compound of at least 1:1, and having a pH in the range of about 2.7 to about 4.5, to provide unexpectedly durable hair set retention properties after application to human hair. The composition of the present invention can be applied to the hair from an aqueous solution, aqueous spray, emulsion, conditioner, shampoo and/or other similar hair treatment products either in a single vehicle containing both the water-insoluble amino-containing compound and the ionizable metal salt, or as a two-part vehicle, wherein in one vehicle part includes the water-insoluble amino-containing compound and the second vehicle part includes the ionizable metal salt.

BACKGROUND OF THE INVENTION

Normal hair can be so fine and limp, and so lacking in body that the hair does not hold a hair set well. Furthermore, the hair can become even less bodied and can be weakened further as a result of being subjected to chemically active hair treatments, such as permanent waves and tints. Additionally, hair can be weakened even further by other contributing factors, such as bleaching by sun exposure and/or chlorinated swimming pool water.

Normal hair is usually hydrophobic. However, many of the chemically active hair treatments remove the natural hydrophobic components from the hair. As a result, as the hydrophobicity of the hair decreases, the relative porosity of the hair increases and the hair tends to absorb water and swell more readily. In such a weakened and porous state, the water-swollen hair is more vulnerable to stretching and breaking.

Since hair setting is basically the process of shaping wet hair by the steps of stretching the hair by curling the hair, fixing the hair in place by drying, then combing to give the finishing touches to provide the desired hairstyle, the overall condition of the hair is an important factor in achieving an acceptable hair set. In particular, the setting of wet hair can be accomplished by making flat curls from strands of hair and fixing the curls with hairpins to produce "pin curls". Similarly, the wet hair can be set by using any of a variety of rollers or curlers to mechanically fix the hair. In either case, the winding of the wet hair is followed by drying, either by ambient air drying, electric drying or hot air drying.

The inherent problem encountered in hair setting is the natural tendency of the hair to return to its natural shape. For example, the set hair returns to its natural shape almost immediately if moistened. Likewise, high humidity conditions accelerate the tendency of the hair to return to its natural shape. Therefore, intensive efforts have been directed toward providing a hair set with sufficient holding power to maintain the designed hair style until at least the next shampoo, and therefore giving the hair set a degree of permanency.

As shown by the natural tendency of hair to return to its natural shape, hair is an elastic structure. As a result, the slight deformations in the hair structure resulting from setting the hair are completely reversible. However, the rate of return of the hair to its natural shape is dependent upon the method used to deform, or set, the hair. Hair sets performed with wet strands of hair being rolled tightly, either in curls around the finger or on curlers, followed by drying the hair and unrolling the curlers after drying, corresponds to the release of the hair from a deformation-causing load. The deformation, or set, obtained can last for several days, but the set will not be retained if the hair is wetted.

The observations of hair deformation and relaxation are related to physical and chemical changes in the protein structure level of hair. Sufficient stretching of the hair causes partial transformation of the $\alpha$-keratin protein structure of the hair into the $\beta$-keratin protein structure of the hair. This structural transformation is accompanied by a shift in relative position of the polypeptide chains that is facilitated by water moistening the hair. The shift in position of the polypeptide chains therefore disrupts the ionic and hydrogen bonds in the hair. During the drying procedure, new ionic and hydrogen bonds are formed that block the return to the $\alpha$-keratin protein structure of hair. Gradually, the new protein linkages give way under natural forces, such that the hair returns to its original state and length. If the hair is moistened, the return to the $\alpha$-keratin form is virtually immediate.

Therefore, investigators have sought to delay the combined action of natural forces and moisture that cause the hair to return to its original state by utilizing solutions containing naturally-occurring or synthetic polymers. When applied to the hair from aqueous or aqueous/alcoholic solutions, the polymers leave a film on the hair after drying. The polymeric film promotes cohesion and gives stability to the hair set, and therefore setting lotions containing polymers have been devised to maintain the hold of the hair set. The principal objective of the setting lotion is to cover the styled hair with an invisible polymeric film that will give the styled hair a degree of rigidity and protect the hair style against wind and humidity.

Hair spray products act in a similar manner. The hair spray products are applied to wet and/or dry hair and generally are not rinsed out. Like hair setting lotions, the hair spray contains polymers, or mixtures of polymers, that remain fixed on the hair and affect the hair in various ways. For example, a "mechanical" effect is exerted on each individual hair. The film-forming polymers are used to provide a flexible sheath of polymeric film on the hair after drying, and therefore, for mechanical reasons, retard the return of each individual hair to its natural shape. In addition, the polymeric film provides an overall stiffening of the hair. The hair behaves as if the individual hair strands are welded together, and the final hairstyle has better cohesion, therefore resisting the natural forces that return the hair to its natural shape. Finally, the polymeric film protects the hair from humidity. The ability of the polymeric film to attract and absorb water is preferably minimal, such that the polymeric film retards moisture uptake by hair and retards the return of the hair to the α-keratin hair protein structure.

The general principles of hair setting are thoroughly discussed by C. Zviak, in *The Science of Hair Care*, Marcel Dekker, pp. 149–181 (1986). Zviak reviews both the polymers used in hair setting products and the formulation principles used to produce a hair set product that provides such beneficial hair set properties as improved hair style hold, easy application and combing, quick drying and non-stickiness, good hair body and bounce, increased hair volume and gloss, and hydrophobicity. It is evident that in the formulation of any end-use product, some of these benefits must be sacrificed to some degree to achieve a competing benefit. Therefore, the formulation of hair set products has proved difficult, and, as a result, hair set products have been developed in a variety of product forms.

The prior art reveals that nonionic, cationic and anionic polymers have been used in hair set products, with the anionic polymers providing the best hair set results. However, anionic polymers also have disadvantages, such as high water solubility, therefore low hydrophobicity, and low substantivity to hair fibers, therefore easy elimination from the hair by combing and brushing. As a result, investigators have continued to search for compounds and compositions that provide the benefits of an anionic surfactant-based hair set product plus an improved durability of the hair set. As previously mentioned, to overcome some of the inherent disadvantages of the polymers utilized to set the hair, hair set products are made available in diversified forms in an attempt to minimize the drawbacks of the particular polymer used in the formulation. For example, hair set products are available as plasticizing lotions, plasticizing gels, aerosol foams, all-purpose lotions, hair sprays, holding lotions, conditioners and shampoos.

Although commercially available products relying upon polymeric materials produce bodying effects on the hair, these products usually do not provide improvements in hair hydrophobicity against the known adverse effects of humidity in maintaining a hair style. In some cases, the hair treating products make the hair hard to comb or can absorb moisture themselves. One other effort to make hair hydrophobic is to apply oily hair dressings and creams to the hair, wherein the oily product is left on the hair to act as a physical barrier against moisture uptake. However, these oily products provide only a temporary barrier that is removed when the consumer washes her or his hair. In addition, these oily products frequently impart the hair with a dull and heavy coating, thereby sacrificing the bodying benefits desired by persons having fine, limp, porous hair. Consequently, in using presently available commercial products, consumers must sacrifice certain desirable physical characteristics of the hair in order to achieve or improve other desirable physical characteristics.

The present invention relates to a composition and method of treating the hair to improve the physical properties of the treated hair. It has been found that by treating the hair with compositions including a water-insoluble amino-containing compound and an ionizable metal salt, wherein the metal has a valence of at least II, the physical properties of the hair are improved such that the hair will retain the shape of the hair set and will not revert to its natural shape upon contact with moisture, and, more surprisingly, will retain the shape of the hair set even after a subsequent shampooing. Thus, the imprOVed hair set retention properties imparted to the hair upon treatment with the composition of the present invention obviates the need to treat the hair each day or after each shampooing.

Various effects resulting from treating human hair with metal salts and/or amines are known. For example, polyvalent metal salts are known in the art for their astringent and antiperspirant effects on skin. Hewitt et al, in U.S. Pat. No. 3,842,847, taught the use of astringent water-soluble salts of aluminum, hafnium, zirconium, zinc and like metals in a shampoo and hair treatment to diminish scalp perspiration. Hewitt et al also reported antistatic and anti-soiling effects on hair treated with aqueous rinses including aluminum chlorohydrate. Hewitt et al theorized that the astringent metal salt reacted with the hair keratin to reduce the anionic nature of the hair, and therefore, to reduce "fly-away" hair. However, to obtain the benefits disclosed by Hewitt et al, the hair had to be water rinsed after treatment until the pH of the rinse water was at least over 6. In contrast, to achieve the benefits of the present invention, the hair treating composition does not have to be rinsed from the hair.

Cassidy, in U.S. Pat. No. 3,208,910, disclosed the use of a water-soluble zirconium carboxylate salt in a hair styling fluid to impart body, moisture resistance and sheen to human hair. Zirconium acetate, present in a concentration of 0.1 percent to 2 percent in a composition having a pH from about 3 to about 6, was used in a treatment for setting the hair. However, the treated hair behaved as if it were full of snarls and the hair was extremely difficult to comb when the concentration of zirconium acetate exceeded 2 percent. Consequently, body-enhancing and moisture-resistant effects could be imparted only by including auxiliary dispersing agents, waxes and polymers; or by washing the hair with a soap shampoo to form an insoluble zirconium soap on the hair. However, in accordance with the present invention, the absolute concentration of the water-soluble metal salt is not limited and auxiliary agents, except for the water-insoluble amino-containing compound, are not required to produce the new and unexpected results of the present invention.

Similarly, Anzuino and Robbins, in the publication "Reactions of Metal Salts with Human Hair Containing Synthetic Polymers", *J. Soc. Cosmet. Chem.*, 22, 179–186 (1971), taught the polymerization of vinyl monomers, such as methacrylic acid or N,N-dimethylaminoethyl methacrylate, within the keratin fibers of the hair to alter the chemical reactivity of the keratin. Then the polymer-containing hair fibers were reacted with metal salts, such as calcium chloride, nickel chloride, or zinc acetate, to improve the wet load extension properties of the hair. However, the method disclosed by Anzuino and Robbins involves a chemical reduction of the hair that imparts roughness, color lightening and other undesirable properties to the hair. In contrast, the composition and method of the present invention does not involve a chemical reduction of the hair protein, and therefore is not damaging to the hair fiber.

Homan, in U.S. Pat. No. 4,487,883, disclosed the use of a polymer having at least one nitrogen-hydrogen bond and an anhydrous additive, like a titanate, zirconate, or vanadate, in a hair-treating composition. According to the teachings of Homan, after application to the hair, the polymer is crosslinked upon exposure to moisture or humidity to provide hair conditioning and a hair set. A subsequent shampooing breaks the crosslinking bond, and the polymer, now in its original form, still acts as a conditioner, but does not act as a hair set. Therefore, the hair setting properties provided by the compositions disclosed by Homan are lost as soon as the treated hair is wetted. The compositions disclosed by Homan further suffer from the disadvantage of having to be stored in an anhydrous state. Such storage conditions usually are not practically feasible because it is difficult to insure that a commercial product remains moisturefree under normal production and storage conditions. Conversely, the composition of the present invention is not limited to polymeric nitrogen-containing compounds, and the present composition has an aqueous base thereby allowing normal production conditions and a variety of formulation choices. Furthermore, a subsequent shampooing of hair treated with the composition of the present invention will not destroy the hair set properties imparted by the hair treatment.

European patent application No. 0117360 teaches the use of an aqueous composition including an emulsified polymer having at least one nitrogenhydrogen bond and an organic zirconate, germanate and/or titanate, and having a pH of 6 to 8, in a process to condition and set the hair. The method and composition disclosed in European patent application 0117360 differs from the present invention in that the European disclosure operates well outside the pH range of the present invention and, more importantly, the composition applied to the hair, as taught in the European application, does not maintain the hair set properties of the hair after a shampooing. In contrast to the present invention, wherein the hair set retention properties are retained through more than one shampooing, the composition of the European disclosure reverts to a non-crosslinked polymer after a single shampooing to act only as a hair conditioner.

In U.S. Pat. No. 4,283,384, Jacquet et al disclosed a composition including a particular type of polymer produced from an unsaturated monomer such as acrylic acid, a compound containing at least one hydroxyl functionality such as polyvinyl alcohol or pentaerythritol, and cerium ion. The polymer imparts good holding power to hair when the polymer is applied to the hair in a shampoo formulation. In the method of Jacquet, the cerium ion apparently is not involved in the interaction between hair and polymer. Initially, the effects of the Jacquet et al composition on the hair match the effects provided by the present invention. However, Jacquet et al do not disclose or suggest that their composition imparts an especially durable hair set to the hair. In contrast, the present invention exhibits unexpected durability by maintaining the desired hair set properties through at least one shampooing after treatment.

Jachowicz et al, in U.S. Pat. No. 4,588,760, disclosed applying an aqueous solution containing a heximinium salt and resorcinol to the hair such that an in situ polymerization reaction occurs to improve hair set retention properties. However, to provide the benefits of improved hair set retention, the composition of Jachowicz et al must contact the hair for a period of time ranging from 0.25 hours to 16 hours. Surprisingly, the method and composition of the present invention unexpectedly impart excellent hair set retention characteristics to the hair within 2 minutes, generally the time required to comb the composition through the hair. U.S. Pat. No. 4,588,760 taught that the quaternary ammonium halide salts of hexamethylene tetramine undergo complexing and polymerization with resorcinol within the hair fibers to form a condensation polymer. Overall, the method of Jachowicz is time-consuming and complicated, and uses potentially toxic materials, especially in comparison to the composition and the method of the present invention.

In U.S. Pat. No. 4,614,200, Hsiung et al disclosed utilizing an aqueous aluminum salt solution, without an amino-containing compound, to improve the set retention properties of hair at an ambient relative humidity of 50–60%. However, unlike the composition of the present invention, at higher relative humidities of approximately 80%, aluminum chloride solutions without amino-containing compounds exhibit poor set retention properties. Furthermore, the method of Hsiung et al specifically excludes using certain metal salts, such as zinc salts, that have provided excellent hair set retention results in accordance with the present invention. For example, a composition including zinc chloride and an amino-functionalized silicone provided excellent hair set retention properties in accordance with the composition and method of the present invention.

Accordingly, to date, the compositions and methods used to set hair have suffered from poor set retention times, from sacrificing one beneficial hair property in order to achieve another beneficial hair property, and/or from abnormally long times to treat the hair. Prior to the present invention, no known method or composition has been employed to effectively treat hair within a few minutes to provide a durable hair set that is preserved through at least one shampooing subsequent to the hair setting treatment.

Therefore, in accordance with the present invention, hair setting treatments are surprisingly and unexpectedly improved by contacting the hair with a composition including a water-insoluble amino-containing compound and an ionizable metal salt, wherein the metal has a valence of at least II. The water-insoluble amino-containing compound and the ionizable metal salt can be applied to the hair from an aqueous or aqueous/alcoholic vehicle at ambient temperature and is allowed to contact the hair for relatively short times to provide the benefits and advantages of the present invention. Therefore, as will be demonstrated more fully hereinafter, the method and composition of the present invention provides an aesthetically pleasing hair set that does not damage the hair and is durable through at least three subsequent shampooings.

SUMMARY OF THE INVENTION

In brief, the present invention relates to a composition and method of treating human hair. More particularly, the present invention relates to a method of treating the hair, whereby contacting the hair with a composition including a water-insoluble amino-containing compound and an ionizable metal salt, wherein the metal has a valence of at least II, provides a durable hair set that maintains and/or improves the physical characteristics of the hair, such as gloss, combability, softness, and body. Surprisingly and unexpectedly, human hair treated with the composition of the present invention exhibits improved hair set retention properties, such that the hair can be shampooed at least three times after application of the hair treating composition without having to reapply the hair treating composition before styling the hair.

Therefore, it is an object of the present invention to provide a hair treating composition.

It is also an object of the present invention to provide an aqueous hair treating composition comprising a water-insoluble amino-containing compound and an ionizable metal salt, wherein the metal salt has a valence of at least II.

Another object of the present invention is to provide a hair treating composition having a pH in the range of about 2.7 to about 4.5, and having the molar quantity of the ionizable metal salt equal to or greater than the molar, or molar-equivalent, quantity of the amino-containing compound.

Another object of the present invention is to provide a method of treating human hair with a hair treating composition to achieve improved hair set retention properties.

Another object of the present invention is to provide a method of treating human hair by contacting the hair with a composition having a pH of between about 2.7 and about 4.5 and including a water-insoluble compound having at least one amino-functionality and an ionizable metal salt, wherein the metal has a valence of II or greater, at ambient temperature for relatively short contact times to achieve a hair set having sufficient durability to withstand at least one hair shampooing.

Another object of the present invention is to provide a method of treating human hair to yield durable hair sets by treating the hair with a single package, single vehicle composition including both the amino-containing compound and the ionizable metal salt; or by treating the hair with a two package, two vehicle composition, wherein one vehicle includes the amino-containing compound and the second vehicle includes the ionizable metal salt.

Still another object of the present invention is to provide a method of treating the hair to yield durable hair sets by contacting the hair with an aqueous spray, aqueous solution, aqueous emulsion and/or aqueous shampoo to treat the hair in either a rinse-off or leave-on method.

BRIEF DESCRIPTION OF THE DRAWINGS

The above and other objects and advantages and novel features of the present invention will become apparent from the following detailed description of the preferred embodiments of the invention illustrated in the accompanying figures illustrating the enhanced hair set retention properties achieved by using the method and composition of the present invention, wherein:

FIG. 1 is a graph comparing % set retention vs. time for untreated hair, % set retention vs. time for hair treated only with an amino-functionalized silicone, and % set retention vs. time for hair treated only with aluminum chloride;

FIGS. 2 through 20 is a series of graphs showing % set retention of hair vs. time for hair treated with hair setting compositions including aluminum chloride as the ionizable metal salt and having a pH of approximately 3.51 to approximately 3.80. Each of the FIGS. 2 through 20 shows the effect upon the hair set retention properties of varying the amino-containing compound in a hair treating composition including aluminum chloride. The hair set retention properties are summarized hereinafter in Table II. Each of the FIGS. 2 through 20 compares the % set retention vs. time for hair treated with the composition including aluminum chloride and amino-containing compound to % set retention vs. time for untreated hair and to % set retention vs. time for hair treated with the aluminum chloride and amino-containing compound composition and subjected to one hair shampooing;

FIGS. 21 through 28 is a series of graphs showing % set retention of hair vs. time for hair treated with hair setting compositions including an amino-functionalized silicone as the amino-containing compound and having a pH of approximately 3.50 to approximately 3.95. Each of FIG. 2 and FIGS. 21 through 28 shows the effect upon the hair retention properties of varying the ionizable metal salt in a hair treating composition including the amino-functionalized silicone. The hair retention properties are summarized in Table III. Each of FIG. 2 and FIGS. 21 through 28 compares the % set retention vs. time for hair treated with the composition including the metal salt and amino-functionalized silicone to % set retention vs. time for untreated hair and to % set retention vs. time for hair treated with the metal salt and amino-functionalized silicone composition and subjected to one hair shampooing;

FIGS. 29 through 32 are graphs showing % set retention of hair vs. time for hair treated with hair setting compositions including octylamine as the amino-containing compound and aluminum chloride as the ionizable metal salt. FIGS. 29 through 32 show the effect of decreasing the amount of octylamine and aluminum chloride in the hair setting composition to a level wherein the benefits and advantages of the present invention cannot be realized. The hair retention properties are summarized in Table IV. FIGS. 29 and 31 demonstrate the effect of lowering the octylamine and aluminum chloride concentrations before shampooing, and FIGS. 30 and 32 demonstrate the effect after one hair shampooing;

FIGS. 33 and 34 are graphs showing % set retention vs. time for hair treated with compositions including octylamine and varying amounts of aluminum chloride to show that the ionizable metal salt must be present in an equal molar, or equal molar equivalent, to the water-insoluble amino-containing compound;

FIGS. 35 through 41 is a series of graphs showing % set retention vs. time for hair treated with compositions including an amino-functionalized silicone as the amino-containing compound and aluminum chloride as the ionizable metal salt. Each of FIGS. 35 through 41 shows the effect upon the hair retention properties of varying the pH of the hair treating composition from approximately 2.10 to approximately 4.60. The hair set retention properties are summarized in Table VI. Each of FIGS. 35 through 41 compares the % set retention vs. time for hair treated with the hair set composition at a particular pH to % set retention vs. time for untreated hair and to % set retention vs. time for hair treated with the hair treatment composition at a particular pH and subjected to one hair shampooing;

FIGS. 42 and 43 are graphs showing % set retention vs. time for hair treated with either a composition including octylamine as the amino-containing compound and aluminum chloride as the ionizable metal salt (FIG. 42) or a composition including an amino-functionalized silicone as the amino-containing compound and magnesium chloride as the ionizable metal salt (FIG. 43). Both FIGS. 42 and 43 show the effect of subsequent shampooings on the hair set retention properties of the treated hair. The hair set retention properties graphed in FIGS. 42 and 43 are summarized in Tables VII and VIII;

FIG. 44 is a graph showing % set retention vs. time for hair treated with a composition including an amino-functionalized silicone and aluminum sulfate for varying lengths of time. The hair set retention properties are summarized in Table IX.

DETAILED DESCRIPTION OF THE PREFERRED EMBODIMENT

Figure 5:
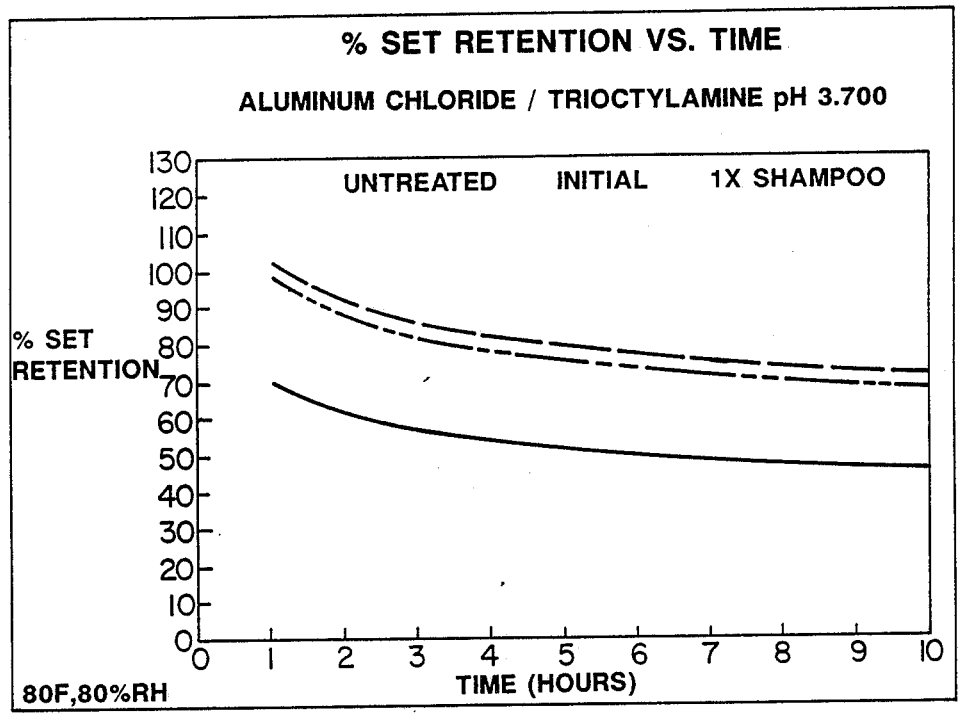
Figure 6:
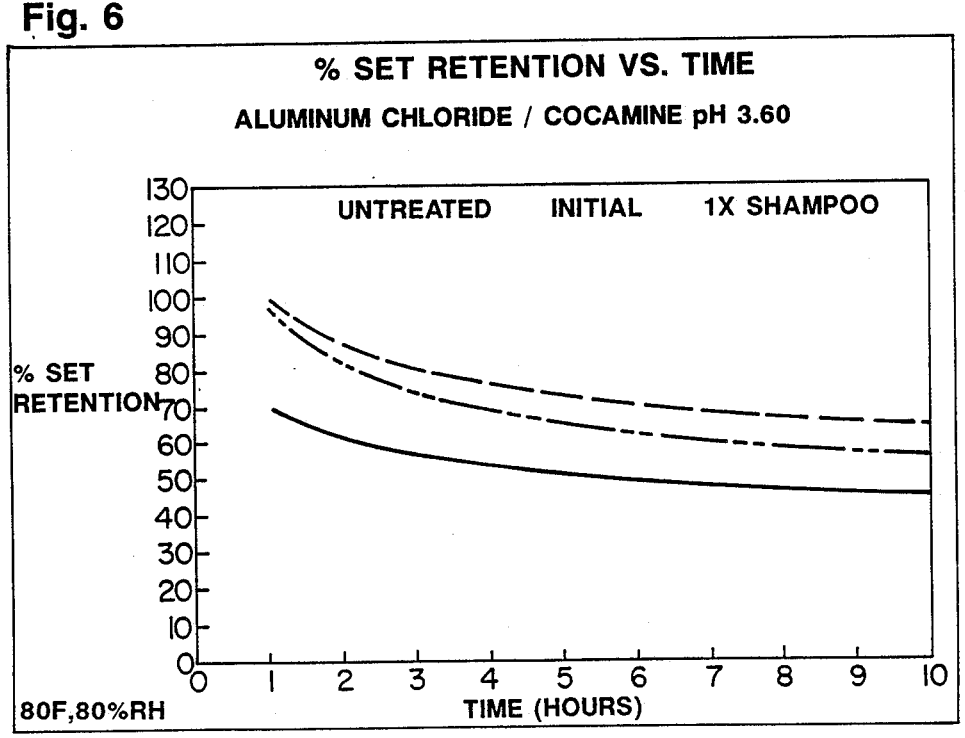
Figure 23:
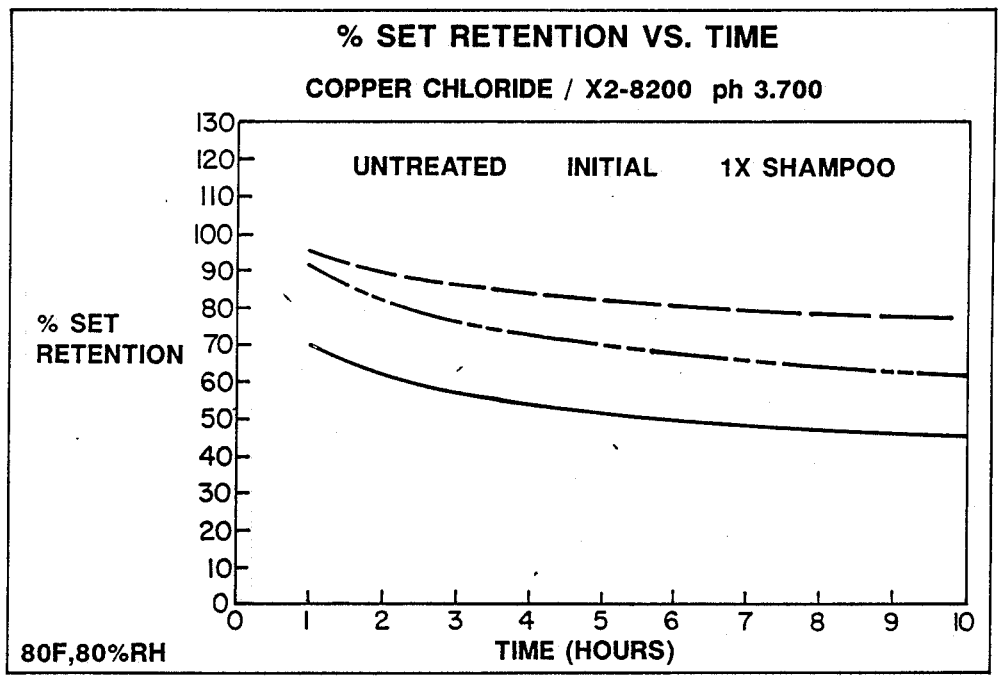
Figure 24:
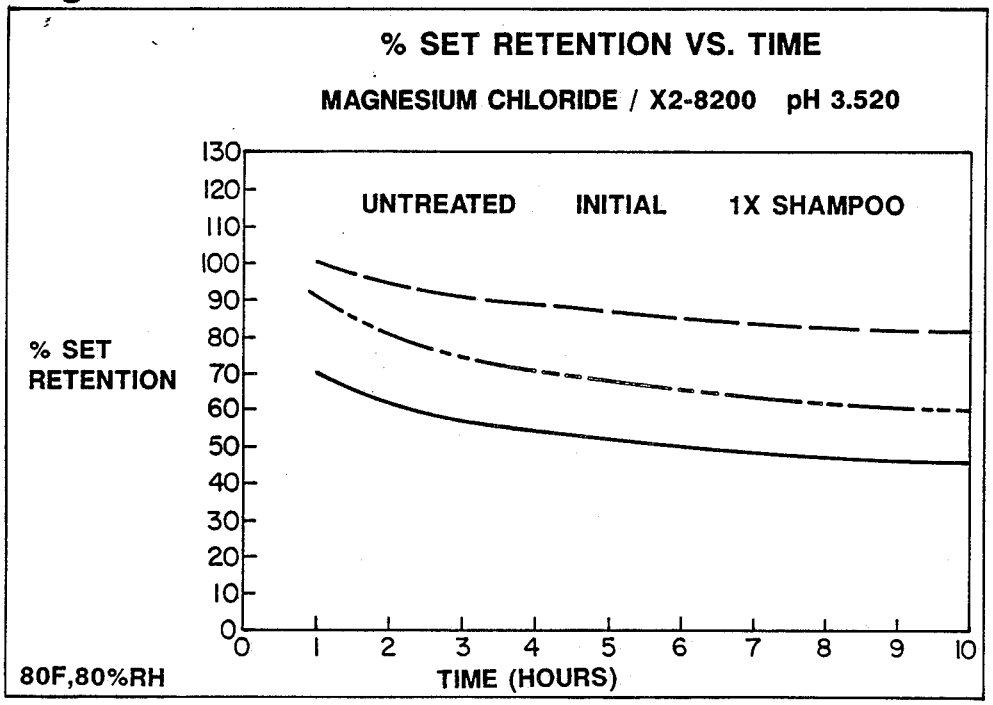

The hair treatment composition of the present invention comprises a water-insoluble amino-containing compound and an ionizable metal salt, wherein the metal has a valence of at least II; and has a pH of about 2.7 to about 4.5.

The water-insoluble amino-containing compound employed in the composition of the present invention can be a primary, secondary, or tertiary amine, having the structural formulas $R_1NH_2$, $R_1R_2NH$ and/or $R_1R_2R_3N$, wherein $R_1$, $R_2$ and $R_3$ can be the same or different alkyl or substituted alkyl moiety, or group, of sufficient carbon chain length and/or carbon content to render the amine water-insoluble. The water insoluble amino-containing compound also can be a polymeric compound that contains at least one amino-functionality, such as —NH— or —NR—. In either case, the amino-containing compound contains at least one alkyl group, or substituted alkyl group, such as a silicon-containing alkyl group, of sufficient carbon chain length and/or carbon content to render the amino-containing compound water-insoluble.

As used here and hereinafter, the term water-insoluble amino-containing compound refers to amino-containing compounds that are essentially completely water-insoluble and to amino-containing compounds that have a water-solubility of about 0.5 g or less of amino-containing compound per 100 ml of water. It has been found that incorporating amino-containing compounds possessing a greater degree of water solubility into compositions of the present invention have not provided the durable hair set properties afforded by compositions employing a water-insoluble amino-containing compound. Generally, for a primary amine, a carbon chain length of at least five carbon atoms provides sufficient water-insolubility for the amine to impart durable hair set properties to the hair when the amine is incorporated into the composition of the present invention. Similarly, for secondary and tertiary amines, as long as at least one alkyl or substituted alkyl group of the amine contains a carbon chain of at least five carbon atoms, or contains a sufficient number of carbon atoms in total, or contains a carbon and silicone chain of at least five carbon and silicone atoms in total, the secondary or tertiary amine is sufficiently water-insoluble to be employed in the composition of the present invention. Likewise, a water-insoluble polymer that contains at least one amino-functionality can be used in place of, or in combination with, the water-insoluble primary, secondary or tertiary amine, as long as the water solubility of the amino-containing polymer is about 0.5 g or less per 100 ml of water. For example, a water-insoluble ethoxylated amine can be used as the water-insoluble amino-containing polymer in the composition of the present invention.

In addition, amino-functionalized silicones, such as trimethylsilylamodimethicone, illustrated as general structure I, possess sufficient water-insolubility to be used in the composition of the present invention. Other amino-functionalized silicones that can be used in the composition of the present invention include X2-8200, X2-8107, Q2-8220 and X2-8230, all available from Dow Corning Corp., Midland, Mich.

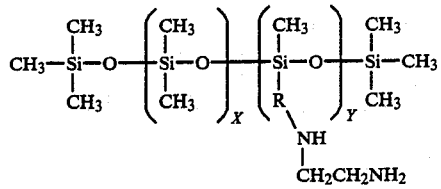

wherein X+Y is a number from about 50 to about 500, and the mole % amine functionality varies from about 1% to about 5%, and wherein R is an alkyl group having from 2 to 5 carbon atoms.

Further, in order to ensure that the amine, amino-functionalized silicone, or polymer containing amino-functionalities is sufficiently water-insoluble, no other hydrophilic functionalities, such as hydroxy, carbonyl, sulfhydryl, and/or similar hydrophilic groups should be present in the amino-containing compound in only limited amounts. As will be shown in more detail hereinafter, water-soluble quaternary ammonium salts and water-soluble amines, such as monoethanolamine and triethanolamine, do not provide the advantages and benefits of improved hair set retention properties that are provided by compositions of the present invention including a water-insoluble amino-containing compound. In addition to increasing the water solubility of the amino-containing compounds, the hydrophilic functionalities, such as quaternary ammonium and carbonyl, also reduce the basicity of the amino-containing compounds by inductive and/or resonance effects thereby reducing the ability of the amino-containing compound to coordinate with the metal ions of the ionizable metal salt after application to the hair. Furthermore, because quaternary ammonium chlorides are substantive to the hair, the hair then is unavailable to coordinate with the metal ion of the ionizable metal salt included in the composition of the present invention.

Therefore, it has been found that particularly advantageous amines, amino-functionalized silicones and/or amino-group containing polymers have at least one amino functionality and at least one carbon, or carbon-silicon, chain of five atoms or longer. Examples of suitable amines, amino-containing silicones and amino-containing polymers include octylamine, dioctylamine, trioctylamine, dimethyloctylamine, trimethyl-silylamodimethicone, water-insoluble polyethylenimines, pentylamine, dipentylamine, hexylamine, dihexylamine, trihexylamine, tripropylamine, heptylamine, dodecylamine, hexadecylamine, octadecylamine, tallow amine, hydrogenated tallow amine, dihydrogenated tallow amine, trihydrogenated tallow amine, oleyl amine, soya amine, cocamine, dicocamine, methyl dicocamine, dimethylcocamine, dimethyldodecylamine, dimethyltetradecylamine, dimethylhexadecylamine, dimethyltallowamine, dimethyloleylamine, dimethylsoyamine, tridodecylamine, and methyl stearylamine; or mixtures thereof. To achieve the full advantage of the present invention, octylamine, pentylamine, dipentylamine, trimethylsilylamodimethicone, dioctylamine, trioctylamine, tripropylamine, cocamine, hydrogenated tallow amine, dihydrogenated tallow amine, trihydrogenated tallow amine, or water-insoluble ethoxylated amine; or mixtures thereof, are combined with a suitable ionizable metal salt to provide the composition of the present invention.

As previously stated, the hair treating composition of the present invention also includes an ionizable metal salt, wherein the metal has a valence of at least II. It has been demonstrated that combining a suitable ionizable metal salt with a water-insoluble amino-containing compound provides a composition that, upon contacting human hair, surprisingly and unexpectedly increases the hair set retention properties of the treated hair. The ionizable metal salt utilized in the present invention is limited only in that it must be capable of sufficient ionization in water, or therefore possesses a sufficient degree of water solubility; and in that the metal has a valence of at least II. It also should be understood, that in particular circumstances, a particular ionizable metal salt may or may not be suitable for use in the present invention because the inherent color of the ionizable metal salt may yield an esthetically unsuitable hair treating composition.

It has been found that an ionizable metal salt of metals having a valence of at least II can be used in the composition of the present invention, thereby precluding the use of the alkali metal salts. However, ionizable salts of the alkaline earth metals, such as magnesium, calcium and barium, have a valence of II and therefore can be used alone or in combination in the composition of the present invention. Similarly, ionizable salts of aluminum, titanium, vanadium, manganese, mercury, cadmium, lead, iron, cobalt, nickel, silver, copper, cerium, hafnium, germanium, zinc and zirconium, or combinations thereof, are suitable for use in the present invention. In addition, any other ionizable metal salt, wherein the metal has a valence of at least II, can be used alone or in combination with the above-mentioned metals.

The anion of the ionizable metal salt can be any anionic moiety, either organic or inorganic in chemical structure, that permits or facilitates ionization of the ionizable metal salt in aqueous solution. The principal importance of the anion is to control release of the metal cation through ionization, and therefore, the anion can be any of the halides, such as bromide or chloride; sulfate; nitrate; phosphate; acetate; lactate; or like organic and/or inorganic anions that easily dissociate and will not react with the hair or other composition components. As will be discussed more fully hereinafter, because the composition of the present invention must be maintained at an acidic pH, anions such as hydroxyl, carbonate and bicarbonate may not be suitable as the anion of the ionizable metal salt.

The ionizable metal salts of metals having a valence of at least two that have demonstrated the unexpected ability to improve the hair set retention properties of human hair include aluminum chloride, aluminum sulfate, aluminum lactate, calcium sulfate, cupric chloride, magnesium chloride, zinc chloride and ferric chloride. Furthermore, in order to achieve the benefits and improvements afforded by the method and composition of the present invention, it has been found that the molar quantity of the ionizable metal salt, or metal salts, utilized in the composition of the present invention must be equal to or greater than the molar, or molar-equivalent, quantity of the water-insoluble amino-containing compound used in the composition of the present invention.

The percentage amount of the water-insoluble amino-containing compound and ionizable metal salt in the hair treating composition is limited only by the requirement that the molar amount of the metal salt equal or exceed the molar or molar equivalent amount of the amino-containing compound, by the amount of each component that can be incorporated into the composition by solubilization and/or emulsification, by the esthetics of the composition, and by the type of commercial product desired, such as a hair shampoo, hair conditioner, or hair set lotion. An excess amount of the amino-containing compound and/or the ionizable metal salt included in the hair treating composition does not adversely affect the hair. However, the amount of amino-compound and ionizable metal salt that is substantive to the hair is finite, therefore excess amounts of amino-compound and/or metal salt are rinsed away during hair treatment and as a result are wasted. Therefore, it has been found that the upper limit for the amino-compound and the metal salt present in the hair treating composition to provide maximum hair set benefits without wasting composition components is about $3.8 \times 10^{-4}$ moles of elemental nitrogen and about $3.8 \times 10^{-4}$ moles of metal ion. Similarly, it has been found that in order to achieve the advantages and benefits of the present invention, the lower limit for the amino-compound and the metal salt present in the hair treating composition is about $0.95 \times 10^{-4}$ moles of elemental nitrogen and about $0.95 \times 10^{-4}$ moles of metal ion.

It also has been demonstrated that regardless of the percentage amount of the ionizable metal salt and amino-containing compound in the hair treating composition, the composition must have a pH in the range of about 2.7 to about 4.5 in order to achieve the benefits and advantages of the present invention. At pH values appreciably below 2.7, the hair itself may become protonated and therefore unavailable for treatment by the composition of the present invention. Similarly, at too low a pH, the amino-containing compound can become protonated, thereby converting the amino-group to a quaternary ammonium group that is no longer capable of coordinating with the metal ion. In addition, at pH values appreciably above 4.5 the stability of the composition is diminished and precipitation occurs after relatively short storage times. Furthermore, it has been found that regardless of the type of hair tested, such as virgin brown hair, 50% gray hair, bleached blond hair and permanent waved hair, that compositions having a pH appreciably above 4.5 did not provide the advantages and benefits of the durable hair set retention properties of the present invention.

Other common cosmetic additives can be incorporated with the essential ingredients of the present invention, as long as the basic properties of the hair setting composition are not adversely affected. These additives include, but are not limited to, commonly used fragrances, dyes, opacifiers, pearlescing agents, foam stabilizers, preservatives, water softening agents, acids, bases, buffers and the like; and will usually be present in weight percentages of less than about 1% each, and about 2% to about 5% in total. Sequestering agents should be avoided to preclude a reaction between the metal ion and sequestering agent, thereby making the metal ion unavailable to treat the hair. The composition vehicle is predominantly water but organic solvents also can be added to the composition in order to solubilize compounds that are not sufficently soluble in water.

Suitable solvents include those that do not react with the ionizable metal salt or the amino-containing compound such as the lower alcohols like ethanol and isopropanol; polyols like glycerol; glycols or glycol ethers, like 2-butoxyethanol, ethylene glycol, ethylene glycol monoethyl ether, propylene glycol and diethylene glycol monomethyl ether; and mixtures thereof. These solvents can be present in the hair setting composition of the present invention in an amount from about 1% to about 75% by weight and in particular from about 5% to about 50% by weight, relative to the total weight of the composition.

The compositions can be thickened, for example, with sodium alginate, gum arabic, cellulose derivatives such as methylcellulose, hydroxyethylcellulose, hydroxypropylmethylcellulose and carboxymethylcellulose, and various polymeric thickeners, such as acrylic acid derivatives. It is also possible to use inorganic thickeners such as bentonite. These thickeners are preferably present in an amount from about 0.1% to about 10% by weight and in particular from about 0.5% to about 3% by weight, relative to the total weight of the composition.

The compositions also can include anionic, amphoteric or nonionic surfactants, to impart cleansing and/or emulsifying properties to the composition. Likewise, the compositions can contain other emulsifiers, fatty alcohols, humectants and similar materials to provide conditioning properties, aesthetic properties and desirable physical properties to the composition.

For example, representative nonionic surfactants include esters of polyols and sugars; the polyethoxylated and/or polypropoxylated alkylphenols; the polyhydroxylated polyethers of fatty alcohols; and the condensation products of ethylene oxide with long chain mercaptans or long chain amides. Similarly, representative anionic surfactants include alkali metal salts, ammonium salts or salts of amines or amino alcohols of fatty acids such as oleic acid; of the sulfates of fatty alcohols, principally $C_{12}$–$C_{14}$ and $C_{16}$ fatty alcohols; of the sulfates of polyethoxylated fatty alcohols; the alkylbenzenesulfonates, such as those wherein the alkyl moiety has 12 carbon atoms; or the alkylarylpolyether sulfates and monoglyceride sulfates. All these nonionic and anionic surfactants, as well as numerous others not cited here, are well known in the art and are fully described in the literature.

In accordance with the present invention, several compositions were prepared, then applied to human hair to demonstrate the improved hair set retention properties afforded by compositions including a water-insoluble amino-containing compound and an ionizable metal salt, wherein the metal has a valence of at least II; having a pH of from about 2.7 to about 4.5; and having the molar amount of the metal salt equal to or greater than the molar and/or molar-equivalent amount of the amino-containing compound. Representative compositions, and their method of manufacture, are presented in Examples I, II and III, showing that a composition of the present invention can be formulated into a variety of end use products depending upon consumer preferences.

EXAMPLE I

Solution/Spray Formulation

| Ingredient | Wt % |
| --- | --- |
| 1. Water, soft | q.s to 100% |
| 2. Isopropyl Alcohol 99% | q.s. |
| 3. Trimethylsilylamodimethicone (.00038 moles) | 3.0% |
| 4. Aluminum chloride hexahydrate ($AlCl_3 \cdot 6H_2O$) (.00038 moles) | 0.1% |
| 5. Hydrochloric acid (HCl) | q.s. to pH 2.7–4.5 |
| 6. Preservatives, dyes, fragrances, and other optional components | as desired |

The amino-functionalized silicone (trimethylsilylamodimethicone) and a sufficient amount of isopropyl alcohol to solubilize the amino-functionalized silicone are admixed and thoroughly blended to form a first solution. The aluminum chloride hexahydrate and water similarly are admixed and thoroughly blended to form a second solution. The first alcohol-aminofunctionalized solution is added to the second water-aluminum chloride solution, and the resulting solution blend is thoroughly mixed. The pH then is adjusted to between 2.7 and 4.5 with hydrochloric acid, and the desired optional ingredients, such as preservatives, dyes and/or fragrances, are added to produce a clear solution of low viscosity. As discussed previously and as will be demonstrated hereinafter, the amino-functionalized silicone can be interchanged with another water-insoluble amino-containing compound or compounds, and the aluminum chloride hexahydrate can be interchanged with another suitable ionizable metal salt or ionizable metal salts.

EXAMPLE II

Emulsion/Conditioner

| Ingredient | Wt % |
| --- | --- |
| 1. Water, soft | q.s. to 100% |
| 2. Cetyl Alcohol | 4.0% |
| 3. Ethoxylated (4) Lauryl Alcohol (Laureth-4) | 5.7% |
| 4. Ethoxylated (23) Lauryl Alcohol (Laureth-23) | 0.3% |
| 5. Hydrogenated Tallow Amine (.00038 moles) | 0.1% |
| 6. Aluminum chloride hexahydrate ($AlCl_3 \cdot 6H_2O$) (.00038 moles) | 0.1% |
| 7. Hydrochloric acid (HCl) | q.s. to pH 2.7–4.5 |
| 8. Preservatives, dyes, fragrances, and other optional ingredients | as desired |

The cetyl alcohol, laureth-4, laureth-23, and hydrogenated tallow amine are admixed and heated to approximately 57° C., then mixed until uniform to form an oil phase. The water is heated to about 57° C., and the oil phase is added to the water with mixing. Mixing is continued until the mixture is a homogeneous emulsion, then the pH is adjusted to within the range of about 2.7 to about 4.5 with hydrochloric acid. The ionizable metal salt (aluminum chloride hexahydrate), previously dissolved in approximately 1%-20% of the water, is added to the homogeneous emulsion and the resulting mixture is stirred until it is homogeneous. The optional ingredients then are added as desired. The final pH is adjusted to within the range of about 2.7 to about 4.5 to yield a uniformly emulsified end product.

Analogous to the formulation presented in Example I, the water-insoluble amino-containing compound and the ionizable metal salt can be interchanged with other suitable insoluble amino-containing compounds and other suitable ionizable metal salts. Likewise, the cetyl alcohol, laureth-4 and laureth-23 can be replaced with other fatty alcohols and emulsifiers as are well-known and practiced in the art of emulsified hair conditioner formulations.

EXAMPLE III

Shampoo

| Ingredient | Wt % |
|---|---|
| 1. Water, soft | q.s. to 100% |
| 2. Sodium $C_{14}$-$C_{16}$ Olefin Sulfonate | 10.0% |
| 3. Lauramide DEA | 6.0% |
| 4. Octylamine (.00038 moles) | 0.05% |
| 5. PEG-120 Methyl Glucose Dioleate | 2.0% |
| 6. Aluminum chloride hexahydrate ($AlCl_3.6H_2O$) (.00038 moles) | 0.10% |
| 7. Hydrochloric acid (HCl) | q.s. to pH 2.7–4.5 |
| 8. Preservatives, dyes, fragrances, and other optional ingredients | as desired |

The sodium $C_{14}$-$C_{16}$ olefin sulfonate is added to the water and the resulting solution heated to approximately 5° C. above the melting point of the lauramide DEA. The lauramide DEA and the PEG-120 methyl glucose dioleate is added to the aqueous sodium $C_{14}$-$C_{16}$ olefin sulfonate solution, then the blend is mixed until homogenous. After adjusting the pH to within a range of about 2.7 to about 4.5 with hydrochloric acid, the octylamine, the metal salt and other optional ingredients are added to the homogeneous blend, and the resulting mixture is mixed until homogeneous. The final pH is adjusted to within the range of about 2.7 to about 4.5 with hydrochloric acid. A thick, clear, shampoo, possessing good foaming properties, results.

As discussed previously in Examples I and II, the water-insoluble amino-containing compound and the ionizable metal salt can be interchanged with other suitable water-insoluble amino-containing compounds and other suitable ionizable metal salts. Likewise, the sodium $C_{14}$-$C_{16}$ olefin sulfonate, lauramide DEA, and/or PEG-120 methyl glucose dioleate can be replaced with other surfactants, detergents, amides, and/or thickeners as are well known and praticed in the art of hair shampoo formulation.

To demonstrate the new and unexected results achieved by the method and composition of the present invention, several shampoo-type, solution/spray-type and emulsion/conditioner-type formulations, as illustrated in Examples I through III, were prepared, then applied to human hair. The treated hair then was tested to determine the ability of the hair treatment composition to maintain the treated hair in a particular hair set. In particular, the various hair treating compositions were tested by applying one gram of the composition to clean, wet, naturally dark brown tresses of normal virgin human hair, available commercially from DeMeo Brothers, New York, N.Y. The six inch hair tresses, each weighing two grams, were attached to a plastic tab at the root end. In each test, the composition was combed through the hair and allowed to contact the hair for from 15 seconds to 2 minutes. The hair then was rinsed with 37.8° C tap water for 30 seconds, except for tests using the solution/spray formula, wherein the solution/spray composition was not rinsed but allowed to remain on the hair. The wet, treated hair tresses then again were combed through, set on a one-half inch diameter plastic roller and secured with a hair pin. The rolled tresses then were placed in a 50° C. oven and dried for 90 minutes. After drying, the rolled tresses were removed from the oven and allowed to cool at room temperature for three hours. The rolled tresses then were placed in a chamber, maintained at a constant 26.6° C. and 80% relative humidity, for equilibration overnight.

The following morning, the rollers were removed from the hair tresses and the tresses were suspended freely in front of a panel graduated in inches. The initial length of the hair tress was recorded, and as the tresses relaxed in the 26.6° C. and 80% relative humidity chamber, tress length measurements were taken at hourly intervals over an eight hour period. The percent set retention at each hour, the set retention curves, the area under the set retention curves, and the $T_{50}$ values (half-life of the hair set) were calculated and plotted from the tress length at a particular time according to the methods fully described below. This procedure was replicated by applying each hair treatment composition to three different tresses of hair, and the average value of the three replicate tests was used in the calculations. As also will be discussed more fully hereinafter, treated hair tresses having a calculated $T_{50}$ half-life value of above 10 hours were removed from the chamber, shampooed for 1 minute with FINESSE EXTRA BODY SHAMPOO, available from Helene Curtis, Inc., Chicago, Illinois, then rinsed for 30 seconds with 37.8° C. tap water. The rolling and hair setting procedure then was repeated, and the percent set retention at each hour, the set retention curves, the area under the set retention curves, and the $T_{50}$ half-life values were calculated and plotted.

The percent set retention, the set retention curves, the area under the set retention curves and the $T_{50}$ half-life values are fully described in the publication "Set Relaxation of Human Hair", P. Diaz and M. Wong, *J.Soc.Cosmet.Chem.*, 34, 205–212 (1983). This publication describes a method of quantifying hair set retention properties for hair treated and set in the method described above. The publication shows that the amount of set retained by the hair after a particular time interval, or the percent set retention of a hair tress, can be calculated for a time (t) after a roller has been removed from a tress of set hair from the following formula:

$$\% \text{ Set Retention} = \frac{L - L_t}{L - L_0} \times 100\%, \quad \text{(Eq. 1)}$$

wherein
L = length of the fully extended hair swatch,
$L_0$ = length of the hair curl at the onset of relaxation (t=0),
$L_t$ = length of the hair curl at time t, and
t = time elapsed since roller removed from the set hair curl.

This measurement method has proven to be very precise and reliable, thereby making it possible to evaluate both the hair set retention properties of commonly used hair set compositions and the effectiveness of various components included in the hair set compositions. In addition, tresses of hair set only with water also are included in the test as a control.

Diaz and Wong found that the tresses lengthen under the effect of the 80% relative humidity as a function of time. The lengthening process therefore provides important and relevant information concerning the effectiveness of hair setting compositions. By measuring the length of the hair curl of a treated or untreated hair tress at intervals over time, the percent set retention of the tress at a particular time can be calculated, and the percent set retention of the tress over time can be graphed. The resulting graph generally takes the shape of a graph corresponding to the equation:

$$\% \text{ Set Retention} = A(t)^B, \quad \text{(Eq. 2)}$$

wherein
t=time elapsed since roller removed from the set hair curl,
A,B=constants calculated from a least squares analysis of the experimental data.

From Eq. 2, the time for the curl to lose one-half of its initial set ($T_{50}$) can be calculated from the following equation:

$$T_{50} = \text{Exp}\left[\frac{1}{B}\ln\left(\frac{50}{A}\right)\right] \quad \text{(Eq. 3)}$$

Therefore, a time constant, $T_{50}$, that is characteristic of a particular hair set, can be computed from the values of A and B, according to Eq. 3.

According to the method of Diaz and Wong, Equation 2 yields another useful constant that is characteristic of a particular hair set, the holding power ($H_p$) of the hair set. The empirical holding power ($H_p$) is derived by integrating Equation 2, from time t=0 to time t=t, to yield the formula:

$$H_p = \left(\frac{A}{B+1}\right)_t B+1 \quad \text{(Eq. 4)}$$

In practice, the empirical holding power ($H_p$) at a time t is determined more simply by calculating the area under the set relaxation curve from t=0 to t=t.

In accordance with the method and composition of the present invention, FIGS. 1 through 44 are graphs of % set retention vs. time, wherefrom the half-life $T_{50}$ of the hair set and the empirical holding power $H_p$ of the hair set are calculated. The calculated $T_{50}$ and $H_p$ values provide the basis to permit quantitative comparisons to be made between treated and untreated hair, and between hair treated with different hair treating compositions. Surprisingly and unexpectedly, these quantitative comparisons show that a composition, having a pH in the range of about 2.7 to about 4.5, and comprising a water-insoluble amino-containing compound and an ionizable metal salt, wherein the metal has a valence of at least II, provides a hair set having exceptional durability compared to prior art hair setting compositions and hair setting treatments.

To demonstrate the new and unexpected results afforded by the present invention, hair tresses were contacted with hair setting compositions by the method described above, and the % set retention, the set retention curve, the $T_{50}$ and the $H_p$ values calculated according to the method of Diaz and Wong. In order to establish the novelty and usefulness of the present invention, different water-insoluble amino-containing compounds and different ionizable metal salts were incorporated into an emulsion/conditioner formula of Example 2. In other tests varying amounts of an ionizable metal salt were incorporated into a solution/spray formula of Example 1. In every test, except for the tests relating to varying the time of contact between the hair and the composition, the composition was applied to each of three different hair tresses for 2 minutes. The results were recorded, and percent hair set retention, area under the set retention curve ($H_p$) for t=0 to t=8, and half-life $T_{50}$ values were calculated. The average value for the three replicate tresses was calculated, and that average value was plotted to obtain the average % set retention vs. time graphs.

As will be explained more fully hereinafter, a majority of the FIGS. 1 through 44 contain three plots. The unbroken line plot shows the % set retention vs. time for untreated hair; the dashed line plot shows the % set retention vs. time of the tress after treatment with the composition being tested; and the dashed-dot line plot shows the % set retention vs. time of the tress after the treated tress was shampooed one time. For treated hair tresses demonstrating a $T_{50}$ value of less than 10 hours before shampooing, the FIG., such as FIGS. 13 and 33, includes only two plots. In these cases, the shampooing of the treated hair tress was omitted, because a $T_{50}$ half-life of less than 10 hours is equivalent to a one day long hair styling, and a shampooing to determine the resulting $T_{50}$ half-life would be irrelevant to the consumer since most people re-style their hair each day.

More particularly, the data presented in Table I and the plots of FIG. 1 demonstrate that in order to achieve the advantages and benefits of the present invention both a water-insoluble amino-containing compound and an ionizable metal salt must be present in the hair setting composition. As summarized in Table I, Exps. 3 and 4 show that using a composition including only the water-insoluble amino-containing compound or only the ionizable metal salt actually imparts hair sets having half-lives ($T_{50}$) shorter than the hair set of untreated hair (Exp. 1). The holding power ($H_p$) of the hair set with a composition including only the ionizable metal salt or the amino-containing compound is essentially the same as the $H_p$ for untreated hair. Furthermore, both in Exp. 3 and 4, the $T_{50}$ and $H_p$ values are substantially less than the $T_{50}$ and $H_p$ values obtained when the hair is treated with a composition of the present invention including both an insoluble amino-containing compound and an ionizable metal salt (Exp. 2). These results are illustrated graphically in FIG. 1, wherein the plot of the hair set retention properties for the untreated hair (solid line) approximates the plots of the hair set retention properties obtained from the composition including only the amino-containing compound (dash line) and from the composition including only the metal salt (dot-dash line).

TABLE I

| | Hair Set Retention Properties For Hair Treated With Emulsion/Conditioner Formulation Of Example 2 | | | | | |
|---|---|---|---|---|---|---|
| Exp No. | Amine | Metal Salt | pH | No. Shampoos After Treatment | $H_p$ (Area Under The Curve) | $T_{50}$ (Half-Life In Hrs.) |
| 1 | — | — | — | Untreated | 466.6 | 5.9 |
| 2 | Amino-functionalized silicone | AlCl$_3$ | 3.750 | None | 696.4 | 233.7 |

TABLE I-continued

Hair Set Retention Properties For Hair Treated With Emulsion/Conditioner Formulation Of Example 2

| Exp No. | Amine | Metal Salt | pH | No. Shampoos After Treatment | $H_p$ (Area Under The Curve) | $T_{50}$ (Half-Life In Hrs.) |
|---|---|---|---|---|---|---|
| 3 | Amino-functionalized Silicone | — | 4.014 | None | 541.6 | 5.0 |
| 4 | — | AlCl₃ | 3.660 | None | 486.6 | 3.9 |

Amino-functionalized silicone = Trimethylsilylamodimethicone
AlCl₃ = Aluminum chloride hexahydrate Table II summarizes the results obtained from a series of experiments wherein an emulsion/conditioner formula of Example 2 was applied to tresses of human hair in the manner described above. The emulsion/conditioner formulation was identical in each experiment except for the particular amino-containing compound included in the formulation and except for minor and immaterial pH variations. Each experiment was performed in triplicate, and the percent set retention over time, the holding power ($H_p$) and halflife ($T_{50}$) of the hair set determined from the average value of the three replicate tests. Graphs of percent set retention versus time for this series of experiments are presented in FIGS. 2 through 20.

TABLE II

Hair Set Retention Properties For Hair Treated With Emulsion/Conditioner Formulation of Example 2
(Using Various Amines)

| FIG. No. | Exp. No. | Amine | Metal Salt | pH | No. Shampoos After Treatment | $H_p$ (Area Under The Curve) | $T_{50}$ (Half-Life in Hrs.) |
|---|---|---|---|---|---|---|---|
|  | 1 | — | — | — | Untreated Control | 466.6 | 5.9 |
| 2 | 2 | Trimethylsilylamodimethicone | AlCl₃ | 3.750 | None | 696.4 | 233.7 |
|  | 5 | Trimethylsilylamodimethicone | AlCl₃ | 3.750 | 1 | 674.2 | 26.5 |
| 3 | 6 | Octylamine | AlCl₃ | 3.731 | None | 716.1 | 388.6 |
|  | 7 | Octylamine | AlCl₃ | 3.731 | 1 | 676.9 | 58.6 |
| 4 | 8 | Dioctylamine | AlCl₃ | 3.776 | None | 671.1 | 57.7 |
|  | 9 | Dioctylamine | AlCl₃ | 3.776 | 1 | 682.6 | 57.2 |
| 5 | 10 | Trioctylamine | AlCl₃ | 3.700 | None | 699.1 | 92.0 |
|  | 11 | Trioctylamine | AlCl₃ | 3.700 | 1 | 669.8 | 58.7 |
| 6 | 12 | Cocamine | AlCl₃ | 3.600 | None | 657.6 | 36.7 |
|  | 13 | Cocamine | AlCl₃ | 3.600 | 1 | 616.9 | 15.4 |
| 7 | 14 | Bis(2-hydroxyethyl)cocoamine | AlCl₃ | 3.511 | None | 699.3 | 31.9 |
|  | 15 | Bis(2-hydroxyethyl)cocoamine | AlCl₃ | 3.511 | 1 | 676.4 | 22.2 |
| 8 | 16 | Hydrogenated Tallow Amine | AlCl₃ | 3.800 | None | 697.8 | 369.7 |
|  | 17 | Hydrogenated Tallow Amine | AlCl₃ | 3.800 | 1 | 663.8 | 40.4 |
| 9 | 18 | Dihydrogenated Tallow Amine | AlCl₃ | 3.650 | None | 707.9 | 241.6 |
|  | 19 | Dihydrogenated Tallow Amine | AlCl₃ | 3.650 | 1 | 677.8 | 114.6 |
| 10 | 20 | Trihydrogenated Tallow Amine | AlCl₃ | 3.722 | None | 702 | 188 |
|  | 21 | Trihydrogenated Tallow Amine | AlCl₃ | 3.722 | 1 | 655.3 | 64.3 |
| 11 | 22 | Pentylamine | AlCl₃ | 3.563 | None | 722.5 | 1921.8 |
|  | 23 | Pentylamine | AlCl₃ | 3.563 | 1 | 674.3 | 35.7 |
| 12 | 24 | Dipentylamine | AlCl₃ | 3.583 | None | 711.8 | 1120.7 |
|  | 25 | Dipentylamine | AlCl₃ | 3.583 | 1 | 675.5 | 44.6 |
| 13 | 26 | Cetrimonium Chloride | AlCl₃ | 3.750 | None | 482.90 | 5.4 |

TABLE II-continued

Hair Set Retention Properties For Hair Treated With
Emulsion/Conditioner Formulation of Example 2
(Using Various Amines)

| FIG. No. | Exp. No. | Amine | Metal Salt | pH | No. Shampoos After Treatment | $H_p$ (Area Under The Curve) | $T_{50}$ (Half-Life in Hrs.) |
|---|---|---|---|---|---|---|---|
| | | (CETAC) | | | | | |
| 14 | 27 | Monoethanol-amine (MEA) | $AlCl_3$ | 3.687 | None | 651.5 | 56.9 |
| | 28 | Monoethanol-amine (MEA) | $AlCl_3$ | 3.687 | 1 | 565.8 | 7.0 |
| 15 | 29 | Triethanol-amine (TEA) | $AlCl_3$ | 3.580 | None | 656.4 | 34.2 |
| | 30 | Triethanol-amine (TEA) | $AlCl_3$ | 3.580 | 1 | 545.3 | 8.0 |
| 16 | 31 | $C_{20}$–$C_{22}$ Alkyl Amine | $AlCl_3$ | 3.738 | None | 694.5 | 25.7 |
| | 32 | $C_{20}$–$C_{22}$ Alkyl Amine | $AlCl_3$ | 3.738 | 1 | 540.3 | 7.6 |
| 17 | 33 | Butylamine | $AlCl_3$ | 3.713 | None | 675.5 | 33.4 |
| | 34 | Butylamine | $AlCl_3$ | 3.713 | 1 | 540.6 | 6.7 |
| 18 | 35 | Dibutyl-amine | $AlCl_3$ | 3.626 | None | 683.6 | 75.0 |
| | 36 | Dibutyl-amine | $AlCl_3$ | 3.626 | 1 | 522.1 | 6.6 |
| 19 | 37 | Triethyl-amine | $AlCl_3$ | 3.729 | None | 688.5 | 75.2 |
| | 38 | Triethyl-amine | $AlCl_3$ | 3.729 | 1 | 502.4 | 5.1 |
| 20 | 39 | Tripropyl-amine | $AlCl_3$ | 3.655 | None | 736.3 | 4373.7 |
| | | Tripropyl-amine | $AlCl_3$ | 3.655 | 1 | 701.7 | 102.6 |

$AlCl_3$ = Aluminum chloride hexahydrate

As demonstrated in the data of Table II, and as shown in FIGS. 2 through 20, a water-insoluble amino-containing compound improves the hair set retention properties of treated hair when the amino-containing compound is combined with a suitable ionizable metal salt and when the pH of the resulting composition is adjusted to within a suitable range. Conversely, the hair set retention properties are not similarly improved when a water-soluble amine or cationic quaternary ammonium chloride is included in the hair treating composition in conjunction with the ionizable metal salt.

For example, FIG. 2 shows plots of % set retention versus time for Experiments 1, 2 and 5 of Table II. The unbroken line in FIG. 2 is the plot for an untreated tress of hair that is rolled and set in accordance with the procedure described above. By using Equations 1 through 4, it is shown that untreated hair has a set retention half-life ($T_{50}$) of 5.9 hours, and an empirical holding power ($H_p$) of 466.6. However, in accordance with the new and surprising benefits afforded by the present invention, treating a hair tress with a composition of the present invention that includes an amino-functionalized silicone (trimethylsilylamodimethicone) and aluminum chloride provides the dashed line plot of FIG. 2, and gives an unexpected increase in hair set half-life ($T_{50}$) of 233.7 hours, and an empirical holding power of 696.4, or an approximately 49% improvement in holding power over untreated hair.

More surprisingly, shampooing this same treated hair tress with a commercial shampoo, followed by resetting the hair and again measuring the set retention properties (Exp. 5) provided the dot-dash plot of FIG. 2, still showing a substantially improved $T_{50}$ of 26.5 hrs. and an $H_p$ of 674.2, or a 44.5% improvement, over the untreated tress of hair (Exp. 1). Such results are new and unexpected in the art of hair sets both because a $T_{50}$ of 10 hrs. is considered sufficient to have the hair set last for an entire day, and because upon shampooing, or merely wetting the hair, the effect of the hair treatment upon hair set properties is usually essentially eliminated, thereby requiring another treatment of the hair to keep the hair set in place. However, in accordance with the present invention, the hair set of hair treated with the present composition has sufficient durability such that, if desired, it can last several days without a shampooing, and surprisingly can last at least through one shampooing, thereby making the daily application of the hair set treatment to the hair unnecessary.

FIGS. 3 through 12, corresponding to Exps. 6 through 25 of Table II, show similar results upon substituting other water-insoluble amino-containing compounds for the trimethylsilylamodimethicone in the emulsion/conditioner formulation of Example 2. Compared to an untreated tress of hair having a $T_{50}$ of 5.9 hours (Exp. 1), the $T_{50}$ for the other water-insoluble amino-containing compounds ranged from 31.9 hours (Exp. 14) to 1921.8 hours (Exp. 22) for unshampooed tresses; and from 15.4 hours (Exp. 13) to 114.6 hours (Exp. 19) for treated tresses that were shampooed one time. Similarly, the holding power ($H_p$) showed improvements of up to 54.5% (Exp. 22) for unshampooed tresses, and up to 46.3% (Exp. 9) for treated tresses that were shampooed one time.

In contrast, FIGS. 13 through 19 and Exps. 26 through 38 of Table II show that water-soluble amines and quaternary ammonium chlorides do not afford the hair set retention benefits provided by water-insoluble amino-containing compound incorporated into an emulsion/conditioner formulation of Example 2. For example, FIG. 13 shows that using a water-soluble quaternary ammonium chloride in the emulsion/conditioner formulation yield treated hair having essentially the same hair set retention properties as untreated hair, especially in regard to $T_{50}$ half-life values. The water soluble amines MEA and TEA (FIGS. 14 and 15 and Exps. 27 and 29) do provide improved $T_{50}$ half-life values compared to untreated hair, however any benefits provided by the water-soluble amines are eliminated after a single shampooing, thereby requiring reapplication of the hair setting composition each day (i.e., $T_{50}$ is less than 10 hours after shampooing). Similarly, other water soluble amines such as butylamine, dibutylamine and triethylamine (FIGS. 17–19 and Exps. 33–38) show improved $T_{50}$ half-line compared to untreated hair, however, again any benefits afforded are eliminated after a single shampooing. It also should be noted that tripropylamine, that does not have a carbon chain of at lease five carbon atoms, but nevertheless is sufficiently water insoluble because of its overall carbon content, does provide the benefits and advantages of the present invention. However, from FIG. 16 and Exps. 31 and 32, wherein a $C_{20}$–$C_{22}$ alkyl amine is incorporated into the hair-treating composition as the water-insoluble amino-containing compound, the $T_{50}$ half-life value after a single shampooing was 7.6 hours, therefore indicating an upper limit to the length of the carbon, or carbon-silicon, chain length of approximately 20 to 22 carbon atoms.

Therefore, in accordance with the present invention, after applying a hair setting composition, including a water-insoluble amino-containing compound and aluminum chloride and having a suitably adjusted pH, hair set retention properties are sufficiently improved such that the hair setting composition does not have to be reapplied to the hair after each shampooing, and such that the hair set has the potential to last several days. As shown in FIGS. 1 through 20, and Exp. 1 through 40, the amino-containing compound must be essentially water-insoluble and therefore the presence of hydrophilic functionalities such as amide or carboxyl, quaternary ammonium, or hydroxyl functionalities in the amino-containing compound should be minimized or eliminated. Similarly, the amino-containing compound must possess a sufficiently long carbon or carbon-silicon chain length, or a sufficient number of carbon atoms in total, to make the amino-containing compound sufficiently water-insoluble.

Without being limited to any particular theory as to why water-insoluble amino-containing compounds provide the unexpected benefits of the present invention, it is proposed that the water-soluble amino-containing compounds are too readily removed from the hair thereby making them unavailable to interact with the metal ion to provide desirable hair set retention properties. Similarly, if the carbon chain length is too great, such as greater than about 20 to 22 carbon atoms, physical effects, such as steric hindrance effects, may preclude the effective interaction between the water-insoluble amine and the metal ion needed to impart the durable hair set retention properties of the present invention. Surprisingly, however, a water-insoluble amine having two or three alkyl groups of a chain length of about eighteen, i.e., dihydrogenated tallow amine and trihydrogenated tallow amine, did demonstrate the ability to impart durable hair set retention properties when incorporated into a composition of the present invention. Therefore, chain length, as opposed to total carbon content produces the undesirable physical effects that preclude interaction between the amino-compound and metal salt. As a result, the identity of the water-insoluble amino-containing compound utilized in the present invention is not particularly limited, such that essentially any water-insoluble amino-containing compound having at least one carbon chain length of from five to about 20 to about 22 carbon atoms or having a total carbon content of at least nine carbon atoms, i.e., tripropyl amine, can be used in the composition of the present invention. Similarly, amino-functionalized silicones of general structure I also can be used as the water-insoluble amino-containing compound.

In accordance with another important feature of the present invention, it has been shown that any ionizable metal salt, wherein the metal has a valence of at least II, can be used in combination with a water-insoluble amino-containing compound to improve the hair set retention properties of treated human hair. As summarized in Table III, and shown in FIG. 1 and FIGS. 21 through 28, hair treated with an emulsion/conditioner formulation of Example 2 adjusted to a proper pH and containing an amino-functionalized silicone and an ionizable metal salt exhibits improved hair set retention properties if the metal of the ionizable metal salt has a valence of at least II. In performing the tests summarized in Table III, the emulsion/conditioner formulation was identical in each experiment, except for the particular ionizable metal salt employed and except for minor and immaterial pH variations. As in the experiments summarized in Table II, each experiment summarized in Table III was performed in triplicate and the plotted values were the average values of the three replicate tests.

TABLE III

Hair Set Retention Properties For Hair Treated With Emulsion/Conditioner Formulation of Example 2 (Using Various Ionized Metal Salts)

| FIG. No. | Exp. No. | Amine | Metal Salt | pH | No. Shampoos After Treatment | $H_p$ (Area Under The Curve) | $T_{50}$ (Half-Life in Hrs.) |
|---|---|---|---|---|---|---|---|
| | 1 | — | — | — | Untreated | 466.6 | 5.9 |
| 1 | 2 | Amino-functionalized Silicone | AlCl$_3$ | 3.750 | None | 696.4 | 233.7 |
| | 5 | Amino-functionalized Silicone | AlCl$_3$ | 3.750 | 1 | 674.2 | 26.5 |
| 21 | 41 | Amino-func- | Al$_2$ | 3.875 | None | 686.7 | 816.3 |

TABLE III-continued

Hair Set Retention Properties For Hair Treated With
Emulsion/Conditioner Formulation of Example 2
(Using Various Ionized Metal Salts)

| FIG. No. | Exp. No. | Amine | Metal Salt | pH | No. Shampoos After Treatment | $H_p$ (Area Under The Curve) | $T_{50}$ (Half-Life in Hrs.) |
|---|---|---|---|---|---|---|---|
| | | tionalized Silicone | $(SO_4)_3$ | | | | |
| | 42 | Amino-functionalized Silicone | $Al_2(SO_4)_3$ | 3.875 | 1 | 675.2 | 170.3 |
| 22 | 43 | Amino-functionalized Silicone | Al (Lactate) | 3.951 | None | 690.7 | 42.0 |
| | 44 | Amino-functionalized Silicone | Al (Lactate) | 3.951 | 1 | 652.9 | 10.8 |
| 23 | 45 | Amino-functionalized Silicone | $CuCl_2$ | 3.700 | None | 690.3 | 1028.5 |
| | 46 | Amino-functionalized Silicone | $CuCl_2$ | 3.700 | 1 | 618.7 | 35.3 |
| 24 | 47 | Amino-functionalized Silicone | $MgCl_2$ | 3.520 | None | 729.6 | 1807.9 |
| | 47 | Amino-functionalized Silicone | $MgCl_2$ | 3.520 | 1 | 608.6 | 25.9 |
| 25 | 49 | Amino-functionalized Silicone | $ZnCl_2$ | 3.618 | None | 635.2 | 23.5 |
| | 50 | Amino-functionalized Silicone | $ZnCl_2$ | 3.618 | 1 | 668.8 | 47.1 |
| 26 | 51 | Amino-functionalized Silicone | $FeCl_3$ | 3.641 | None | 663.8 | 38.5 |
| | 52 | Amino-functionalized Silicone | $FeCl_3$ | 3.641 | 1 | 596.4 | 13.4 |
| 27 | 53 | Amino-functionalized Silicone | $CaSO_4$ | 3.602 | None | 697.8 | 59.9 |
| | 54 | Amino-functionalized Silicone | $CaSO_4$ | 3.602 | 1 | 705.5 | 82.2 |
| 28 | 55 | Amino-functionalized Silicone | KCl | 3.670 | None | 671.9 | 50.7 |
| | 56 | Amino-functionalized Silicone | KCl | 3.670 | 1 | 565.1 | 6.5 |

Amino-functionalized silicone = Trimethylsilylamodimethicone

Table III first resummarizes Exps. 1, 2 and 5 of Table II. These three experiments show the unexpected improvement in the hair set retention properties of human hair provided by the composition of the present invention. Table III further shows, in Exps. No. 41 through 54, that other ionizable metal salts, wherein the metal has a valence of at least II, also can be used in the composition of the present invention. For example, other ionizable salts of aluminum, such as aluminum sulfate or aluminum lactate, shown in Exps. 41 through 44, can be used to improve the hair set retention properties of treated hair such that the hair does not have to be retreated after a shampooing in order to have the hair set last for at least an entire day. Similarly, Exps. 45 through 54 and FIGS. 23 through 27 show that essentially any ionizable metal salt, wherein the metal has a valence of at least II, can be used in accordance with the present invention. In each of the Exps. 2, 5 and 41 through 54, the half-life of the hair set ($T_{50}$), both before and after a shampooing, is greater than 10 hours, if the metal has a valence of at least II, therefore demonstrating that hair treated with a composition of the present invention retains the hair set, either before or after a shampooing, for at least an entire day. Similarly, the empirical holding power ($H_p$) for Exps. 2, 5 and 41 through 54 is dramatically increased over the $H_p$ for the untreated hair (Exp. 1). It also has been found that hair treated with emulsion/conditioner formulations of Example 2 including potassium chloride (Exps. 55 and 56, FIG. 28), wherein potassium has a valence of I, does not possess the durable hair sets provided by the compositions of the present invention. Although the half-life ($T_{50}$) of unshampooed hair treated with a composition including potassium chloride (Exp. 55) is 50.7 hours, the $T_{50}$ half-life value of the treated hair decrease dramatically to 6.5 hours after one shampooing. Therefore, in order to maintain the desired hair set for an entire day, the hair must be retreated with the hair setting hair treatment after each shampooing.

As a result and in accordance with an important feature of the present invention, application of a hair setting composition, adjusted to a suitable pH and including a water-insoluble amino-containing compound and an ionizable metal salt, wherein the metal has a valence of at least II to human hair provides improved hair set retention properties such that the hair setting composition does not have to be reapplied to the hair after each shampooing, and such that the hair set has the potential to last several days. As illustrated in FIGS. 1 through 28 and Exps. 1 through 56 in Tables I, II and III, the amino-containing compound must be essentially water-insoluble and the metal of the ionizable metal salt must have a valence of at least II. Furthermore, it has been found that the identity of the ionizable metal salt component of the present invention is not further limited, whereby essentially any ionizable metal salt, wherein the metal has a valence of at least II, can be used in the composition of the present invention.

In order to achieve the benefits and advantages of the present invention, the hair must be treated with a sufficient amount of the water-insoluble amino-containing compound and a sufficient amount of the ionizable metal salt, either by a single vehicle composition or by two compositions, to provide improved hair set retention properties. Table IV and FIGS. 29 through 32 summarize the results of treating hair samples with the solution/spray formula of Example I containing decreasing amounts of the water-insoluble amine and the ionizable metal salt. Table IV shows that if the water-insoluble amine and ionizable metal salt are present in the composition in amounts greater than about $0.95 \times 10^{-4}$ moles (Exps. 57 through 70), a sufficient amount of both water-insoluble amine and the ionizable metal salt is present in the composition to effectively treat the hair and to provide improved hair set retention properties both initially and after a single shampooing. FIGS. 29 and 30 show that the untreated hair sample, both before and after a single shampooing, demonstrated almost identical hair set retention properties to hair treated with a composition containing $0.95 \times 10^{-4}$ moles, or less, of each of the water-insoluble amine and the ionizable metal salt. However, dramatic improvements in the $T_{50}$ half-life and holding power ($H_p$), both initially and after one shampooing, was demonstrated when the hair is treated with a composition including both the water-insoluble amino-containing compound and the ionizable metal salt in amounts greater than about $0.95 \times 10^{-4}$ moles of each component. Therefore, from Table IV, Exps. 1 and 57 through 74 and FIGS. 29 through 32, it has been demonstrated that the hair treating composition must contain at least $0.95 \times 10^{-4}$ moles, or molar equivalent, of each of the water-insoluble amino-containing compound and the ionizable metal salt in order for the composition to provide a sufficient amount of essential ingredients to effectively treat the hair and to provide to the benefits of improved hair set retention properties.

TABLE IV

Hair Set Retention Properties For Hair Treated With
The Solution/Spray Formulation Of Example I
(Varying Molar Amounts Of Amine And Metal Salt)

| Exp. No. | Moles Of Amine | Moles Of Metal | No. Shampoos After Treatment | $H_p$ (Area Under The Curve) | $T_{50}$ (Half Life In Hrs.) |
|---|---|---|---|---|---|
| 1 | — | — | Untreated | 484.5 | 5.6 |
| 57 | $7.6 \times 10^{-4}$ | $7.6 \times 10^{-4}$ | None | 682.4 | 146.1 |
| 58 | $7.6 \times 10^{-4}$ | $7.6 \times 10^{-4}$ | 1 | 641.9 | 57.8 |
| 59 | $3.8 \times 10^{-4}$ | $3.8 \times 10^{-4}$ | None | 710.1 | 524.7 |
| 60 | $3.8 \times 10^{-4}$ | $3.8 \times 10^{-4}$ | 1 | 657.0 | 59.1 |
| 61 | $1.9 \times 10^{-4}$ | $1.9 \times 10^{-4}$ | None | 685.1 | 220.8 |
| 62 | $1.9 \times 10^{-4}$ | $1.9 \times 10^{-4}$ | 1 | 641.6 | 33.4 |
| 63 | $1.8 \times 10^{-4}$ | $1.8 \times 10^{-4}$ | None | 664.6 | 38.4 |
| 64 | $1.8 \times 10^{-4}$ | $1.8 \times 10^{-4}$ | 1 | 661.5 | 18.2 |
| 65 | $1.6 \times 10^{-4}$ | $1.6 \times 10^{-4}$ | None | 653.8 | 36.0 |
| 66 | $1.6 \times 10^{-4}$ | $1.6 \times 10^{-4}$ | 1 | 676.4 | 20.3 |
| 67 | $1.4 \times 10^{-4}$ | $1.4 \times 10^{-4}$ | None | 655.2 | 32.9 |
| 68 | $1.4 \times 10^{-4}$ | $1.4 \times 10^{-4}$ | 1 | 653.1 | 17.0 |
| 69 | $1.2 \times 10^{-4}$ | $1.2 \times 10^{-4}$ | None | 566.4 | 4.4* |
| 70 | $1.2 \times 10^{-4}$ | $1.2 \times 10^{-4}$ | 1 | 597.9 | 8.9 |
| 71 | $0.95 \times 10^{-4}$ | $0.95 \times 10^{-4}$ | None | 519.9 | 8.7 |
| 72 | $0.95 \times 10^{-4}$ | $0.95 \times 10^{-4}$ | 1 | 530.0 | 9.9 |
| 73 | $0.48 \times 10^{-4}$ | $0.48 \times 10^{-4}$ | None | 503.3 | 6.8 |
| 74 | $0.48 \times 10^{-4}$ | $0.48 \times 10^{-4}$ | 1 | 503.7 | 5.8 |

*Data is anomalously low, possibly due to accidental increase in humidity to 85% and temperature to 85° F.
Amine = Octylamine
Metal = Aluminum chloride hexahydrate In accordance with another important feature of the present invention, it has been found that, in order to achieve the benefits of improved hair set retention properties, the molar amount of ionizable metal salt present in the hair treating composition must be equal to or greater than the molar, or molar-equivalent, amount of water-insoluble amino-containing compound. More particularly, for each atom of nitrogen present in the composition attributable to the amino-containing compound, at least one metal atom attributable to the ionizable metal salt also must be present. An excess molar amount of ionizable metal salt does not adversely affect the hair or the utility of the composition or method of the present invention, because any excess ionizable metal salt is simply rinsed from the hair. Table V summarizes, and FIGS. 33 and 34 demonstrate, the effect of varying the molar amount of the ionizable metal salt in relation to a fixed molar amount of a water-insoluble amino-containing compound. The data summarized in Table V is the average value of three tests obtained by applying the solution/spray formulation of Example 1 to three different hair tresses, without any subsequent rinsing of the solution/spray formulation from the hair, both prior to and subsequent to a single shampooing. Each solution/spray formulation included 0.05% by weight of the octylamine, or $3.8 \times 10^{-4}$ moles of nitrogen.

it should be noted from the essentially identical plots obtained from Exps. 59 and 77 that an excess amount of metal salt does not adversely affect the hair and that the excess is most likely rinsed from the hair and thereby

TABLE V

Hair Set Retention Properties For Hair Treated With The Solution/Spray Formulation of Example I (Varying Molar Amounts Of Ionizable Metal Salt)

| Exp. No. | Amine ($3.8 \times 10^{-4}$ Moles N) | Metal Salt | % Metal Salt | Moles Of Metal | No. Shampoos After Treatment | $H_p$ (Area Under The Curve) | $T_{50}$ (Half-Life In Hrs.) |
|---|---|---|---|---|---|---|---|
| 1 | — | — | — | — | Untreated | 484.5 | 5.6 |
| 75 | Octylamine | AlCl$_3$ | 0.05 | $1.9 \times 10^{-4}$ | None | 539.6 | 17.4 |
| 76 | Octylamine | AlCl$_3$ | 0.05 | $1.9 \times 10^{-4}$ | 1 | 515.4 | 9.7 |
| 59 | Octylamine | AlCl$_3$ | 0.1 | $3.8 \times 10^{-4}$ | None | 710.1 | 524.7 |
| 60 | Octylamine | AlCl$_3$ | 0.1 | $3.8 \times 10^{-4}$ | 1 | 657.0 | 59.1 |
| 77 | Octylamine | AlCl$_3$ | 0.5 | $19 \times 10^{-4}$ | None | 696.6 | 154.4 |
| 78 | Octylamine | AlCl$_3$ | 0.5 | $19 \times 10^{-4}$ | 1 | 622.7 | 33.5 |

AlCl$_3$ = Aluminum chloride hexahydrate

- As shown in Exps. 75 and 76 of Table V, when the molar amount of the ionizable metal salt is less than the molar amount of the amino-containing compound, the half-life ($T_{50}$) of the hair set and the holding power ($H_p$) approximate, or only marginally improve upon, the hair set retention properties of untreated hair (Exp. 1). These results are shown graphically in FIG. 33, wherein the % set retention vs. time curve for the untreated hair is essentially duplicated by the curve plotted from the average value of the three replicate trials of Exp. 75. Similarly, FIG. 34 shows that, after one shampooing, the untreated hair (Exp. 1) and the hair treated with a composition deficient in metal ion (Exp. 76) demonstrated similar hair set retention properties. However, Exps. 59 and 77, wherein the molar amount of the ionizable metal salt equals or exceeds the molar or molar-equivalent amount of the amino-containing compound, show an unexpected increase in both the half-life ($T_{50}$) and the holding power ($H_p$) of the hair set. This improvement in hair set retention properties also is demonstrated in FIG. 33, wherein the plot of the data of Exp. 59 and the plot of the data of Exp. 77 show substantial improvement in hair set retention properties over the plot of the untreated hair of Exp. 1 and the plot of the hair treated with a composition containing an insufficient amount of metal salt (Exp. 75). In addition, lost. Exps. 60 and 78 and FIG. 34 show improved results in hair set retention properties after one shampooing, when the hair is treated with a composition of the present invention that contains at least as many moles of metal ion as moles of nitrogen atom.

In accordance with another important feature of the present invention, it has been found that a hair treating composition including a water-insoluble amino-containing compound and an ionizable metal salt, wherein the metal has a valence of at least II, appreciably improves the hair set retention properties of treated hair when the composition pH is adjusted to within the range of from about 2.7 to about 4.5. Table VI and FIGS. 35 through 41 demonstrate the effect of pH on the ability of a composition including aluminum chloride as the ionizable metal salt and trimethylsilylamodimethicone as the water-insoluble amino-containing compound to improve the hair set retention properties of human hair. The data summarized in Table VI was obtained by treating hair tresses with the emulsion/conditioner formulation of Example 2. In each experiment, the emulsion/conditioner formulation was identical except for pH. Similar to the experiments summarized in Tables I through V, each experiment summarized in Table VI was performed in triplicate and the plotted values were the average values of the three replicate measurements.

TABLE VI

Hair Set Retention Properties For Hair Treated With Emulsion/Conditioner Formulation of Example 2 (Using Various pH)

| FIG. No. | Exp. No. | Amine | Metal Salt | pH | No. Shampoos After Treatment | $H_p$ (Area Under The Curve) | $T_{50}$ (Half-Life in Hrs.) |
|---|---|---|---|---|---|---|---|
| | 1 | — | — | — | Untreated | 466.6 | 5.9 |
| 35 | 79 | Amino-functionalized Silicone | AlCl$_3$ | 2.101 | None | 539.3 | 5.9 |
| 36 | 80 | Amino-functionalized Silicone | AlCl$_3$ | 2.621 | None | 537.8 | 6.6 |
| 37 | 81 | Amino-functionalized Silicone | AlCl$_3$ | 3.066 | None | 639.6 | 32.6 |
| | 82 | Amino-functionalized Silicone | AlCl$_3$ | 3.066 | 1 | 675.3 | 36.1 |

TABLE VI-continued

Hair Set Retention Properties For Hair Treated With
Emulsion/Conditioner Formulation of Example 2
(Using Various pH)

| FIG. No. | Exp. No. | Amine | Metal Salt | pH | No. Shampoos After Treatment | $H_p$ (Area Under The Curve) | $T_{50}$ (Half-Life in Hrs.) |
|---|---|---|---|---|---|---|---|
| 38 | 83 | Amino-functionalized Silicone | $AlCl_3$ | 3.504 | None | 661.1 | 157.3 |
|    | 84 | Amino-functionalized Silicone | $AlCl_3$ | 3.504 | 1 | 684.2 | 73.7 |
| 39 | 2  | Amino-functionalized Silicone | $AlCl_3$ | 3.750 | None | 696.4 | 233.7 |
|    | 5  | Amino-functionalized Silicone | $AlCl_3$ | 3.750 | 1 | 674.2 | 26.5 |
| 40 | 85 | Amino-functionalized Silicone | $AlCl_3$ | 4.430 | None | 681.2 | 213.3 |
|    | 86 | Amino-functionalized Silicone | $AlCl_3$ | 4.430 | 1 | 668.0 | 47.9 |
| 41 | 87 | Amino-functionalized Silicone | $AlCl_3$ | 4.603 | None | 408.6 | 2.4 |

Amino-functionalized silicone = Trimethylsilylamodimethicone
$AlCl_3$ = Aluminum chloride hexahydrate As illustrated in Table VI, Exps. 79, 80 and 87 test hair set compositions having a pH outside the range of about 2.7 to about 4.5. As demonstrated by the holding power ($H_p$) and half-life ($T_{50}$) of the hair sets obtained in Exps. 79, 80 and 87 and plotted in FIGS. 35, 36 and 41, emulsion/conditioner compositions of Example 2 having a pH outside the range of about 2.7 to about 4.5, when applied to human hair, provide hair set retention properties that are essentially equal to, or inferior to, the hair set retention properties of untreated hair. Conversely, compositions of the present invention having a pH of about 2.7 to about 4.5 and as illustrated in Exp. 2, 5, and 81 through 86 of Table VI and plotted in FIGS. 37 through 40, surprisingly and unexpectedly show increased half-lives ($T_{50}$) and increased empirical holding power values ($H_p$) compared to the $T_{50}$ and $H_p$ of untreated human hair. The improvement in the $T_{50}$ half-life of the hair set and the holding power ($H_p$) of the hair set is observed both before shampooing with a commercial hair shampoo (Exps. 2, 81, 83, 85) and after shampooing with a commercial hair shampoo (Exp. 5, 82, 84, 86).

Therefore, in accordance with the present invention, Tables I–VI, Exps. 1–87 and FIGS. 1–41 demonstrate that hair set retention properties are substantially improved by treating the hair with a composition that has a pH within the range of about 2.7 to about 4.5, and includes a water-insoluble amino-containing compound and at least an equal molar amount of an ionizable metal salt, wherein the metal has a valence of at least II. Hair treated with a sufficient amount of the composition of the present invention, containing at least $0.95 \times 10^{-4}$ moles each of the water-insoluble amino-containing compound and the ionizable metal salt, possesses a hair set having surprising and unexpected durability, such that the hair does not have to be retreated with the hair setting composition even after a shampooing. In addition to exceptional durability, the hair setting compositions of the present invention also impart to the hair the other beneficial hair set properties required by the consumer, such as combability, gloss, softness and body.

To demonstrate the desirability of the hair set retention properties afforded by the composition and method of the present invention, Table VII and FIG. 42 show the ability of the hair treatment composition of the present invention to provide hair set retention properties over several subsequent shampooings after treatment with a solution/spray formulation of Example 1 containing $3.8 \times 10^{-4}$ moles each of octylamine (as elemental N) and aluminum chloride hexahydrate (as metal ion). Table VII, Exps. 88 through 91, and FIG. 42 show that the $T_{50}$ half life exceeds 10 hours for no shampooings through three subsequent shampooings. Therefore, hair treated with the solution/spray formulation of Example 1 will not have to be retreated for several days, or until after at least three subsequent shampooings after the original treatment. Such durable hair set retention properties are both new and unexpected in the art. Similarly, and even more surprising and unexpected, Table VIII, Exps. 93 through 97 and FIG. 43 show that a hair treating composition including $3.8 \times 10^{-4}$ moles each of the water-insoluble amino-containing compound (as elemental N), trimethylsilylamodimethicone, and the ionizable metal salt (as metal ion), magnesium chloride hexahydrate, showed a durable hair set that retained its hair set properties after four subsequent shampooings because the $T_{50}$ half-life of 13.6 hours after 4 shampooings shows that the hair set still will be retained for at least an entire day. Therefore, hair treated with a composition of the present invention will hold a desired hair configuration for several days, or through approximately three to five subsequent shampooings, before the hair must be retreated with the hair setting composition. In contrast, the prior art hair setting compositions require retreatment after merely wetting the hair a single time with water.

TABLE VII

Hair Set Retention Properties For Hair Treated With
The Solution/Spray Formulation of Example 1
(Varying The Number Of Subsequent Shampoos)

| Exp. No. | No. Shampoos After Treatment | $H_p$ (Area Under The Curve) | $T_{50}$ (Half-Life in Hrs.) |
|---|---|---|---|
| 88 | 0 | 716.1 | 388.6 |
| 89 | 1 | 676.9 | 58.6 |
| 90 | 2 | 596.3 | 15.2 |
| 91 | 3 | 599.5 | 18.3 |
| 92 | 4 | 551.3 | 8.7 |

Composition includes octylamine and aluminum chloride hexahydrate at $3.8 \times 10^{-4}$ moles nitrogen and $3.8 \times 10^{-4}$ moles metal

TABLE VIII

Hair Set Retention Properties For Hair Treated With
The Solution/Spray Formulation of Example 1
(Varying The Number Of Subsequent Shampoos)

| Exp. No. | No. Shampoos After Treatment | $H_p$ (Area Under The Curve) | $T_{50}$ (Half-Life in Hrs.) |
|---|---|---|---|
| 93 | 0 | 674.3 | 38.7 |
| 94 | 1 | 620.1 | 11.6 |
| 95 | 2 | 623.9 | 15.6 |
| 96 | 3 | 637.4 | 18.9 |
| 97 | 4 | 577.2 | 13.6 |

Compound includes trimethylsilylamodimethicone and magnesium chloride hexahydrate at $3.8 \times 10^{-4}$ moles nitrogen and $3.8 \times 10^{-4}$ moles metal A further benefit afforded by the composition of the present invention is that the time required for the hair to contact the composition in order to achieve the benefit of a durable hair set is extremely short. In contrast to prior art hair setting compositions that require contact times of 15 minutes to 16 hours, the composition of the present invention effectively treats the hair within two minutes to yield a durable and esthetically pleasing hair set. As summarized in Table IX and shown in FIG. 44, a composition of the present invention can effectively treat the hair in as short a contact time as 15 seconds, thereby appreciably shortening the time necessary to produce a durable hair set.

TABLE IX

Hair Set Retention Properties For Hair Treated With
Emulsion/Conditioner Formulation Of Example 2
(Varying Contact Time Before Rinsing The Hair)

| Exp. No. | Amine | Metal Salt | Contact Time (In Minutes) | $H_p$ (Area Under The Curve) | $T_{50}$ (Half-Life In Hrs.) |
|---|---|---|---|---|---|
| 1 | — | — | Untreated | 466.6 | 5.9 |
| 98 | Amino-functionalized Silicone | $Al_2(SO_4)_3$ | 0.25 | 687.1 | 120.9 |
| 99 | Amino-functionalized Silicone | $Al_2(SO_4)_3$ | 0.50 | 696.6 | 320.3 |
| 100 | Amino-functionalized Silicone | $Al_2(SO_4)_3$ | 1.00 | 674.9 | 58.0 |
| 101 | Amino-functionalized Silicone | $Al_2(SO_4)_3$ | 2.00 | 686.7 | 816.3 |

Amino-functionalized silicone = Trimethylsilylamodimethicone

As illustrated in FIG. 44 and as summarized in Table IX, a contact time between the hair and a composition of the present invention (Exp. 98) as short as 15 seconds increases the $T_{50}$ half-life of the treated hair to 120.9 hrs. (Exp. 98), compared to a $T_{50}$ half-life for untreated hair of 5.9 hours. A 30 second contact time further increased the $T_{50}$ half-life to 320.3 hours (Exp. 99). Table IX and FIG. 44 also demonstrate the improved holding power ($H_p$) of hair treated for 15 sec. (Exp. 98, dot-dash plot), for 30 sec. (Exp. 99, long dash plot), for 1 min. (Exp. 100, dot plot) and for 2 min. (Exp. 101, short dash plot) compared to untreated hair (Exp. 1, unbroken line plot). In addition, it has been found that by allowing the composition to contact on the hair for longer than 2 minutes does not lead to further improvement in the hair set retention properties or to any adverse effects on the hair either in regard to holding power ($H_p$), to half-life ($T_{50}$) or to aesthetic properties of the hair set.

In accordance with another important feature of the present invention, it has been found that in addition to treating the hair with a single composition including both the insoluble amino-containing compound and the ionizable metal salt to obtain improved hair set retention properties, the hair can be treated sequentially with a composition including the water-insoluble amino-containing compound and with a composition including the ionizable metal salt to yield hair sets having improved hair set retention properties. It has been shown that the above-described benefits of improved hair set retention properties can be achieved by treating the hair with two compositions, wherein in one composition aluminum chloride hexahydrate was incorporated into the shampoo formulation of Example 3 absent water-insoluble amine, and in the second composition the trimethylsilylamodimethicone was incorporated into the conditioner/emulsion formulation of Example 2 absent metal salt.

Accordingly, three virgin tresses of naturally brown hair, each weighing 2 grams, were each shampooed with one gram of the above-described shampoo for one minute, then rinsed with 37.8° C. tap water for 30 seconds. The wet hair tresses were blotted with a towel, then one gram of the above-described conditioner/emulsion formula including the trimethylsilylamodimethicone was applied to each damp tress. The conditioner/emulsion was combed through the hair, then allowed to remain on the hair for 2 minutes. The tresses again were rinsed with 37.8° C. tap water for 30 seconds. Each tress was wound on a plastic roller and the hair set procedure previously described was performed.

Figure 45:
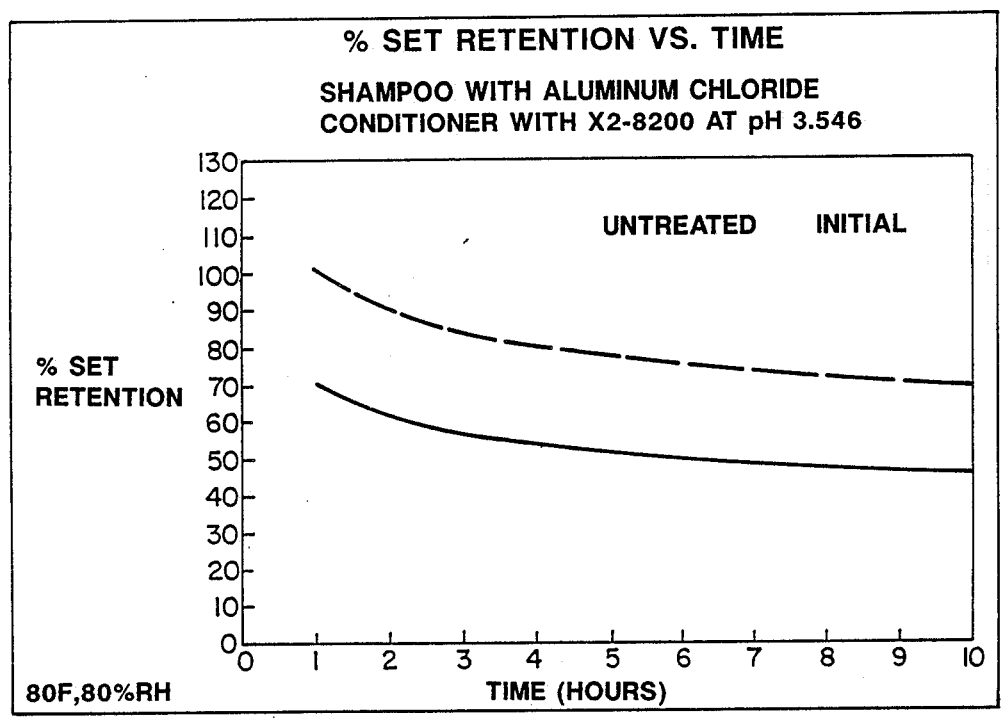
FIG. 45 is a graph comparing % set retention vs. time for untreated hair to % set retention vs. time for hair initially treated with a shampoo containing aluminum chloride and subsequently treated with a conditioner including an amino-functionalized silicone. The hair set retention properties are summarized in Table X.

As demonstrated in Table X and FIG. 45, the benefits of improved hair set retention properties are achieved by applying the water-insoluble amino-containing compound and the ionizable metal salt to the hair from separate compositions. From Table X, it is readily observed that both the holding power ($H_p$) and the half-life ($T_{50}$) of the hair set obtained by treating the hair using two compositions (Exp. 102) is appreciably improved over the hair set properties obtained for untreated hair (Exp. 1) and approximates the hair set properties obtained for hair treated with a single composition including both the amino-containing compound and the ionizable metal salt (Exp. 2).

TABLE X

Hair Set Retention Properties For Hair Treated With Shampoo Formulation Of Example 3 And With Emulsion/Conditioner Formulation Of Example 2

| Exp. No. | Amine | Metal Salt | pH | $H_p$ (Area Under The Curve) | $T_{50}$ (Half-Life In Hrs.) |
|---|---|---|---|---|---|
| 1 | Untreated | — | — | 466.6 | 5.9 |
| 2 | Trimethyl-silylamo-dimethi-cone | $AlCl_3$ | 3.750 | 696.4 | 233.7 |
| 102 | Trimethyl-silylamo-dimethi-cone (in the conditioner formulation) | $AlCl_3$ (in the shampoo formulation) | 3.546 | 682.3 | 72.5 |

The improved hair set retention properties demonstrated in Table X and FIG. 45 show that the amino-containing compound and the ionizable metal salt each can be incorporated into separate formulations and then applied to the hair sequentially. Further, it should be noted that other combinations of formulation are possible for applying the amino-containing compound and the ionizable metal salt to the hair. For example, a conditioner containing the amino-compound can be applied to the hair, followed by applying a solution/spray formulation containing the metal salt. Likewise, several other combinations of formulations that are amenable to easy consumer application can be envisioned.

Although there are several commercial products in the marketplace to improve the set holding properties of hair, such as setting lotions, gels and hairsprays, these products must be applied to the hair after each shampoo either prior to or during the styling process. However, in accordance with the method of the present invention, contacting the hair with a composition including an amino-containing compound and an ionizable metal salt provides a hair set that is durable and resistant to at least one subsequent shampooing. As a result, the hair setting composition does not need to be re-applied to the hair before each hair styling, therefore making hair setting more convenient for the consumer. In addition, the method of the present invention provides the further benefits of not leaving the hair tacky or sticky, unlike conventional setting lotions; not forming a crust and therefore providing combability, unlike conventional hair sprays; and not damaging the hair, unlike conventional permanents. Further, the benefits afforded by the composition of the present invention are achieved regardless of whether the composition is applied in a rinse-off or a leave-on fashion. In addition, after treating the hair with the composition of the present invention, the set hair feels natural, has body, is soft, shiny and combable, and yet retains the imparted hair style even under high humidity conditions. These beneficial effects can be achieved by using an aqueous spray or solution formulation, emulsion formulation, shampoo formulation or a suitable combination of all three formulations.

Obviously, many modifications and variations of the invention as hereinbefore set forth can be made without departing from the spirit and scope thereof and therefore only such limitations should be imposed as are indicated by the appended claims.

What is claimed is:

1. A hair setting composition comprising an effective amount of a water-insoluble amino-containing compound having a water solubility of 0.5 g or less per 100 milliliters of water, wherein the water-insoluble amino-containing compound is a primary amine or a secondary amine having the structure

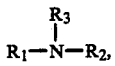

wherein when the amino-containing compound is a primary amine, $R_1$ is an alkyl group or substituted alkyl group of between five and about 20 carbon atoms in length, and $R_2$ and $R_3$ are hydrogen atoms, and when the amino-containing compound is a secondary amine, $R_1$ and $R_2$ are alkyl groups or substituted alkyl groups of about 20 or less carbon atoms in length and wherein either $R_1$ or $R_2$ is at least five carbon atoms in length, and $R_3$ is a hydrogen atom; an effective amount of an ionizable metal salt, wherein the metal of the ionizable metal salt has a valence of at least II; and a suitable carrier; wherein the composition has a pH of from about 2.7 to about 4.5 and the ionizable metal salt and water-insoluble amino-containing compound are present in the composition in a molar or molar-equivalent ratio of at least 1:1.

2. The composition of claim 1 wherein the water-insoluble amino-compound is a primary amine, wherein $R_1$ is an alkyl group or a substituted alkyl group of between five and about 20 carbon atoms in length, and $R_2$ and $R_3$ are hydrogen atoms.

3. The composition of claim 1 wherein the water-insoluble amino-compound is a secondary amine, wherein $R_1$ and $R_2$ are alkyl groups or substituted alkyl groups of about 20 or less carbon atoms in length, and wherein either $R_1$ or $R_2$ is at least five carbon atoms in length, and $R_3$ is a hydrogen atom.

4. The composition of claim 1 wherein the metal of the ionizable metal salt is selected from the group consisting of magnesium, calcium, barium, titanium, vanadium, manganese, mercury, cadmium, lead, iron, cobalt, nickel, silver, copper, cerium, hafnium, germanium, zinc, and zirconium; or mixtures thereof.

5. The composition of claim 1 wherein the ionizable metal salt is selected from the group consisting of aluminum chloride, aluminum sulfate, aluminum lactate, copper chloride, magnesium chloride, zinc chloride, ferric chloride and calcium sulfate; or mixtures thereof.

6. The composition of claim 1 wherein the composition includes the water-insoluble amino-containing compound in amounts of at least $1.2 \times 10^{-4}$ molar, as elemental nitrogen, and includes the ionizable metal salt in amounts of at least $1.2 \times 10^{-4}$ molar, as metal ion.

7. The composition of claim 1 wherein the composition includes the water-insoluble amino-containing compound in amounts of at least $1.4 \times 10^{-4}$ molar, as elemental nitrogen, and includes the ionizable metal salt in amounts of at least $1.4 \times 10^{-4}$ molar, as metal ion.

8. The composition of claim 1 wherein the composition includes the water-insoluble amino-containing compound in amounts of at least $1.6 \times 10^{-4}$ molar, as elemental nitrogen, and includes the ionizable metal salt in amounts of at least $1.6 \times 10^{-4}$ molar, as metal ion.

9. The composition of claim 1 wherein the composition includes the water-insoluble amino-containing compound in amounts of at least $1.9 \times 10^{-4}$ molar, as elemental nitrogen, and includes the ionizable metal salt in amounts of at least $1.9 \times 10^{-4}$ molar, as metal ion.

10. The composition of claim 1 wherein the carrier comprises water.

11. The composition of claim 1 wherein the ionizable metal salt includes an anion that is organic or inorganic in chemical structure.

12. The composition of claim 11 wherein the anion of the ionizable metal salt is selected from the group consisting of chloride, bromide, sulfate, nitrate, phosphate, acetate and lactate; or mixtures thereof.

13. The composition of claim 1 wherein the composition includes the water-insoluble amino-containing compound in amounts greater than $0.9 \times 10^{-4}$ molar, as elemental nitrogen, and includes the ionizable metal salt in amounts greater than $0.9 \times 10^{-4}$ molar, as metal ion.

14. The composition of claim 13 wherein the composition includes the water-insoluble amino-containing compound in amounts greater than $1.0 \times 10^{-4}$ molar, as elemental nitrogen, and includes the ionizable metal salt in amounts greater than $1.0 \times 10^{-4}$ molar, as metal ion.

15. A hair setting composition comprising an effective amount of a water-insoluble amino-containing compound having a water solubility of 0.5 g or less per 100 milliliters of water, wherein the water-insoluble amino-containing compound is a tertiary amine having the structure

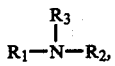

wherein $R_1$, $R_2$, and $R_3$ are alkyl groups or substituted alkyl groups of about 20 or less carbon atoms in length, and wherein either $R_1$, $R_2$, or $R_3$ is at least five carbon atoms in length; an effective amount of an ionizable metal salt, wherein the metal of the ionizable metal salt has a valence of at least II; and a suitable carrier; wherein the composition has a pH of from about 2.7 to about 4.5 and the ionizable metal salt and water-insoluble amino-containing compound are present in the composition in a molar or molar-equivalent ratio of at least 1:1.

16. The composition of claim 15 wherein the metal of the ionizable metal salt is selected from the group consisting of magnesium, calcium, barium, titanium, vanadium, manganese, mercury, cadmium, lead, iron, cobalt, nickel, silver, copper, cerium, hafnium, germanium, zinc, zirconium, and mixtures thereof.

17. The composition of claim 15 wherein the ionizable metal salt is selected from the group consisting of aluminum chloride, aluminum sulfate, aluminum lactate, copper chloride, magnesium chloride, zinc chloride, ferric chloride, calcium sulfate, and mixtures thereof.

18. The composition of claim 15 wherein the composition includes the water-insoluble amino-containing compound in amounts greater than $0.9 \times 10^{-4}$ molar, as elemental nitrogen, and includes the ionizable metal salt in amounts greater than $0.9 \times 10^{-4}$ molar, as metal ion.

19. The composition of claim 15 wherein the composition includes the water-insoluble amino-containing compound in amounts of at least $1.9 \times 10^{-4}$ molar, as elemental nitrogen, and includes the ionizable metal salt in amounts of at least $1.9 \times 10^{-4}$ molar, as metal ion.

20. The composition of claim 15 wherein the carrier comprises water.

21. The composition of claim 15 wherein the ionizable metal salt includes an anion that is organic or inorganic in chemical structure.

22. The composition of claim 21 wherein the anion of the ionizable metal salt is selected from the group consisting of chloride, bromide, sulfate, nitrate, phosphate, acetate, lactate, and mixtures thereof.

23. A hair setting composition comprising an effective amount of a water-insoluble amino-containing compound having a water-solubility of 0.5 g or less per 100 milliliters of water, wherein the water-insoluble amino-containing compound is an amino-functionalized silicone; an effective amount of an ionizable metal salt, wherein the metal of the ionizable metal salt has a valence of at least II; and a suitable carrier; wherein the composition has a pH of from about 2.7 to about 4.5 and the ionizable metal salt and water-insoluble amino-containing compound are present in the composition in a molar or molar-equivalent ratio of at least 1:1.

24. The composition of claim 23 wherein the water-insoluble amino-functionalized silicone is a trimethylsilylamodimethicone having the structure

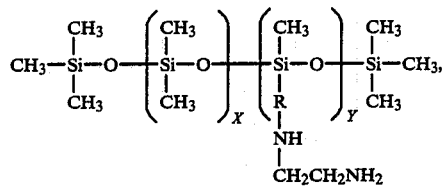

wherein $X+Y$ is a number from about 50 to about 500, and the mole % amine functionality varies from about 1% to about 5%, and wherein R is an alkyl group having from 2 to 5 carbon atoms.

25. The composition of claim 23 wherein the metal of the ionizable metal salt is selected from the group consisting of magnesium, calcium, barium, titanium, vanadium, manganese, mercury, cadmium, lead, iron, cobalt, nickel, silver, copper, cerium, hafnium, germanium, zinc, zirconium, and mixtures thereof.

26. The composition of claim 23 wherein the ionizable metal salt is selected from the group consisting of aluminum chloride, aluminum sulfate, aluminum lactate, copper chloride, magnesium chloride, zinc chloride, ferric chloride, calcium sulfate, and mixtures thereof.

27. The composition of claim 23 wherein the composition includes the water-insoluble amino-containing compound in amounts greater than $0.9 \times 10^{-4}$ molar, as elemental nitrogen, and includes the ionizable metal salt in amounts greater than $0.9 \times 10^{-4}$ molar, as metal ion.

28. The composition of claim 23 wherein the composition includes the water-insoluble amino-containing compound in amounts of at least $1.2 \times 10^{-4}$ molar, as elemental nitrogen, and includes the ionizable metal salt in amounts of at least $1.2 \times 10^{-4}$ molar, as metal ion.

29. The composition of claim 23 wherein the composition includes the water-insoluble amino-containing compound in amounts of at least $1.9 \times 10^{-4}$ molar, as elemental nitrogen, and includes the ionizable metal salt in amounts of at least $1.9 \times 10^{-4}$ molar, as metal ion.

30. The composition of claim 23 wherein the carrier comprises water.

31. The composition of claim 23 wherein the ionizable metal salt includes an anion that is organic or inorganic in chemical structure.

32. The composition of claim 31 wherein the anion of the ionizable metal salt is selected from the group consisting of chloride, bromide, sulfate, nitrate, phosphate, acetate, lactate, and mixtures thereof.

33. A method of treating human hair with a hair setting composition comprising contacting human hair with a composition comprising an effective amount of a water-insoluble amino-containing compound having a water solubility of 0.5 g or less per 100 milliliters of water, wherein the water-insoluble amino-containing compound is a primary amine of a secondary amine having the structure

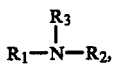

wherein when the amino-containing compound is a primary amine, $R_1$ is an alkyl group or substituted alkyl group of between five and about 20 carbon atoms in length, and $R_2$ and $R_3$ are hydrogen atoms, and when the amino-containing compound is a secondary amine, $R_1$ and $R_2$ are alkyl groups or substituted alkyl groups of about 20 or less carbon atoms in length and wherein either $R_1$ or $R_2$ is at least five carbon atoms in length, and $R_3$ is a hydrogen atom; an effective amount of an ionizable metal salt, wherein the metal of the ionizable metal salt has a valence of at least II; and a suitable carrier; wherein the composition has a pH of from about 2.7 to about 4.5 and the ionizable metal salt and water-insoluble amino-containing compound are present in the composition in a molar or molar-equivalent ratio of at least 1:1.

34. The method of claim 33 wherein the water-insoluble amino-compound is a primary amine, wherein $R_1$ is an alkyl group or a substituted alkyl group of between five and about 20 carbon atoms in length, and $R_2$ and $R_3$ are hydrogen atoms.

35. The method of claim 33 wherein the water-insoluble amino-compound is a secondary amine, wherein $R_1$ and $R_2$ are alkyl groups or substituted alkyl groups of about 20 or less carbon atoms in length, and wherein either $R_1$ or $R_2$ is at least five carbon atoms in length, and $R_3$ is a hydrogen atom.

36. The method of claim 33 wherein the metal of the ionizable metal salt is selected from the group consisting of magnesium calcium, barium, titanium, vanadium, manganese, mercury, cadmium, lead, iron, cobalt, nickel, silver, copper, cerium, hafnium, germanium, zinc, and zirconium; or mixtures thereof.

37. The method of claim 33 wherein the ionizable metal salt is selected from the group consisting of aluminum chloride, aluminum sulfate, aluminum lactate, copper chloride, magnesium chloride, zinc chloride, ferric chloride and calcium sulfate; or mixtures thereof.

38. The method of claim 33 wherein the composition includes the water-insoluble amino-containing compound in amounts of at least $1.2 \times 10^{-4}$ molar, as elemental nitrogen, and includes the ionizable metal salt in amounts of at least $1.2 \times 10^{-4}$ molar, as metal ion.

39. The method of claim 33 wherein the composition includes the water-insoluble amino-containing compound in amounts of at least $1.4 \times 10^{-4}$ molar, as elemental nitrogen, and includes the ionizable metal salt in amounts of at least $1.4 \times 10^{-4}$ molar, as metal ion.

40. The method of claim 33 wherein the composition includes the water-insoluble amino-containing compound in amounts greater than $1.6 \times 10^{-4}$ molar, as elemental nitrogen, and includes the ionizable metal salt in amounts greater than $1.6 \times 10^{-4}$ molar, as metal ion.

41. The method of claim 33 wherein the composition includes the water-insoluble amino-containing compound in amounts of at least $1.9 \times 10^{-4}$ molar, as elemental nitrogen, and includes the ionizable metal salt in amounts of at least $1.9 \times 10^{-4}$ molar, as metal ion.

42. The method of claim 33 wherein the carrier comprises water.

43. The method of claim 33 wherein the ionizable metal salt includes an anion that is organic or inorganic in chemical structure.

44. The method of claim 43 wherein the anion of the ionizable metal salt is selected from the group consisting of chloride, bromide, sulfate, nitrate, phosphate, acetate, and lactate; or mixtures thereof.

45. The method of claim 33 wherein the composition includes the water-insoluble amino-containing compound in amounts greater than $0.9 \times 10^{-4}$ molar, as elemental nitrogen, and includes the ionizable metal salt in amounts greater than $0.9 \times 10^{-4}$ molar, as metal ion.

46. The method of claim 45 wherein the composition includes the water-insoluble amino-containing compound in amounts greater than $1.0 \times 10^{-4}$ molar, as elemental nitrogen, and includes the ionizable metal salt in amounts greater than $1.0 \times 10^{-4}$ molar, as metal ion.

47. A method of treating human hair with a hair setting composition comprising contacting human hair with a composition comprising an effective amount of a water-insoluble amino-containing compound having a water solubility of 0.5 g or less per 100 milliliters of water, wherein the water-insoluble amino-containing compound is a tertiary amine having the structure

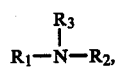

wherein $R_1$, $R_2$ and $R_3$ are alkyl groups or substituted alkyl groups of about 20 or less carbon atoms in length, and wherein either $R_1$, $R_2$ or $R_3$ is at least five carbon atoms in length; an effective amount of an ionizable metal salt, wherein the metal of the ionizable metal salt has a valence of at least II; and a suitable carrier; wherein the composition has a pH of from about 2.7 to about 4.5 and the ionizable metal salt and water-insoluble amino-containing compound are present in the composition in a molar or molar-equivalent ratio of at least 1:1.

48. The method of claim 47 wherein the metal of the ionizable metal salt is selected from the group consisting of magnesium, calcium, barium, titanium, vanadium, manganese, mercury, cadmium, lead, iron, cobalt, nickel, silver, copper, cerium, hafnium, germanium, zinc, zirconium, and mixtures thereof.

49. The method of claim 47 wherein the ionizable metal is selected from the group consisting of aluminum chloride, aluminum sulfate, aluminum lactate, copper chloride, magnesium chloride, zinc chloride, ferric chloride, calcium sulfate, and mixtures thereof.

50. The method of claim 47 wherein the composition includes the water-insoluble amino-containing compound in amounts greater than $0.9 \times 10^{-4}$ molar, as elemental nitrogen, and includes the ionizable metal salt in amounts greater than $0.9 \times 10^{-3}$ molar, as metal ion.

51. The method of claim 47 wherein the composition includes the water-insoluble amino-containing compound in amounts of at least $1.9 \times 10^{-4}$ molar, as elemental nitrogen, and includes the ionizable metal salt in amounts of at least $1.9 \times 10^{-4}$ molar, as metal ion.

52. The method of claim 47 wherein the carrier comprises water.

53. The method of claim 47 wherein the ionizable metal salt includes an anion that is organic or inorganic in chemical structure.

54. The method of claim 53 wherein the anion of the ionizable metal salt is selected from the group consisting of chloride, bromide, sulfate, nitrate, phosphate, acetate, lactate, and mixtures thereof.

55. A method of treating human hair with a hair setting composition comprising contacting human hair with a composition comprising an effective amount of water-insoluble amino-containing compound having a water solubility of 0.5 g or less per 100 milliliters of water wherein the water-insoluble amino-containing compound is an amino-functionalized silicone; an effective amount of an ionizable metal salt, wherein the metal of the ionizable metal salt has a valence of at least II; and a suitable carrier; wherein the composition has a pH of from about 2.7 to about 4.5 and the ionizable metal and water-insoluble amino-containing compound are present in the composition in a molar or molar-equivalent ratio of at least 1:1.

56. The method of claim 55 wherein the water-insoluble amino-functionalized silicone is a trimethylsilylamodimethicone having the structure

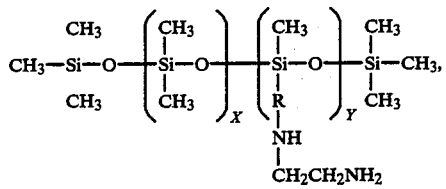

wherein $X+Y$ is a number from about 50 to about 500, and the mole % amine functionality varies from about 1% to about 5%, and wherein R is an alkyl group having from 2 to 5 carbon atoms.

57. The method of claim 55 wherein the metal of the ionizable metal salt is selected from the group consisting of magnesium, calcium, barium, titanium, vanadium, manganese, mercury, cadmium, lead, iron, cobalt, nickel, silver, copper cerium, hafnium, germanium, zinc, zirconium, and mixtures thereof.

58. The method of claim 55 wherein the ionizable metal salt is selected from the group consisting of aluminum chloride, aluminum sulfate, aluminum lactate, copper chloride, magnesium chloride, zinc chloride, ferric chloride, calcium sulfate, and mixtures thereof.

59. The method of claim 55 wherein the composition includes the water-insoluble amino-containing compound in amounts greater than $0.95 \times 10^{-4}$ molar, as elemental nitrogen, and includes the ionizable metal salt in amounts greater than $0.95 \times 10^{-4}$ molar, as metal ion.

60. The method of claim 55 wherein the composition includes the water-insoluble amino-containing compound in amounts of at least $1.2 \times 10^{-4}$ molar, as elemental nitrogen, and includes the ionizable metal salt in amounts of at least $1.2 \times 10^{-4}$ molar, as metal ion.

61. The method of claim 55 wherein the composition includes the water-insoluble amino-containing compound in amounts of at least $1.9 \times 10^{-4}$ molar, as elemental nitrogen, and includes the ionizable metal salt in amounts of at least $1.9 \times 10^{-4}$ molar, as metal ion.

62. The method of claim 55 wherein the carrier comprises water.

63. The method of claim 55 wherein the ionizable metal salt includes an anion that is organic or inorganic in chemical structure.

64. The method of claim 63 wherein the anion of the ionizable metal salt is selected from the group consisting of chloride, bromide, sulfate, nitrate, phosphate, acetate, lactate, and mixtures thereof.

65. A method of imparting durable hair set retention properties to hair comprising configuring the hair into a desired hair set configuration; treating the hair with a hair setting composition comprising an effective amount of a water-insoluble amino-containing compound having a water solubility of 0.5 g or less per 100 milliliters of water and selected from the group consisting of:
(a) a primary amine including one alkyl group or substituted alkyl group of between five and about 20 carbon atoms in length,
(b) a secondary amine including two alkyl groups or substituted alkyl groups of about 20 or less carbon atoms in length, and wherein one of the alkyl or substituted alkyl groups is at least five carbon atoms in length;
(c) a tertiary amine including three alkyl groups or substituted alkyl groups of about 20 or less carbon atoms in length and wherein at least one of the three alkyl or substituted alkyl groups is at least five carbon atoms in length,
(d) an amino-functionalized silicone, and
(e) combinations thereof;
an effective amount of an ionizable metal salt, wherein the metal of the ionizable metal salt has a valence of at least II; and a suitable carrier; wherein the composition has a pH of from about 2.7 to about 4.5 and the ionizable metal salt and water-insoluble amino-containing compound are present in the composition in a molar or molar-equivalent ratio of at least 1:1; subjecting the treated hairs to a first drying step; rewetting the hair; and subjecting the hair to a second drying step without an intermediate step of treating the hair with a hair setting composition prior to the second drying step while retaining an effective degree of the hair configuration.

66. The method of claim 65 wherein the treated hair is rewet and dryed one time to about four times without an intermediate treatment of the hair with a hair setting composition and after said rewetting and drying steps has a set configuration half-life of at least 10 hours without having to retreat the hair with a hair setting composition.

67. The method of claim 65 wherein the treated hair is rewet and dryed one time to about three times without an intermediate treatment of the hair with a hair setting composition and after said rewetting and drying steps has a set configuration half-life of at least 10 hours without having to retreat the hair with a hair setting composition.

68. A hair setting composition comprising an effective amount of a water-insoluble amino-containing compound selected from the group consisting of octylamine, dioctylamine, trioctylamine, dimethyloctylamine, pentylamine, dipentylamine, hexylamine, dihexylamine, trihexylamine, heptylamine, dodecylamine, hexadecylamine, octadecylamine, tallow amine, hydrogenated tallow amine, dihydrogenated tallow amine, trihydrogenated tallow amine, oleyl amine, soya amine, cocamine, dicocamine, methyl dicocamine, dimethylcocamine, dimethyldodecylamine, dimethyltetradecylamine, dimethylhexadecylamine, dimethyltallowamine, dimethyloleylamine, dimethylsoyamine, tridodecylamine, methyl stearylamine and mixtures thereof; an effective amount of an ionizable metal salt, wherein the metal of the ionizable metal salt has a valence of at least II; and a suitable carrier; wherein the composition has a pH of from about 2.7 to about 4.5 and the ionizable metal salt and water-insoluble amino-containing compound are present in the composition in a molar or molar-equivalent ratio of at least 1:1.

69. A hair setting composition comprising an effective amount of tripropylamine; an effective amount of an ionizable metal salt, wherein the metal of the ionizable metal salt has a valence of at least II; and a suitable carrier; wherein the composition has a pH of from about 2.7 to about 4.5 and the ionizable metal salt and water-insoluble amino-containing compound are present in the composition in a molar or molar-equivalent ratio of at least 1:1.

70. A hair setting composition comprising an effective amount of a water-insoluble amino-containing compound having a water-solubility of 0.5 g or less per 100 milliliters of water, wherein the water-insoluble amino-containing compound is selected from the group consisting of octylamine, pentylamine, dipentylamine, water-insoluble polyethylenimines, trimethylsilylamodimethicone, dioctylamine, trioctylamine, tripropylamine, cocamine, hydrogenated tallow amine, dihydrogenated tallow amine, trihydrogenated tallow amine and mixtures thereof; an effective amount of an ionizable metal salt, wherein the metal of the ionizable metal salt has a valence of at least II; and a suitable carrier; wherein the composition has a pH of from about 2.7 to about 4.5 and the ionizable metal salt and water-insoluble amino-containing compound are present in the composition in a molar or molar-equivalent ratio of at least 1:1.

71. A method of treating human hair with a hair setting composition comprising contacting human hair with a composition comprising an effective amount of a water-insoluble amino-containing compound selected from the group consisting of octylamine, dioctylamine, trioctylamine, dimethyloctylamine, pentylamine, dipentylamine, hexylamine, dihexylamine, trihexylamine, heptylamine, dodecylamine, hexadecylamine, octadecylamine, tallow amine, hydrogenated tallow amine, dihydrogenated tallow amine, trihydrogenated tallow amine, oleyl amine, soya amine, cocamine, dicocamine, methyl dicocamine, dimethylcocamine, dimethyldodecylamine, dimethyltetradecylamine, dimethylhexadecylamine, dimethyltallowamine, dimethyloleylamine, dimethylsoyamine, tridodecylamine, methyl stearylamine and mixtures thereof; an effective amount of an ionizable metal salt, wherein the metal of the ionizable metal salt has a valence of at least II; and a suitable carrier; wherein the composition has a pH of from 2.7 to about 4.5 and the ionizable metal salt and water-insoluble amino-containing compound are present in the composition in a molar or molar-equivalent ratio of at least 1:1.

72. A method of treating human hair with a hair setting composition comprising contacting human hair with a composition comprising an effective amount of a water-insoluble amino-containing compound having a water solubility of 0.5 g or less per 100 milliliters of water, wherein the water-insoluble amino-containing compound is tripropylamine; an effective amount of an ionizable metal salt, wherein the metal of the ionizable metal salt has a valence of at least II; and a suitable carrier; wherein the composition has a pH of from about 2.7 to about 4.5 and the ionizable metal salt and water-insoluble amino-containing compound are present in the composition in a molar or molar-equivalent ratio of at least 1:1.

73. A method of treating human hair with a hair setting composition comprising contacting human hair with a composition comprising an effective amount of a water-insoluble amino-containing compound having a water solubility of 0.5 g or less per 100 milliliters of water, wherein the water-insoluble amino-containing compound is selected from the group consisting of octylamine, pentylamine, dipentylamine, water-insoluble polyethylenimines, trimethylsilylamodimethicone, dioctylamine, trioctylamine, tropropylamine, cocamine, hydrogenated tallow amine, dihydrogenated tallow amine, trihydrogenated tallow amine and mixtures thereof; an effective amount of an ionizable metal salt, wherein the metal of the ionizable metal salt has valence of at least II; and a suitable carrier; wherein the composition has a pH of from about 2.7 to about 4.5 and the ionizable metal salt and water-insoluble amino-containing compound are present in the composition in a molar or molar-equivalent ratio of at least 1:1.

74. A method of treating human hair to provide durable hair set retention properties comprising contacting human hair with a first hair treating composition comprising an effective amount of a water-insoluble amino-containing compound in a suitable carrier and having a pH of from about 2.7 to about 4.5, wherein the water-insoluble amino-containing compound has a water solubility of 0.5 g or less per 100 milliliters of water and is selected from the group consisting of:
  (a) a primary amine including an alkyl group or a substituted alkyl group of between five and about 20 carbon atoms in length,
  (b) a secondary amine including two alkyl groups or substituted alkyl groups of about 20 or less carbon atoms in length and wherein one of the alkyl or substituted alkyl groups is at least five carbon atoms in length,
  (c) a tertiary amine including three alkyl groups or substituted alkyl groups of about 20 or less carbon atoms in length and wherein at least one of the three alkyl or substituted alkyl groups is at least five carbon atoms in length,
  (d) an amino-functionalized silicone, and
  (e) combinations thereof;
  then contacting the human hair with a second hair treating composition comprising an effective amount of an ionizable metal salt in a suitable carrier and having a pH of from about 2.7 to about 4.5, wherein the metal of the ionizable metal salt has a valence of at least II.

75. A method of treating human hair to provide durable hair set retention properties comprising contacting human hair with a first hair treating composition comprising an effective amount of an ionizable metal salt in a suitable in a suitable carrier and having a pH of from about 2.7 to about 4.5, wherein the metal of the ionizable metal salt has a valence of at least II;
  and then contacting the human hair with a second hair treating composition comprising an effective amount of a water-insoluble amino-containing compound in a suitable carrier and having a pH of from about 2.7 to about 4.5, wherein the water-insoluble amino-containing compound has a water solubility of 0.5 g or less per 100 milliliters of water and is selected from the group consisting of:
(a) a primary amine including an alkyl group or a substituted alkyl group of between five and about 20 carbon atoms in length,
(b) a secondary amine including two alkyl groups or substituted alkyl groups of about 20 or less carbon atoms in length and wherein one of the alkyl or substituted alkyl groups is at least five carbon atoms in length,
(c) a tertiary amine including three alkyl groups or substituted alkyl groups of about 20 or less carbon atoms in length and wherein at least one of the three alkyl or substituted alkyl groups is at least five carbon atoms in length,
(d) an amino-functionalized silicone, and
(e) combinations thereof.

* * * * *